United States Patent [19]

Takasugi et al.

[11] Patent Number: 5,574,016

[45] Date of Patent: Nov. 12, 1996

[54] PEPTIDE COMPOUND AND A PROCESS FOR THE PREPARATION THEREOF

[75] Inventors: Hisashi Takasugi, Osaka; Akito Tanaka, Takarazuka; Hiroyoshi Sakai, Uji; Takatoshi Ishikawa, Ikeda, both of Japan

[73] Assignee: Fujisawa Pharmaceutical Co., Ltd., Osaka, Japan

[21] Appl. No.: 446,288

[22] Filed: May 22, 1995

Related U.S. Application Data

[63] Continuation of Ser. No. 148,403, Nov. 8, 1993, abandoned, which is a continuation of Ser. No. 881,720, May 12, 1992, abandoned.

[30] Foreign Application Priority Data

May 13, 1991 [GB] United Kingdom .................. 9110298
Feb. 3, 1992 [GB] United Kingdom .................. 9202260

[51] Int. Cl.$^6$ .............................. A61K 38/00; C07K 5/00; C07K 7/00; C07K 17/00
[52] U.S. Cl. .............................. 514/18; 514/19; 514/822; 562/444; 562/448; 530/331
[58] Field of Search .............................. 514/17–19, 822; 562/444, 448; 530/331

[56] References Cited

U.S. PATENT DOCUMENTS

| 4,857,508 | 8/1989 | Adams et al. |
| 5,039,805 | 8/1991 | Alig et al. |

FOREIGN PATENT DOCUMENTS

| 2008116 | 8/1990 | Canada. | |
| 0384 362 | 8/1990 | European Pat. Off.. | |
| 0445796 | 3/1991 | European Pat. Off.. | |
| 0445 796 | 9/1991 | European Pat. Off.. | |
| 0502536A1 | 9/1992 | European Pat. Off. | C07K 5/02 |
| WO92/15607 | 9/1972 | WIPO | C07K 5/06 |

OTHER PUBLICATIONS

Die Pharmazie, vol. 39, No. 6, 1988, pp. 412–414, B. Voigt, et al., "Synthese Von Nα–(Arylsulfonyl)– 4–Amidino–Phenylalanyl–Prolinen und Von Nα–(Arylsulfonylglycyl)– 4–Amidino–Phenylalanyl–prolinen und deren prüfung Als Inhibitoren von Serinproteinasen".

Die Pharmazie, vol. 39, No. 2, 1984, pp. 82–84, H. Vieweg, et al., "Synthese von Nα–Tosyl –4–Amidinophenylalaninderivaten mit Zwei C–Terminal Eingeschobenen Aminosäuren ALS Potentielle Inhibitoren von Serinproteinasen".

*Chemistry and Biochemistry of Amino Acids and Proteins*—vol. 7 Spatola, Edited by Boris Neinstein (Marcel Dekkern 1983) pp. 267–357.

Walsman et al. *Pharmazie*37(6):457 (1982) Translated pp. 1–4.

Rudtinger, *Peptide Hormones*(ed. J. A. Parsons) (Univ. Press 1976) pp. 1–7.

Pierschbacher et al. J. Biol. Chem. vol. 262 No. 36 pp. 17294–17298.

*Primary Examiner*—Toni R. Scheiner
*Assistant Examiner*—Sheela J. Huff
*Attorney, Agent, or Firm*—Oblon, Spivak, McClelland, Maier & Neustadt, P.C.

[57] ABSTRACT

The present invention concerns glycoprotein IIa/IIIb antagonists and platelet aggregation inhibitors of the formula (I):

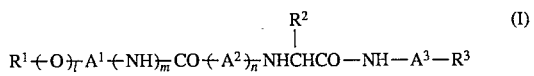

wherein

R$^1$ is aryl which may have one or more suitable substituent(s),

R$^2$ is carboxy(lower)alkyl or protected carboxy(lower)alkyl,

R$^3$ is carboxy or protected carboxy,

A$^1$ is alkylene which may have one or more suitable substituent(s),

A$^2$ is a group of the formula:

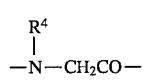

(wherein R is lower alkyl), or a group of the formula:

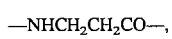

A$^3$ is lower alkylene which may have one or more suitable substituent(s), l, m and n are each the same or different an integer of 0 or 1, with proviso that A$^2$ is not a group of the formula:

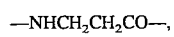

when l is an integer of 0.

7 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2..3

( i x ) FEATURE:
        ( A ) NAME/KEY: Modified-site
        ( B ) LOCATION: 3..4

( i x ) FEATURE:
 ( A ) NAME/KEY: Modified-site
 ( B ) LOCATION: 1..2

( x i ) SEQUENCE DESCRIPTION: SEQ ID NO:1:

Xaa Gly Asp Val
 1

PEPTIDE COMPOUND AND A PROCESS FOR THE PREPARATION THEREOF

This application is a Continuation of application Ser. No. 08/148,403, filed on Nov. 8, 1993, now abandoned; which was a Continuation of application Ser. No. 07/881,720, filed on May 12, 1992, now abandoned.

The present invention relates to new peptide compound and a salt thereof. More particularly, it relates to new peptide compound and a salt thereof which is glycoprotein IIb/IIIa antagonist and inhibitor of platelet aggregation, and useful as:

a drug for the prevention and/or the treatment of diseases caused by thrombus formation such as arterial thrombosis; arterial sclerosis; ischemic heart diseases [e.g. angina pectoris (e.g. stable angina pectoris, unstable angina pectoris including imminent infarction, etc), myocardial infarction (e.g. acute myocardial infarction, etc), coronary thrombosis, etc]; ischemic brain diseases [e.g. cerebral infarction {e.g. cerebral thrombosis (e.g. acute cerebral thrombosis, etc), cerebral embolism, etc}, transient cerebral ischemia, cerebrovascular spasm after cerebral hemorrhage (e.g. cerebrovascular spasm after subarachnoid hemorrhage, etc), etc]; pulmonary vascular diseases (e.g. pulmonary thrombosis, pulmonary embolism, etc); peripheral circulatory disorder [e.g. arteriosclerosis obliterans, thromboangiitis obliterans (i.e. Bürger's disease), Raynaud's disease, complication of diabetes mellitus (e.g. diabetic angiopathy, etc), phlebothrombosis (e.g. deep vein thrombosis, etc), etc] or the like;

a drug for the prevention and/or the treatment of restenosis and/or reocclusion such as restenosis and/or reocclusion after percutaneous transluminal coronary angioplasty (PTCA), restenosis and/or reocclusion after the administration of tissue plasminogen activator (TPA) or the like;

a drug for the adjuvant therapy with thrombolytic drug (e.g. TPA, etc) or anticoagulant (e.g. heparin, etc);

a drug for the prevention and/or the treatment of the thrombus formation in case of vascular surgery, valve replacement, extracorporeal circulation (e.g. sergery, hemodialysis, etc), transplantation, or the like;

a drug for the prevention and/or the treatment of disseminated intravascular coagulation (DIC), thrombotic thrombocytopenic, essential thrombocytosis, inflammation (e.g. nephritis, etc), immune diseases, or the like;

a drug for inhibiting of metastasis; or the like.

The peptide compound of the present invention is expected to be useful as an inhibitor of cell adhesion and so is expected to be useful as a drug for the prevention and/or the treatment of disseminated intravascular coagulation (DIC), thrombotic thrombocytopenic, essential thrombocytosis, inflammation (e.g. nephritis, etc), immune diseases, or the like;

a drug for inhibiting of metastasis, or the like.

Accordingly, one object of the present invention is to provide new peptide compound or a salt thereof which is useful as stated above.

Another object of the present invention is to provide processes for preparation of said new peptide compound or a salt thereof.

A further object of the present invention is to provide a pharmaceutical composition comprising, as an active ingredient, said peptide compound or a salt thereof.

Still further object of this invention is to provide methods of using said peptide compound or a salt thereof for the prevention and/or the treatment of aforesaid diseases in a human being or an animal.

The object peptide compound of the present invention can be shown by the following formula (I):

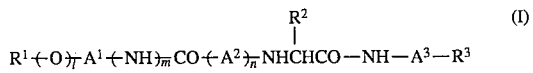

wherein $R^1$ is aryl which may have one or more suitable substituent(s), $R^2$ is carboxy(lower)alkyl or protected carboxy(lower)alkyl, $R^3$ is carboxy or protected carboxy, $A^1$ is alkylene which may have one or more suitable substituent(s), $A^2$ is a group of the formula:

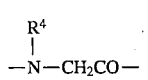

(wherein $R^4$ is lower alkyl), or a group of the formula:

$A^3$ is lower alkylene which may have one or more suitable substituent(s), l, m and n are each the same or different an integer of 0 or 1, with proviso that $A^2$ is not a group of the formula:

when l is an integer of 0.

The object compound (I) or a salt thereof can be prepared by the following processes.

Process 1

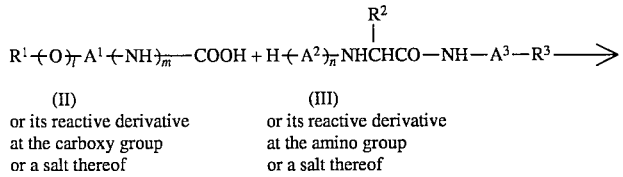

(II)
or its reactive derivative
at the carboxy group
or a salt thereof (III)
or its reactive derivative
at the amino group
or a salt thereof -continued
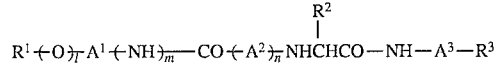
(I)
or a salt thereof
Process 2
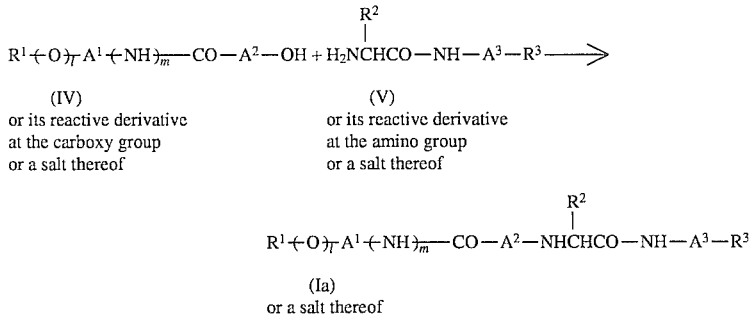
(IV)
or its reactive derivative
at the carboxy group
or a salt thereof
(V)
or its reactive derivative
at the amino group
or a salt thereof
(Ia)
or a salt thereof
Process 3
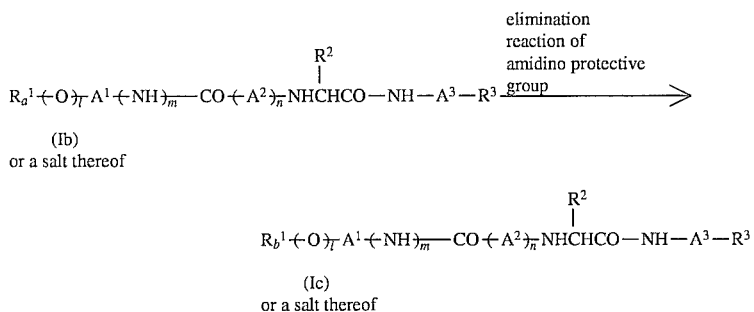
(Ib)
or a salt thereof
(Ic)
or a salt thereof
Process 4
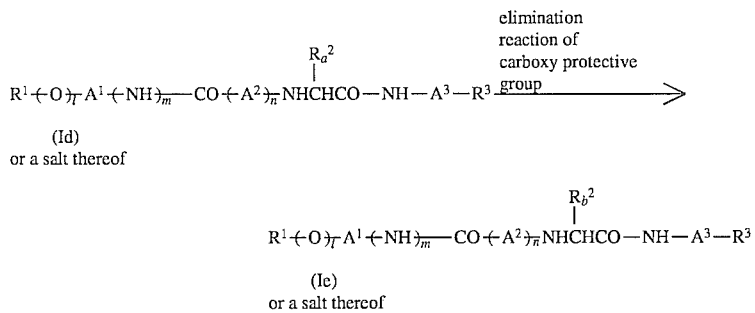
(Id)
or a salt thereof
(Ie)
or a salt thereof
Process 5
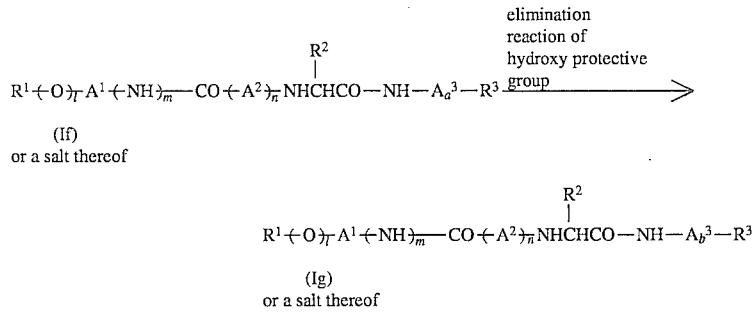
(If)
or a salt thereof
(Ig)
or a salt thereof Process 6

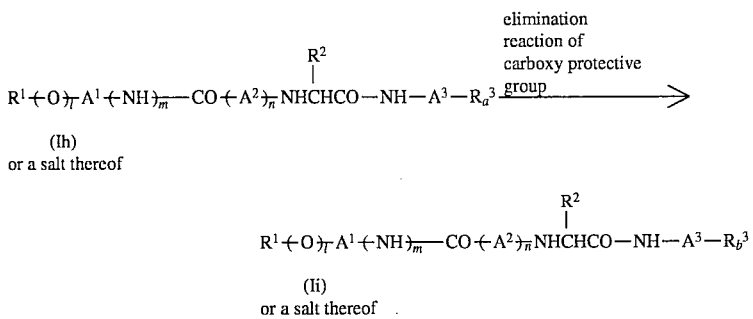

(Ih)
or a salt thereof $$R^1 \mathrm{+O+}_l A^1 \mathrm{+NH+}_{\overline{m}} \mathrm{-CO+A^2+}_{\overline{n}} \mathrm{NHCHCO-NH-A^3-R_b^3}$$

(Ii)
or a salt thereof

Process 7

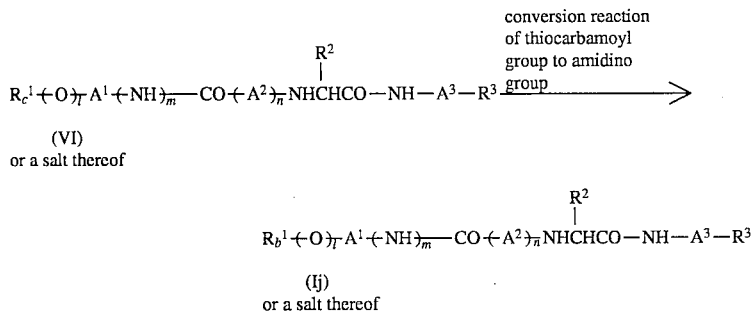

(VI)
or a salt thereof $$R_b^1 \mathrm{+O+}_l A^1 \mathrm{+NH+}_{\overline{m}} \mathrm{-CO+A^2+}_{\overline{n}} \mathrm{NHCHCO-NH-A^3-R^3}$$

(Ij)
or a salt thereof wherein $R^1$, $R^2$, $R^3$, $A^1$, $A^2$, $A^3$, l, m and n are each as defined above, $R_a^1$ is aryl having protected amidino, $R_b^1$ is aryl having amidino, $R_c^1$ is aryl having thiocarbamoyl, $R_a^2$ is protected carboxy(lower)alkyl, $R_b^2$ is carboxy(lower)alkyl, $R_a^3$ is protected carboxy, $R_b^3$ is carboxy, $A_a^3$ is lower alkylene having protected hydroxy(lower)alkyl or lower alkylene having (protected hydroxy)-ar(lower)alkyl, $A_b^3$ is lower alkylene having hydroxy(lower)alkyl or lower alkylene having(hydroxy)-ar(lower)alkyl.

Among the starting compounds (II), (III), (IV), (V) and (VI), there are novel compounds. They can be prepared from the known compounds in a conventional manner in this field of the art or the similar manners to those disclosed in Preparations and/or Examples mentioned later in the present specification.

Suitable pharmaceutically acceptable salts of the object compound (I) are conventional non-toxic salts and include a metal salt such as an alkali metal salt [e.g. sodium salt, potassium salt, etc] and an alkaline earth metal salt [e.g. calcium salt, magnesium salt, etc] an ammonium salt, an organic base salt [e.g. trimethylamine salt, triethylamine salt, pyridine salt, picoline salt, dicyclohexylamine salt, N,N-dibenzylethylenediamine salt, etc], an organic acid addition salt [e.g. formate, acetate, trifluoroacetate, maleate, tartrate, methanesulfonate, benzenesulfonate, toluenesulfonate, etc], an inorganic acid addition salt [e.g. hydrochloride, hydrobromide, hydroiodide, sulfate, phosphate, etc], a salt with an amino acid [e.g. arginine salt, aspartic acid salt, glutamic acid salt, etc] and the like.

In the above and subsequent descriptions of this specification, suitable examples of the various definitions are explained in detail as follows:

The term "lower" is intended to mean 1 to 6 carbon atom(s), unless otherwise indicated.

Suitable "aryl" may include phenyl, naphthyl (e.g. 1-naphthyl, 2-naphthyl), anthryl (e.g. 1-anthryl, 2-anthryl, 9-anthryl, etc), and the like, in which the preferred one may be phenyl.

This "aryl" may have one or more (preferably 1 to 3) suitable substituent(s) such as amidino, protected amidino or the like.

Suitable protective group in "protected amidino" may include ar(lower)alkyl such as mono or di or triphenyl(lower)alkyl [e.g. benzyl, phenethyl, 1-phenylethyl, benzhydryl, trityl, etc], acyl as explained hereinbelow, and the like.

Suitable acyl may be aliphatic acyl, aromatic acyl, aryl-aliphatic acyl and heterocyclic-aliphatic acyl derived from carboxylic acid, carbonic acid, carbamic acid, sulfonic acid, and the like.

Suitable example of the acyl group thus explained may be lower alkanoyl [e.g. formyl, acetyl, propionyl, hexanoyl, pivaloyl, etc], mono(or di or tri)halo(lower)alkanoyl [e.g. chloroacetyl, trifluoroacetyl, etc], lower alkoxycarbonyl [e.g. methoxycarbonyl, ethoxycarbonyl, tert-butoxycarbonyl, tert-pentyloxycarbonyl, hexyloxycarbonyl, etc], mono(or di or tri)halo(lower)alkoxycarbonyl [e.g. chloromethoxycarbonyl, dichloroethoxycarbonyl, trichloroethoxycarbonyl, etc], aroyl [e.g. benzoyl, toluoyl, xyloyl, naphthoyl, etc], ar(lower)alkanoyl such as phenyl(lower)alkanoyl [e.g. phenylacetyl, phenylpropionyl, etc], aryloxycarbonyl [e.g. phenoxycarbonyl, naphthyloxycarbonyl, etc], aryloxy(lower)alkanoyl such as phenoxy(lower)alkanoyl [e.g. phenoxyacetyl, phenoxypropionyl, etc], arylglyoxyloyl [e.g. phenylglyoxyloyl, naphthylglyoxyloyl, etc], ar(lower)-alkoxycarbonyl which may have suitable substituent(s) such as phenyl(lower)alkoxycarbonyl which may have nitro or lower alkoxy [e.g. benzyloxycarbonyl, phenethyloxycarbonyl, p-nitrobenzyloxycarbonyl, p-methoxybenzyloxycarbonyl, etc], thienylacetyl, imidazolylacetyl, furylacetyl, tetrazolylacetyl, triazolylacetyl, thiadiazolylacetyl, thienylpropionyl, thiadiazolylpropionyl, lower alkylsulfonyl [e.g. methylsulfonyl, ethylsulfonyl, propylsulfonyl, isopropylsulfonyl, pentylsulfonyl, butylsulfonyl, etc], arylsulfonyl [e.g. phenylsulfonyl, tolylsulfonyl, xylylsulfonyl, naphthylsulfonyl, etc], ar(lower)alkylsulfonyl such as phenyl(lower)alkylsulfonyl [e.g. benzylsulfonyl, phenethylsulfonyl, benzhydrylsulfonyl, etc], and the like.

The preferred example of "protected amidino" may be N-ar(lower)alkoxycarbonylamidino, the more preferred one may be N-phenyl(lower)alkoxycarbonylamidino, the much more preferred one may be N-phenyl($C_1$–$C_4$)alkoxycarbonylamidino, and the most preferred one may be N-benzyloxycarbonylamidino.

Suitable "lower alkyl" may be straight or branched ones such as methyl, ethyl, isopropyl, propyl, butyl, isobutyl, sec-butyl, t-butyl, pentyl, hexyl or the like, in which the preferred one may be ($C_1$–$C_4$)alkyl, and suitable "lower alkyl" moiety in "carboxy(lower)alkyl" can be referred to said "lower alkyl".

Suitable example of "carboxy(lower)alkyl" may include carboxymethyl, 1-carboxyethyl, 2-carboxyethyl, 2-carboxypropyl, 3-carboxybutyl, 2-carboxy-1,1-dimethylethyl, 5-carboxypentyl, 6-carboxyhexyl, and the like, in which the preferred one may be carboxy($C_1$–$C_4$)alkyl and the more preferred one may be carboxymethyl or 2-carboxyethyl.

Suitable "protected carboxy" moiety in "protected carboxy(lower)alkyl" may be an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxymethyl ester, 2-propionyloxyethyl ester, hexanoyloxymethyl ester, etc], lower alkanesulfonyl(lower)alkyl ester [e.g. 2-mesylethyl ester, etc] or mono(or di or tri)halo(lower)alkyl ester [e.g. 2-iodoethyl ester, 2,2,2-trichloroethyl ester, etc]; lower alkenyl ester [e.g. vinyl ester, allyl ester, etc]; lower alkynyl ester [e.g. ethynyl ester, propynyl ester, etc]; ar(lower)alkyl ester which may have suitable substituent(s) [e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc]; aryl ester which may have suitable substituent(s) [e.g. phenyl ester, 4-chlorophenyl ester, tolyl ester, 4-tert-butylphenyl ester, xylyl ester, mesityl ester, cumenyl ester, etc]; or the like, in which the preferred one may be mono or di or triphenyl($C_1$–$C_4$)alkyl ester and the most preferred one may be benzyl ester.

Suitable "lower alkyl" moiety in "protected carboxy(lower)alkyl" can be referred to aforesaid "lower alkyl".

Suitable example of said "protected carboxy(lower)alkyl" may be phenyl(lower)alkoxycarbonyl(lower)alkyl, in which the preferred one may be phenyl($C_1$–$C_4$)alkoxycarbonyl($C_1$–$C_4$)alkyl and the more preferred one may be benzyloxycarbonylmethyl or 2-benzyloxycarbonylethyl.

Suitable "protected carboxy" can be referred to the ones as exemplified for "protected carboxy" moiety of "protected carboxy(lower)alkyl" before.

Suitable example of said "protected carboxy" may be phenyl(lower)alkoxycarbonyl, in which the preferred one may be phenyl($C_1$–$C_4$)alkoxycarbonyl and the more preferred one may be benzyloxycarbonyl; or lower alkoxycarbonyl, in which the preferred one may be ($C_1$–$C_4$)alkoxycarbonyl and the more preferred one may be methoxycarbonyl or ethoxycarbonyl.

Suitable "alkylene" may be the ones having 1 to 12 carbon atom(s) such as methylene, ethylene, trimethylene, tetramethylene, pentamethylene, hexamethylene, heptamethylene, octamethylene, nonamethylene, decamethylene, undecamethylene, dodecamethylene, or the like, in which the preferred one may be ($C_1$–$C_{10}$)alkylene and the more preferred one may be methylene, ethylene, trimethylene, tetramethylene, pentamethylene, or heptamethylene.

This "alkylene" may have one or more (preferably 1 to 3) suitable substituent(s) such as amino, protected amino, or the like.

Suitable protective group in said "protected amino" can be referred to the ones as exemplified above for the ones for "protected amidino".

The preferred example of "protected amino" may be lower alkanoylamino or lower alkoxycarbonylamino, in which the more preferred one may be ($C_1$–$C_4$)alkanoylamino or ($C_1$–$C_4$)alkoxycarbonylamino and the most preferred one may be acetylamino or t-butoxycarbonylamino.

Suitable "lower alkylene" may include methylene, ethylene, trimethylene, tetramethylene, pentamethylene, hexamethylene, and the like, in which the preferred one may be ($C_1$–$C_4$)alkylene and the more preferred one may be methylene or trimethylene.

This "lower alkylene" may have one or more (preferably 1 to 3) suitable substituent(s) such as aforesaid lower alkyl; ar(lower)alkyl which may have one or more suitable substituent(s) explained later; hydroxy(lower)alkyl (e.g. hydroxymethyl, 1-hydroxyethyl, 2-hydroxyethyl, 3-hydroxypropyl, 2-hydroxybutyl, 1,1-dimethyl-2-hydroxyethyl, 5-hydroxypentyl, 6-hydroxyhexyl, etc); protected hydroxy(lower)alkyl explained later; [cyclo(lower)alkyl]-(lower)alkyl (e.g. cyclopropylmethyl, cyclobutylmethyl, cyclohexylmethyl, 2-cyclopentylethyl, 1-cyclohexylethyl, 3-cyclopentylpropyl, 2-cyclohexylbutyl, 1,1-dimethyl-2-cyclopropylethyl, 5-cyclobutylpentyl, 6-cyclohexylhexyl, etc); heterocyclic(lower)alkyl explained later; or the like.

Suitable "ar(lower)alkyl" on "lower alkylene" as stated above may include mono-(or di- or tri-)phenyl(lower)alkyl such as benzyl, phenethyl, 2-phenylpropyl, 4-phenylbutyl, 1,1-dimethyl-2-phenylethyl, 5-phenylpentyl, 6-phenylhexyl, diphenylmethyl, 1,2-diphenylethyl, trityl, 1,2,3-triphenylpropyl, or the like, in which the preferred one may be phenyl($C_1$–$C_4$)alkyl and the more preferred one may be benzyl.

This "ar(lower)alkyl" may have one or more (preferably 1 to 3) suitable substituent(s) such as hydroxy; protected hydroxy [e.g. ar(lower)alkyloxy, in which "ar(lower)alkyl" moiety can be referred to the ones explained before; acyloxy, in which "acyl" moiety can be referred to the ones explained before, etc]; lower alkoxy (e.g. methoxy, ethoxy, propoxy, butoxy, t-butoxy, pentyloxy, hexyloxy, etc); or the like, in which the preferred one may be hydroxy, phenyl($C_1$–$C_4$)alkyloxy or ($C_1$–$C_4$)alkoxy, and the more preferred one may be hydroxy, benzyloxy, methoxy or ethoxy.

Suitable "protected hydroxy(lower)alkyl" may include ar(lower)alkyloxy(lower)alkyl, acyloxy(lower)alkyl, and the like, in which "ar(lower)alkyl" moiety, "acyl" moiety and "(lower)alkyl" moiety can be referred to the ones explained before.

The preferred "protected hydroxy(lower)alkyl" may be phenyl($C_1$–$C_4$)alkyloxy($C_1$–$C_4$)alkyl, and the more preferred one may be benzyloxymethyl or 1-benzyloxyethyl.

Suitable "heterocyclic" moiety in "heterocyclic(lower)alkyl" means saturated or unsaturated, monocyclic or polycyclic heterocyclic group containing at least one heteroatom such as an oxygen, sulfur, nitrogen atom and the like. And, especially preferably heterocyclic group may be heterocyclic group such as

- unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc), tetrazolyl (e.g., 1H-tetrazolyl, 2H-tetrazolyl, etc), dihydrotriazinyl (e.g., 4,5-dihydro-1,2,4-triazinyl, 2,5-dihydro-1,2,4-triazinyl, etc), etc;
- saturated 3 to 8-membered heteromonocyclic group containing 1 to 4 nitrogen atom(s), for example, pyrrolidinyl, imidazolidinyl, piperidyl (e.g. piperidino, etc), piperazinyl, etc;
- unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc), dihydrotriazolopyridazinyl, etc;
- unsaturated 3 to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc), etc;
- saturated 3 to 8-membered heteromonocyclic group containing 1 to 2 oxygen atom(s) and 1 to 3 nitrogen atom(s), for example, morpholinyl, oxazolidinyl (e.g. 1,3-oxazolidinyl, etc), etc;
- unsaturated condensed heterocyclic group containing 1 to 2 oxygen atom(s) and 1 to 3 nitrogen atom(s), for example, benzoxazolyl, benzoxadiazolyl, etc;
- unsaturated 3 to 8-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc;
- saturated 3 to 8-membered heteromonocyclic group containing 1 to 2 sulfur atom(s) and 1 to 3 nitrogen atom(s), for example, thiazolidinyl, etc;
- unsaturated 3 to 8-membered heteromonocyclic group containing a sulfur atom, for example, thienyl, etc; unsaturated condensed heterocyclic group containing 1 to 2 sulfur atom(s) and 1 to 3 nitrogen atom(s), for example, benzothiazolyl, benzothiadiazolyl, etc;
- unsaturated 3 to 8-membered heteromonocyclic group containing 1 to 2 oxygen atom(s), for example, furyl, pyranyl, dioxolyl, etc;
- saturated 3 to 8-membered heteromonocyclic group containing 1 to 2 oxygen atom(s), for example, oxolanyl, tetrahydropyranyl (e.g. tetrahydro-2H-pyran-2-yl, etc), dioxolanyl, etc;
- unsaturated condensed heterocyclic group containing 1 to 2 oxygen atom(s), for example, isobenzofuranyl, chromenyl (e.g. 2H-chromen-3-yl, etc), dihydrochromenyl (e.g. 3,4-dihydro-2H-chromen-4-yl, etc), etc; and the like.

The preferred "heterocyclic" moiety may be unsaturated 3 to 8-membered heteromonocyclic group containing 1 to 4 nitrogen atom(s) and the more preferred one may be pyridyl.

Among the suitable substituent(s) on "lower alkylene", the preferred one may be ($C_1$–$C_4$)alkyl; phenyl($C_1$–$C_4$)alkyl which may have 1 to 3 hydroxy, phenyl($C_1$–$C_4$)alkyloxy or ($C_1$–$C_4$)alkoxy; hydroxy($C_1$–$C_4$)alkyl; phenyl($C_1$–$C_4$)alkyloxy($C_1$–$C_4$)alkyl; cyclo($C_5$–$C_6$)alkyl($C_1$–$C_4$)alkyl; or pyridyl($C_1$–$C_4$)alkyl, and the more preferred one may be methyl, ethyl, propyl, isopropyl, butyl, 1-methylpropyl, 2-methylpropyl, t-butyl, benzyl, (4-hydroxyphenyl)methyl, (4-benzyloxyphenyl)methyl, (4-methoxyphenyl)methyl, (4-ethoxyphenyl)methyl, hydroxymethyl, 1-hydroxyethyl, benzyloxymethyl, 1-benzyloxyethyl, cyclohexylmethyl, or 2-pyridylmethyl.

The term "(hydroxy)-ar(lower)alkyl" means ar(lower)alkyl having hydroxy.

The term "(protected hydroxy)-ar(lower)alkyl" means ar(lower)alkyl having protected hydroxy.

The processes for preparing the object compounds of the present invention are explained in detail in the following.

Process 1

The object compound (I) or a salt thereof can be prepared by reacting a compound (II) or its reactive derivative at the carboxy group or a salt thereof with a compound (III) or its reactive derivative at the amino group or a salt thereof.

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc], dialkylphosphorous acid, sulfurous acid, thiosulfuric acid, sulfuric acid, sulfonic acid [e.g. methanesulfonic acid, etc], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc] or aromatic carboxylic acid [e.g. benzoic acid, etc]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc], and the like. These reactive derivatives can optionally be selected from them according to the kind of the compound (II) to be used.

Suitable salts of the compound (II) and its reactive derivative can be referred to the ones as exemplified for the compound (I).

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide, bis(trimethylsilyl)urea or the like; a derivative formed by reaction of the compound (III) with phosporus trichloride or phosgene, and the like.

Suitable salts of the compound (III) and its reactive derivative can be referred to the ones as exemplified for the compound (I).

The reaction is usually carried out in a conventional solvent such as water, alcohol [e.g. methanol, ethanol, etc], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkylphosphite; ethyl polyphosphate; isopropyl polyphosphate; phosphorous oxychloride (phosphoryl chloride); phosphorus trichloride; thionyl chloride; oxalyl chloride; lower alkyl haloformate [e.g. ethyl chloroformate, isopropyl chloroformate, etc]; triphenylphosphine; 2-ethyl-7-hydroxybenzisoxazolium salt; 2-ethyl-5-(m-sulfophenyl)isoxazoliumhydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc; or the like.

The reaction may also be carried out in the presence of an inorganic or organic base such as an alkali metal carbonate, alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Process 2

The object compound (Ia) or a salt thereof can be prepared by reacting a compound (IV) or its reactive derivative at the carboxy group or a salt thereof with a compound (V) or its reactive derivative at the amino group or a salt thereof.

This reaction can be carried out in a similar manner to that of Process 1 mentioned in the above, and therefore the reaction mode and reaction conditions [e.g. reactive derivative, solvent, reaction temperature, etc] of this reaction are to be referred to those as explained in Process 1.

Process 3

The object compound (Ic) or a salt thereof can be prepared by subjecting a compound (Ib) or a salt thereof to elimination reaction of amidino protective group.

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc], an alkaline earth metal [e.g. magnesium, calcium, etc], the hydroxide or carbonate or bicarbonate thereof, trialkylamine [e.g. trimethylamine, triethylamine, etc], picoline, 1,5-diazabicyclo[4.3.0]non-5-ene, 1,4-diazabicyclo[2.2.2]octane, 1,8-diazabicyclo[5.4.0]- undec-7-ene, or the like.

Suitable acid may include an organic acid [e.g. formic acid, acetic acid, propionic acid, trichloroacetic acid, trifluoroacetic acid, etc] and an inorganic acid [e.g. hydrochloric acid, hydrobromic acid, sulfuric acid, hydrogen chloride, hydrogen bromide, etc]. The elimination using Lewis acid such as trihaloacetic acid [e.g. trichloroacetic acid, trifluoroacetic acid, etc] or the like is preferably carried out in the presence of cation trapping agents [e.g. anisole, phenol, etc].

The reaction is usually carried out in a solvent such as water, an alcohol [e.g. methanol, ethanol, etc], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc] or metallic compound [e.g. chromium chloride, chromium acetate, etc] and an organic or inorganic acid [e.g. formic acid, acetic acid, propionic acid, trifluoroacetic acid, p-toluenesulfonic acid, hydrochloric acid, hydrobromic acid, etc].

Suitable catalysts to be used in catalytic reduction are conventional ones such as platinum catalysts [e.g. platinum plate, spongy platinum, platinum black, colloidal platinum, platinum oxide, platinum wire, etc], palladium catalysts [e.g. spongy palladium, palladium black, palladium oxide, palladium on carbon, colloidal palladium, palladium on barium, sulfate, palladium on barium carbonate, etc], nickel catalysts [e.g. reduced nickel, nickel oxide, Raney nickel, etc], cobalt catalysts [e.g. reduced cobalt, Raney cobalt, etc], iron catalysts [e.g. reduced iron, Raney iron, etc], copper catalysts [e.g. reduced copper, Raney copper, Ullman copper, etc] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc, or a mixture thereof.

The reaction temperature of this reduction is not critical and the reaction is usually carried out under cooling to warming.

The present invention includes within the scope of the invention the case that protected carboxy(lower)alkyl in $R^2$ is transformed into carboxy(lower)alkyl, the case that protected carboxy in $R^3$ is transformed into carboxy and the case that lower alkylene having protected hydroxy(lower)alkyl or lower alkylene having (protected hydroxy)-ar(lower)alkyl in $A^3$ is transformed into lower alkylene having hydroxy(lower)alkyl or lower alkylene having (hydroxy)-ar(lower)alkyl.

Process 4

The object compound (Ie) or a salt thereof can be prepared by subjecting a compound (Id) or a salt thereof to elimination reaction of the carboxy protective group.

This reaction can be carried out in a similar manner to that of Process 3 mentioned in the above, and therefore the reaction mode and reaction conditions [e.g. base, acid, catalyst, solvent, reaction temperature, etc] of this reaction are to be referred to those as explained in Process 3.

The present invention includes within the scope of the invention the case that aryl having protected amidino in $R^1$ is transformed into aryl having amidino, the case that protected carboxy in $R^3$ is transformed into carboxy and the case that lower alkylene having protected hydroxy(lower)-alkyl or lower alkylene having (protected hydroxy)-ar(lower)alkyl in $A^3$ is transformed into lower alkylene having hydroxy(lower)alkyl or lower alkylene having (hydroxy)-ar(lower)alkyl.

Process 5

The object compound (Ig) or a salt thereof can be prepared by subjecting a compound (If) or a salt thereof to elimination reaction of the hydroxy protective group.

This reaction can be carried out in a similar manner to that of Process 3 mentioned in the above, and therefore the reaction mode and reaction conditions [e.g. base, acid, catalyst, solvent, reaction temperature, etc] of this reaction are to be referred to those as explained in Process 3.

The present invention includes within the scope of the invention the case that aryl having protected amidino in $R^1$ is transformed into aryl having amidino, the case that protected carboxy(lower)alkyl in $R^2$ is transformed into carboxy(lower)alkyl, and the case that protected carboxy in $R^3$ is transformed into carboxy.

Process 6

The object compound (Ii) or a salt thereof can be prepared by subjecting a compound (Ih) or a salt thereof to elimination reaction of the carboxy protective group.

This reaction can be carried out in a similar manner to that of Process 3 mentioned in the above, and therefore the reaction mode and reaction conditions [e.g. base, acid, catalyst, solvent, reaction temperature, etc] of this reaction are to be referred to those as explained in Process 3.

The present invention includes within the scope of the invention the case that aryl having protected amidino in $R^1$ is transformed into aryl having amidino, the case that protected carboxy(lower)alkyl in $R^2$ is transformed into carboxy(lower)alkyl, and the case that lower alkylene having protected hydroxy(lower)alkyl or lower alkylene having (protected hydroxy)-ar(lower)alkyl in $A^3$ is transformed into lower alkylene having hydroxy(lower)alkyl or lower alkylene having (hydroxy)-ar(lower)alkyl.

Process 7

The object compound (Ij) or a salt thereof can be prepared by subjecting a compound (VI) or a salt thereof to conversion reaction of thiocarbamoyl group to amidino group.

Suitable salts of the compounds (Ij) and (VI) can be referred to the ones as exemplified for the compound (I).

This reaction can be carried out by reacting the compound (VI) or a salt thereof with alkylating agent such as alkyl halide (e.g. methyl iodide, ethyl bromide, etc) or the like in a suitable solvent such as acetone, dioxane, tetrahydrofuran or the like, at room temperature, under warming to heating, and then reacting the resultant intermediate, with or without the isolation, with ammonia or its derivative such as ammonium acetate, ammonium halide (e.g. ammonium chloride etc) in a suitable solvent such as alcohol (e.g. methanol, ethanol, etc), N,N-dimethylformamide, or the like, under warming to heating.

When the object compound (I) obtained by the above-mentioned processes is in a free form, it can be converted into a salt form in a conventional manner. On the other hand, when the object compound (I) thus obtained is in a salt form, it can be converted into a free form or another salt form also in a conventional manner.

It is to be noted that the object compound (I) may include stereo isomers due to its asymmetric carbon atom(s).

Now in order to show the utility of the object compound (I), some pharmacological test data of the representative compound (I) of the present invention are shown in the following.

Test 1: Effect on platelet aggregation induced by adenosine diphosphate (ADP)

Test Compound (1) the object compound (7) of Example 7

Test Method

Platelet rich plasma (PRP) which contains $3 \times 10^8$ platelets/ml was prepared from human blood. To the 225 µl of PRP, 25 µl of drug solution* was added, and then stirred for 2 minutes at 37° C. To the solution 5 µl of ADP (final 2.5 µM) was added as an aggregation inducer. Aggregation was measured by using an aggregometer (NKK HEMA-TRACER 1). Activity of inhibitor (test compound) was expressed as $IC_{50}$ value i.e. dose required to inhibit the platelet aggregation response by 50%.

Drug solution*—Test compound was dissolved in dimethylsulfoxide.

Test Result

| Test Compound | $IC_{50}$ (M) |
| --- | --- |
| (1) | $1.0 \times 10^{-7}$ |

Test 2: Fibrinogen binding to platelets

Test Compound the same compound (1) as used in Test 1

Test Method

Washed human platelets were prepared from platelet-rich plasma by gel filtration. The washed platelets were activated with 20 µM ADP for 10 minutes and then fixed for 30 minutes with 0.8% paraformaldehyde. The platelets were then washed by centrifugation and suspended in HEPES-Tyrodes buffer containing 2 mM $CaCl_2$ and 1 mM $MgCl_2$.

350 µl of platelets were incubated at a final concentration of $2 \times 10^8$/ml with 100 µg/ml $^{125}$I-fibrinogen and test compound. The reaction was left for 30 minutes at room temperature. 3 aliquots of 100 µl were then layered onto 20% sucrose and the platelets were pelleted by centrifugation at 10,000 rpm for 5 minutes. The pellet was recovered by cutting the tip of the tube with a blade and counted in a gamma counter.

Specific binding was calculated by subtracting the binding in the presence of 50-fold excess unlabeled fibrinogen. Result was expressed at $IC_{50}$ value, i.e. dose required to inhibit the binding by 50%.

Test Result

| Test Compound | $IC_{50}$ |
| --- | --- |
| (1) | $2.8 \times 10^{-8}$ |

Test 3.: Test on enhancement of thrombolytic activity of TPA in thrombosis model in Guinea-pig Test Compound (1) the object compound (13) of Example 13

Test Method

Male Hartley guinea-pigs (500–800 g) were anesthetized with urethane (1.25 g/kg i.p.). The carotid artery and cervical vein were carefully exposed after a midline cervical insision. The vein was cannulated with a polyethylene catheter (PE50; Becton Dikinson, U.S.A.) for the injection and infusion of the drug. A pulse Dopplar flow probe was placed around the carotid artery to record the blood flow velocity to moniter thrombus formation and thrombolysis. Carotid artery thrombosis was induced by the $FeCl_3$ method as follows;

a square (1 mm×1 mm) of ADVANTEC No. 2 filter paper immersed in 20% FeCl$_3$ was placed on the carotid artery which became occluded by a thrombus.

When the blood flow velocity decreased to zero, the filter paper was removed from the vessel and the carotid artery were washed with saline more than 4 times. The test compound or saline was injected 3 minutes after the washing and 3 minutes later r-TPA [Actilyse (trademark); Boehringer Ingelheim Ltd] was infused for 60 minutes.

The animals were divided into the following groups;

Group 1 (5 animals): Saline and r-TPA at 0.30 mg/kg i.v. bolus +1.0 mg/kg/hour i.v. infusion Group 2 (5 animals): Test compound at 0.32 mg/kg i.v. bolus and r-TPA at 0.30 mg/kg i.v. bolus +1.0 mg/kg/hour i.v. infusion The reperfusion was defined as 50 % recovery of carotid artery blood flow velocity compared with the initial value. The blood flow was recorded up to 90 minutes.

Test Results

The number of the animals in which the reperfusion was observed in each group is as follows.

| Group | number of animals in which reperfusion was observed |
|---|---|
| 1 | 1 |
| 2 | 5 |

The pharmaceutical composition of the present invention can be used in the form of a pharmaceutical preparation, for example, in solid, semisolid or liquid form, which contains the object compound (I) or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation.

The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used.

The object compound (I) or a pharmaceutically acceptable salt thereof is/are included in the pharmaceutical composition in an amount sufficient to produce the desired effect upon the process or condition of the diseases.

The pharmaceutical composition of the present invention can be manufactured by the conventional method in this field of the art. If necessary, the technique generally used in this field of the art for improving the bioavailability of a drug can be applied to the pharmaceutical composition of the present invention.

For applying the composition to a human being or an animal, it is preferable to apply it by intravenous (including i.v. infusion), intramuscular, pulmonary, or oral administration, or insufflation including aerosols from metered dose inhalator, nebulyzer or dry powder inhalator.

While the dosage of therapeutically effective amount of the object compound (I) varies from and also depends upon the age and condition of each individual patient to be treated, in the case of intravenous administration, a daily dose of 0.001–100 mg of the object compound (I) per kg weight of a human being or an animal, in the case of intramuscular administration, a daily dose of 0.001–100 mg of the object compound (I) per kg weight of a human being or an animal, in case of oral administration, a daily dose of 0.001–200 mg of the object compound (I) per kg weight of a human being or an animal is generally given for the prevention and/or the treatment of aforesaid diseases in a human being or an animal.

The following preparations and examples are given only for the purpose of illustrating the present invention in more detail.

Preparation 1

A mixture of 4-cyanophenol (5.96 g), ethyl 5-bromovalerate (11.5 g), potassium carbonate (7.6 g) in N,N-dimethylformamide (60 ml) was stirred at room temperature for 14 hours.

The reaction mixture was poured into a water, and the resultant mixture was extracted with ethyl acetate. The extract was washed with saturated aqueous solution of sodium bicarbonate, water and aqueous solution of sodium chloride, and dried over magnesium sulfate. After filtration, the filtrate was evaporated in vacuo, and the resulting precipitate was washed with diethyl ether to give ethyl 5-(4-cyanophenoxy)valerate (11.21 g).

mp: 55°–57° C.

IR (Nujol): 2200, 1725, 1600, 1500 cm$^{-1}$

NMR (DMSO-d$_6$, δ): 1.18 (3H, t, J=7 Hz), 1.4–1.88 (4H, m), 2.37 (2H, t, J=7 Hz), 3.8–4.13 (4H, m),
7.1 (2H, d, J=8.9 Hz), 7.76 (2H, d, J=8.9 Hz)

MASS (M/Z): 247 (M$^+$)

The following compounds (preparations 2 and 3) were obtained according to a similar manner to that of Preparation 1.

Preparation 2

Ethyl 4-(4-cyanophenoxy)butyrate mp: 56°–57° C.

IR (Nujol): 2220, 1735, 1610, 1510 cm$^{-1}$

NMR (DMSO-d$_6$, δ): 1.18 (3H, t, J=4.7 Hz), 2.00 (2H, m), 2.47 (2H, t, J=4.8 Hz), 4.07 (4H, m), 7.09 (2H, d, J=4.6 Hz), 7.76 (2H, d, J=4.6 Hz)

MASS (M/Z): 233 (M$^+$)

Preparation 3

Ethyl 6-(4-cyanophenoxy)hexanoate mp: 45°–46° C.

IR (Nujol): 2220, 1720, 1590, 1565 cm$^{-1}$

NMR (DMSO-d$_6$, δ): 1.18 (3H, t, J=7.1 Hz), 1.3–1.83 (6H, m), 2.31 (2H, t, J=7.1 Hz), 3.9–4.2 (4H, m), 7.09 (2H, d, J=8.9 Hz), 7.75 (2H, d, J=8.9 Hz)

MASS (M/Z): 261 (M$^+$)

Preparation 4

To a solution of ethyl 5-(4-cyanophenoxy)valerate (24.7 g) in ethanol (250 ml) was bubbled hydrogen chloride under cooling with ice-water for 4 hours. After the end of reaction was checked by thin layer chromatography, nitrogen was bubbled at room temperature, and the resulting mixture was evaporated in vacuo, and the resulting precipitate was washed with diethyl ether to give ethyl 5-[4-{1-(ethoxy)iminomethyl}phenoxy]valerate hydrochloride (28.26 g).

mp: 110° C. (dec.)

IR (Nujol): 1720, 1635, 1600 cm$^{-1}$

NMR (DMSO-d$_6$, δ): 1.18 (3H, t, J=7.1 Hz), 1.47 (3H, t, J=7 Hz), 1.5–1.9 (4H, m), 2.38 (2H, t, J=7.1 Hz), 4.05 (2H, q, J=7.1 Hz), 4.12 (2H, t, J=5.8 Hz), 4.61 (2H, q, J=7 Hz), 7.16 (2H, d, J=9 Hz), 8.14 (2H, d, J=9 Hz), 11.54 (1H, br s)

MASS (M/Z): 293 (M$^+$ free)

The following compounds (Preparations 5 and 6) were obtained according to a similar manner to that of Preparation 4.

Preparation 5

Ethyl 4-[4-{1-(ethoxy)iminomethyl}phenoxy]butyrate hydrochloride mp: 102°–104° C.

IR (Nujol): 3420, 1735, 1610 cm$^{-1}$

NMR (DMSO-$d_6$, δ): 1.18 (3H, t, J=4.7 Hz), 1.47 (3H, t, J=4.6 Hz), 2.01 (2H, m), 2.48 (2H, t, J=4.8 Hz), 4.09 (4H, m), 4.60 (2H, q, J=4.6 Hz), 7.16 (2H, d, J=4.6 Hz), 8.15 (2H, d, J=4.6 Hz)

Preparation 6

Ethyl 6-[4-{1-(ethoxy)iminomethyl}phenoxy]hexanoate hydrochloride mp: 107° C. (dec.)

IR (Nujol): 1720, 1600, 1580, 1510 cm$^{-1}$

NMR (DMSO-$d_6$, δ): 1.17 (3H, t, J=7.1 Hz), 1.3–1.84 (6H, m), 1.47 (3H, t, J=7 Hz), 2.31 (2H, t, J=7.1 Hz), 3.92–4.2 (4H, m), 4.61 (2H, q, J=7 Hz), 7.16 (2H, d, J=9 Hz), 8.14 (2H, d, J=9 Hz), 11.54 (1H, br s)

MASS (M/Z): 307 (M$^+$ free)

Preparation 7

A mixture of ethyl 5-[4-{1-(ethoxy)iminomethyl}phenoxy]valerate hydrochloride (28.2 g), ammonium chloride (4.8 g), ethanol solution of ammonia (42 ml) in ethanol (300 ml) was stirred and refluxed for 15 hours. After cooled to room temperature, the mixture was filtered, and the filtrate was evaporated in vacuo, and the resulting precipitate was washed with diethyl ether to give ethyl 5-(4-amidinophenoxy)valerate hydrochloride (27.28 g).

mp: 150°–155° C. (dec.)

IR (Nujol): 3350, 1710, 1660, 1490 cm$^{-1}$

NMR (DMSO-$d_6$, δ): 1.18 (3H, t, J=7.1 Hz), 1.5–1.85 (4H, m), 2.38 (2H, t, J=7.1 Hz), 4.05 (2H, q, J=7.1 Hz), 4.1 (2H, t, J=5.8 Hz), 7.15 (2H, d, J=8.9 Hz), 7.85 (2H, d, J=8.9 Hz), 8.65 (4H, br)

MASS (M/Z): 264 (M$^+$ -free)

The following compounds (Preparations 8 and 9) were obtained according to a similar manner to that of Preparation 7.

Preparation 8

Ethyl 4-(4-amidinophenoxy)butyrate hydrochloride mp: 81°–84° C. (dec.)

IR (Nujol): 3420, 3250, 3100, 1720, 1670, 1600 cm$^{-1}$

NMR (DMSO-$d_6$, δ): 1.18 (3H, t, J=7.1 Hz), 1.9–2.1 (2H, m), 2.47 (2H, t, J=7.3 Hz), 3.95–4.23 (4H, m), 7.14 (2H, d, J=8.9 Hz), 7.88 (2H, d, J=8.9 Hz), 8.93 (4H, br s)

MASS (M/Z): 250 (M$^+$ free)

Preparation 9

Ethyl 6-(4-amidinophenoxy) hexanoate hydrochloride mp: ~135° C. (dec.)

IR (Nujol): 3420, 3260, 3100, 1720, 1660, 1600 cm$^{-1}$

NMR (DMSO-$d_6$, δ): 1.17 (3H, t, J=7.1 Hz), 1.31–1.85 (6H, m), 2.32 (2H, t, J=7.1 Hz), 3.95–4.2 (4H, m), 7.14 (2H, d, J=8.9 Hz), 7.89 (2H, d, J=8.9 Hz), 8.69 (4H, br )

MASS (M/Z): 278 (M$^+$ free)

Preparation 10

To a mixture of ethyl 5-(4-amidinophenoxy)valerate hydrochloride (14.6 g) in a mixture of tetrahydrofuran (150 ml) and 1N sodium hydroxide solution was added benzyloxycarbonyl chloride (10.4 ml) under cooling with ice-water for 1 hour. The mixture was stirred for 2 hours at 10° C. maintaining pH≈10 with 1N sodium hydroxide solution. The reaction mixture was poured into ethyl acetate (300 ml), and separated organic layer was washed with aqueous solution of sodium chloride, and dried over magnesium sulfate. After filtration, the filtrate was evaporated in vacuo, and the resulting precipitate was washed with diethyl ether to give ethyl 5-[4-(N-benzyloxycarbonylamidino)phenoxy]valerate (171.48 g).

mp: 88°–90° C.

IR (Nujol): 3420, 3280, 1715, 1660, 1590, 1560 cm$^{-1}$

NMR (DMSO-$d_6$, δ): 1.17 (3H, t, J=7.1 Hz), 1.55–1.85 (4H, m), 2.37 (2H, t, J=7 Hz), 4.04 (2H, q, J=7 Hz), 4.05 (2H, t, J=5.8 Hz), 5.1 (2H, s), 7.0 (2H, d, J=8.9 Hz), 7.24–7.46 (5H, m), 7.98 (2H, d, J=8.9 Hz), 9.11(2H, br s)

MASS (M/Z): 398 (M$^+$)

The following compounds (preparations 11 and 12) were obtained according to a similar manner to that of Preparation 10.

Preparation 11

Ethyl 4- [4-(N-benzyloxycarbonylamidino) phenoxy]butyrate mp: 110° C.–112° C.

IR (Nujol): 3430, 3290, 1720, 1655, 1595, 1565 cm$^{-1}$

NMR (DMSO-$d_6$, δ): 1.18 (3H, t, J=7.1 Hz), 1.84–2.1 (2H, m), 2.46 (2H, t, J=7.1 Hz), 3.9–4.19 (4H, m), 5.12 (2H, s), 7.01 (2H, d, J=8.9 Hz), 7.23–7.5 (5H, m), 7.97 (2H, d, J=8.9 Hz), 9.31 (2H, br s)

MASS (M/Z): 384 (M$^+$)

Preparation 12

Ethyl 6-[4-(N-benzyloxycarbonylamidino)phenoxy]hexanoate mp: 96°–99° C.

IR (Nujol): 3430, 3300, 1725, 1660, 1600, 1570, 1490 cm$^{-1}$

NMR (DMSO-$d_6$, δ): 1.17 (3H, t, J=7.1 Hz), 1.3–1.84 (6H, m), 2.31 (2H, t, J=7.1 Hz), 3.92–4.16 (4H, m), 5.1 (2H, s), 7.0 (2H, d, J=8.9 Hz), 7.25–7.5 (5H, m), 7.99 (2H, d, J=8.9 Hz), 9.12 (2H, br s)

MASS (M/Z): 412 (M$^+$)

Preparation 13

A mixture of ethyl 5-[4-(N-benzyloxycarbonylamidino)phenoxy]valerate (17.4 g) in 10% hydrochloric acid (150 ml) and acetic acid (100 ml) was stirred at 50° C. for 1.5 hours. After cooled to room temperature, the reaction mixture was adjusted to pH≈4.0 with 4N sodium hydroxide solution. The resulting precipitate was collected by filtration to give 5-[4-(N-benzyloxycarbonylamidino)phenoxy]valeric acid (14.87 g).

mp: ~103° C. (dec.)

IR (Nujol): 3300, 1735, 1640, 1600, 1560, 1510 cm$^{-1}$

NMR (DMSO-$d_6$, δ): 1.53–1.85 (4H, m), 2.29 (2H, t, J=7.2 Hz), 4.06 (2H, t, J=5.8 Hz), 5.16 (2H, s), 7.04 (2H, d, J=8.9 Hz), 7.3–7.5 (5H, m), 7.95 (2H, d, J=8.9 Hz), 9.54 (1H, br), 12.07 (1H, br)

MASS (M/Z): 370 (M$^+$)

The following compounds (Preparations 14 and 15) were obtained according to a similar manner to that of Preparation 13.

Preparation 14

4-[4-(N-Benzyloxycarbonylamidino)phenoxy]butyric acid mp: ~110° C. (dec.)

IR (Nujol): 3280, 1730, 1630, 1600, 1565, 1500 cm$^{-1}$

NMR (DMSO-$d_6$, δ): 1.83–2.14 (2H, m), 2.39 (2H, t, J=7.3 Hz), 4.06 (2H, t, J=6.4 Hz), 5.10 (2H, s), 7.01 (2H, d, J=8.9 Hz), 7.2–7.5 (5H, m), 7.98 (2H, d, J=8.9 Hz), 9.08 (1H, br s), 12.08 (1H, br s)

Preparation 15

6-[4-(N-Benzyloxycarbonylamidino)phenoxy]hexanoic acid mp: ~143° C. (dec.)

IR (Nujol): 1730, 1600, 1560 cm$^{-1}$

NMR (DMSO-$d_6$, δ): 1.3–1.8 (6H, m), 2.24 (2H, t, J=7 Hz), 4.03 (2H, t, J=6.4 Hz), 5.11 (2H, s), 7.0 (2H, d, J=8.9

Hz), 7.2–7.55 (5H, m), 7.98 (2H, d, J=8.9 Hz), 9.22 (1H, br), 12.02 (1H, br)

The formulae of the starting compounds and the object compounds in the following Examples are shown as follows.

| Compound | Formulae |
|---|---|
| starting compound (1) | HCl.H—Asp(OBzl)—Val—OBzl |
| object compound (1) | Am(Z)—C$_6$H$_4$—O(CH$_2$)$_4$CO—Asp(OBzl)—Val—OBzl |
| starting compound (2A) | Am(Z)—C$_6$H$_4$—O(CH$_2$)$_3$COOH |
| starting compound (2B) | HCl.H—Asp(OBzl)—Val—OBzl |
| object compound (2) | Am(Z)—C$_6$H$_4$—O(CH$_2$)$_3$CO—Asp(OBzl)—Val—OBzl |
| starting compound (3A) | Am(Z)—C$_6$H$_4$—O(CH$_2$)$_5$COOH |
| starting compound (3B) | HCl.H—Asp(OBzl)—Val—OBzl |
| object compound (3) | Am(Z)—C$_6$H$_4$—O(CH$_2$)$_5$CO—Asp(OBzl)—Val—OBzl |
| starting compound (4A) | Am(Z)—C$_6$H$_4$—OCH$_2$COOH |
| starting compound (4B) | HCl.H—Sar—Asp(OBzl)—Val—OBzl |
| object compound (4) | Am(Z)—C$_6$H$_4$—OCH$_2$CO—Sar—Asp(OBzl)—Val—OBzl |
| starting compound (5) | the same as object compound (1) |
| object compound (5) | Am—C$_6$H$_4$—O(CH$_2$)$_4$CO—Asp—Val—OH.CF$_3$COOH |
| starting compound (6) | the same as object compound (2) |
| object compound (6) | Am—C$_6$H$_4$—O(CH$_2$)$_3$CO—Asp—Val—OH.CF$_3$COOH |
| starting compound (7) | the same as object compound (3) |
| object compound (7) | Am—C$_6$H$_4$—O(CH$_2$)$_5$CO—Asp—Val—OH.CF$_3$COOH |
| starting compound (8) | the same as object compound (4) |
| object compound (8) | Am—C$_6$H$_4$—OCH$_2$CO—Sar—Asp—Val—OH.CF$_3$COOH |

| Compound | Formulae |
|---|---|
| starting compound (9A) | HCl.H—Sar—O$^t$Bu |
| starting compound (9B) | Am(Z)—⟨C$_6$H$_4$⟩—OCH$_2$CO—Sar—O$^t$Bu |
| starting compound (9C) | Am(Z)—⟨C$_6$H$_4$⟩—OCH$_2$CO—Sar—OH |
| starting compound (9D) | HCl.H—Asp(OBzl)—Leu—OBzl |
| object compound (9A) | Am(Z)—⟨C$_6$H$_4$⟩—OCH$_2$CO—Sar—Asp(OBzl)—Leu—OBzl |
| object compound (9B) | Am—⟨C$_6$H$_4$⟩—OCH$_2$CO—Sar—Asp—Leu—OH.CF$_3$COOH |
| object compound (10) | Am—⟨C$_6$H$_4$⟩—O(CH$_2$)$_3$CO—Asp—Val—OH.HCl |
| object compound (11) | Am—⟨C$_6$H$_4$⟩—O(CH$_2$)$_5$CO—Asp—Val—OH.HCl |
| object compound (12) | Am—⟨C$_6$H$_4$⟩—OCH$_2$CO—Sar—Asp—Val—OH.HCl |

In the above-mentioned formulae, Am(Z) means N-benzyloxycarbonylamidino, Am means amidino, Asp means L-aspartic acid, Val means L-valine, Sar means sarcosine, Leu means L-leucine, Bzl means benzyl and tBu means t-butyl.

EXAMPLE 1

To a mixture of 5-[4-(N-benzyloxycarbonylamidino)phenoxy]valeric acid (0.5 g ), the starting compound (1) (0.61 g) and 1-hydroxy-1H-benzotriazole (0.21 g) in N,N-dimethylformamide (5 ml ) was added 1-(3-dimethylaminopropyl)-3-ethylcarbodiimide (0.25 ml), and stirred at room temperature for 2 hours. The reaction mixture was poured into a mixture of water (50 ml) and ethyl acetate (30 ml), and was adjusted to pH≈9.5 with 4N sodium hydroxide solution. The separated organic layer was washed with saturated sodium hydrogen carbonate, water and aqueous solution of sodium chloride, and dried over magnesium sulfate. After filtration, the filtrate was evaporated in vacuo to give the object compound (1) (1.08 g) as an oil.

NMR (DMSO-d$_6$, δ): 0.83 (6H, d, J=6.7 Hz), 1.53–1.8 (4H, m), 2.16 (2H, m), 2.5–2.85 (2H, m), 4.01 (2H, t like), 4.15–4.28 (1H, m), 4.69–4.87 (1H, m), 5.0–5.23 (7H, m), 6.99 (2H, d, J=8.9 Hz), 7.2–7.5 (15H, m), 7.98 (2H, d, J=8.9 Hz), 8.15 (1H, d, J=8.2 Hz), 8.25 (1H, d, J=8.1 Hz), 9.1 (1H, br)

EXAMPLE 2

The object compound (2) was obtained from the starting compound (2A) and the starting compound (2B) according to a similar manner to that of Example 1.

NMR (DMSO-d$_6$, δ): 0.84 (6H, d, J=6.7 Hz), 1.8–2.2 (3H, m), 2.25 (2H, t like), 2.5–2.9 (2H, m), 4.01 (2H, t like), 4.20 (1H, m), 4.76 (1H, m), 5.0–5.2 (1H, m), 5.07 (2H, s), 5.10 (2H, s), 5.11 (2H, s), 6.99 (2H, d, J=8.9 Hz), 7.24–7.53 (15H, m), 7.98 (2H, d, J=8.9 Hz), 8.16 (1H, d, J=8 Hz), 8.30 (1H, d, J=7.9 Hz), 9.11 (1H, br)

EXAMPLE 3

The object compound (3) was obtained from the starting compound (3A) and the starting compound (3B) according to a similar manner to that of Example 1.

IR (Film): 3300, 1730, 1650, 1600 cm$^{-1}$

NMR (DMSO-d$_6$, δ): 0.83 (6H, d, J=6.7 Hz), 1.3–1.8 (6H, m), 1.9–2.2 (3H, m), 2.5–2.9 (2H, m), 4.01 (2H, t like) 4.13–4.25 (1H, m), 4.66–4.83 (1H, m), 5.0–5.15 (2H, m), 6.98 (2H, d, J=8.9 Hz), 7.2–7.52 (15H, m), 7.98 (2H, d, J=8.9 Hz), 8.05–8.3 (2H, m), 9.1 (1H, br)

EXAMPLE 4

The object compound (4) was obtained from the starting compound (4A) and the starting compound (4B) according to a similar manner to that of Example 1.

mp: 45°–50° C.

IR (Nujol): 3200 (br), 1640, 1600 cm$^{-1}$

NMR (DMSO-d$_6$, δ): 1.84 (6H, d, J=6.7 Hz), 2.05 (1H, m), 2.6–2.9 (4H, m), 2.78 and 2.97 (3H, each singlet), 3.96 and 4.03 (2H, each singlet), 4.18 (1H, m), 4.84 (1H, br s), 5.0–5.1 (8H, m), 6.99 (2H, d, J=8.9 Hz), 7.2–7.5 (15H, m), 7.96 (2H, d, J=8.9 Hz), 8.13 and 8.60 (1H, each doublet, J=8.0 Hz), 8.34 (1H m) 9 11 (2H br s) J=7.9 Hz

EXAMPLE 5

A mixture of the starting compound (5) (1 g) and 10% Pd-C (0.6 g) in a mixture of 1N hydrochloric acid (5 ml) and tetrahydrofuran (10 ml) was stirred under $H_2$ gas at room temperature for 6 hours.

After filtration, the filtrate was evaporated in vacuo. The resulting matter was subjected to preparative HPLC to give the object compound (5) (0.374 g).

HPLC condition

Column: YMC-PACK R-ODS-15 S-15 120A ODS 50φ× 250 mm elution: $CH_3CN$: 0.1% trifluoroacetic acid aqueous solution =1:4 flow: 118 ml/minute retention time: 8 minutes mp: ~147° C. (dec.)

IR (Nujol): 3300, 3080, 1660, 1600, 1530 $cm^{-1}$

NMR (DMSO-$d_6$, δ): 0.84 (6H, d, J=6.7 Hz), 1.54–1.84 (4H, m), 2.03 (1H, m), 2.19 (2H, t like), 2.36–2.78 (2H, m), 3.97–4.2 (3H, m), 4.65 (1H, m), 7.15 (2H, d, J=8.9 Hz), 7.76 (1H, d, J=7.9 Hz), 7.81 (2H, d, J=8.9 Hz), 8.25 (1H, d, J=7.8 Hz), 9.05 (2H, s), 9.14 (2H, s)

MASS (M/Z): 451 (M+1 free)

EXAMPLE 6

The object compound (6) was obtained from the starting compound (6) according to a similar manner to that of Example 5.

HPLC condition

Column: YMC-PACK R-ODS-15 S-15 120A ODS 50φ× 250 mm elution: $CH_3CN$: 0.1% trifluoroacetic acid aqueous solution=17:83 flow: 118 ml/minute retention time: 7.355 minutes mp: ~195° C. (dec.)

IR (Nujol): 3320, 3100, 1665, 1610, 1540, 1490 $cm^{-1}$

NMR (DMSO-$d_{6,δ}$): 0.84 (6H, d, J=6.7 Hz), 1.8–2.16 (3H, m), 2.3 (2H, t, J=7.3 Hz), 2.3–2.8 (2H, m), 3.98–4.2 (3H, m), 4.65 (1H, m), 7.14 (2H, d, J=8.9 Hz), 7.79 (1H, d, J=8.5 Hz), 7.82 (2H, d, J=8.9 Hz), 8.30 (1H, d, J=7.7 Hz), 9.03 (2H, s), 9.14 (2H, s)

EXAMPLE 7

The object compound (7) was obtained from the starting compound (7) according to a similar manner to that of Example 5.

HPLC condition

Column: YMC-PACK R-ODS-15 S-15 120A ODS 50φ×250 mm elution: $CH_3CN$: 0.1% trifluoroacetic acid aqueous solution=1.1:4.4 flow 118 ml/minute retention time 9.784 minutes mp: ~190° C. (dec.)

IR (Nujol): 3320, 3100, 1670, 1610, 1540, 1490 $cm^{-1}$

NMR (DMSO-$d_6$, δ): 0.84 (6H, d, J=5.7 Hz), 1.3–1.85 (6H, m), 1.93–2.25 (3H, m), 2.36–2.79 (2H, m), 3.97–4.21 (3H, m), 4.5–4.76 (1H, m), 7.14 (2H, d, J=8.9 Hz), 7.72 (1H, d, J=8.6 Hz), 7.81 (2H, d, J=8.9 Hz), 8.23 (1H, d, J=7.8 Hz), 9.0 (2H, s), 9.14 (2H, s)

MASS (M/Z): 465 (M+1 free)

EXAMPLE 8

The object compound (8) was obtained from the starting compound (8) according to a similar manner to that of Example 5.

HPLC condition elution: $CH_3CN$: 0.1% trifluoroacetic acid aqueous solution=15:85 retention time: 8.0 minutes (column and flow were the same as those of Example 5)

mp: 62°–68° C.

IR (Nujol): 3200 (br), 1640 $cm^{-1}$

NMR (DMSO-$d_6$, δ): 0.86 (6H, d, J=6.8 Hz), 2.04 (1H, m), 2.4–2.8 (2H, m), 2.80 and 3.00 (3H, each singlet), 3.8–4.2 (3H, m), 4.68 (1H, m), 4.94 and 5.05 (2H, each singlet), 7.13 (2H, d, J=8.9 Hz), 7.98 (2H, d, J=8.9 Hz), 7.9 and 8.00 (1H, each d, J=7.0, 8.5 Hz), 8.30 and 8.59 (1H, each d, J=8.0, 7.9 Hz), 9.03 (2H, s), 9.13 (2H, s)

EXAMPLE 9

(1) The starting compound (9B) was obtained from 2-[4-(N-benzyloxycarbonylamidino)phenoxy]acetic acid and the starting compound (9A) according to a similar manner to that of Example 1.

A mixture of the starting compound (9B) thus obtained, anisole (20 ml) and trifluoroacetic acid (80 ml) was stirred at room temperature for 2 hours and 45 minutes.

Trifluoroacetic acid was removed under reduced pressure, and the residue was triturated with diethyl ether to give the starting compound (9C) (19.49 g).

mp: 152°–156° C.

IR (Nujol): 1630, 1600, 1560, 1500 $cm^{-1}$

NMR (DMSO-$d_6$, δ): 2.84 and 3.06 (3H, each s), 4.01 and 4.19 (2H, each s), 4.91 and 5.09 (2H, each s), 5.34 (2H, s), 7.06 and 7.08 (2H, each d, J=8.8 Hz), 7.3–7.6 (5H, m), 7.78 (2H, d, J=8.8 Hz)

(2) The object compound (9A) was obtained from the starting compound (9C) thus obtained and the starting compound (9D) according to a similar manner to that of Example 1.

The protective groups of the object compound (9A) were removed according to a similar manner to that of Example 5 to give the object compound (9B).

mp: 41°–45° C.

IR (Nujol): 3250, 1630, 1610 $cm^{-1}$

NMR (DMSO-$d_6$, δ): 0.7–1.0 (6H, m), 1.3–1.7 (3H, m), 2.3–2.8 (2H, m), 2.80 and 3.00 (3H, each s), 3.97 and 4.04 (2H, each s), 4.18 (1H, m), 4.67 (1H, m), 5.93 and 5.05 (2H, each s), 7.13 (2H, d, J=8.7 Hz), 7.77 (2H, d, J=8.7 Hz), 7.98 and 8.17 (1H, each d, J=7.9 Hz), 8.24 and 8.55 (1H, each d, J=7.9 Hz), 8.95 and 9.13 (4H, each s)

MASS (M/Z): 494 ($M^++1$)

HPLC condition elution: $CH_3CN$: 0.1% trifluoroacetic acid aqueous solution=17:83 retention time: 11.0 minutes (column and flow were the same as those of Example 5)

The following compounds (Examples 10 to 12) were obtained from the corresponding trifluoroacetic acid salts according to the conventional manner.

EXAMPLE 10

The object compound (10)

IR (Nujol): 3420, 3270, 1690, 1635, 1600, 1540, 1480 cm$^{-1}$

NMR (DMSO-d$_6$, δ): 0.84 (6H, d, J=6.3 Hz), 1.8–2.2 (3H, m), 2.3 (2H, t, J=7.3 Hz), 2.3–2.8 (2H, m), 3.96–4.2 (3H, m), 4.65 (1H, m), 7.14 (2H, d, J=8.9 Hz), 7.8 (1H, d, J=8.5 Hz), 7.85 (2H, d, J=8.9 Hz), 8.35 (1H, d, J=7.7 Hz), 9.04 (2H, s), 9.24 (2H, s), 12.51 (1H, brs)

Elemental Analysis calcd. for C$_{20}$H$_{28}$N$_4$O$_7$.HCl.H$_2$O

| Elemental Analysis calcd. for C$_{20}$H$_{28}$N$_4$O$_7$.HCl.H$_2$O | |
|---|---|
| | C: 48.93, H: 6.36, N: 11.41, Cl: 7.22 |
| found | C: 48.77, H: 6.52, N: 11.22, Cl: 6.98 | mp: 198° C. (dec)

EXAMPLE 11

The object compound (11)

mp: 163° C. (dec)

IR (Nujol): 3270, 1700, 1665, 1630, 1605, 1535, 1480 cm$^{-1}$

NMR (DMSO-d$_6$, δ): 0.84 (6H, d, J=6.1 Hz), 1.29–1.85 (6H, m), 1.91–2.23 (3H, m), 2.35–2.78 (2H, m), 3.98–4.2 (3H, m), 4.55–4.73 (1H, m), 7.14 (2H, d, J=8.9 Hz), 7.72 (1H, d, J=8.7 Hz), 7.83 (2H, d, J=8.9 Hz), 8.25 (1H, d, J=7.7 Hz), 8.94 (2H, s), 9.20 (2H, s)

EXAMPLE 12

The object compound (12)

mp: 133°–140° C.

IR (Nujol): 3000–3300 (brs), 1710 (shoulder), 1630 (brs) cm$^{-1}$

NMR (DMSO-d$_6$, δ): 0.86 (6H, d, J=6.8 Hz), 2.05 (1H, m), 2.80 and 3.01 (3H, each s), 2.4–2.8 (2H, m), 3.8–4.2 (3H, m), 4.68 (1H, m), 4.94 and 5.06 (2H, each s), 7.13 (2H, d, J=8.8 Hz), 7.80 (2H, d, J=8.8 Hz), 7.8 and 8.0 (1H, each d, J=7.0 Hz and 8.5 Hz), 8.37 and 8.68 (1H, each d, J=8.0 Hz and 7.9 Hz), 9.05 (2H, s), 9.24 (2H, s)

MASS (M/Z): 480 (M$^+$+1)

HPLC condition

Column: YMC-PACK R-ODS-15 S-15 120A ODS 50φ× 250 mm elution: CH$_3$CN: 0.1% trifluoroacetic acid aqueous solution=15:85 flow: 1 ml/minute retention time: 8.1 minutes

The formulae of the starting compound and the object compound in the following Example 13 are shown as follows.

| starting compound (13) | 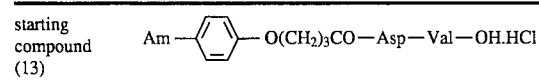 |
| object compound (13) | 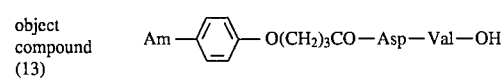 |

(Am, Asp and Val are each as explained before)

EXAMPLE 13

A solution of the starting compound (13) (79 g) in 0.02M pyridine-acetic acid buffer (PH=5) (1 l) was subjected to a column chromatography on ion exchange resin (2 l) eluting with 0.5M pyridine-acetic acid buffer (PH=5).

The fractions containing the object compound were combined and concentrated under reduced pressure to give the object compound (13) (62.54 g).

mp: 171° C. (dec)

IR (Nujol): 3310, 1650, 1600, 1520 cm$^{-1}$

NMR (DMSO-d$_6$, δ): 0.80 (6H, d, J=6.8 Hz), 1.8–2.73 (7H, m), 3.8–4.25 (3H, m), 4.56 (1H, m), 7.10 (2H, d, J=8.8 Hz), 7.44 (1H, d, J=8.1 Hz), 7.74 (2H, d, J=8.7 Hz), 8.39 (1H, d, J=7.6 Hz), 8.75 (1.5H, s), 11.25 (1.5H, s)

MASS (M/Z): 437 (M$^+$+1)

Analysis for C$_{20}$H$_{28}$N$_4$O$_7$1.2H$_2$O

| | C | H | N |
|---|---|---|---|
| Calcd. | 52.44 | 6.68 | 12.23 |
| Found | 52.43 | 6.82 | 12.00 |

Preparation 16

A mixture of DL-4-cyano-N-acetylphenylalanine (114.0 g), cobalt chloride(II) (0.63 g) and acylase Amano 15000 (Trademark) (6.27 g) in 1N sodium hydroxide aqueous solution (492 ml) was adjusted to pH=7.5 with 0.1N hydrochloric acid and 0.1N sodium chloride aqueous solution, and then was stirred at 33°–36° C. for 20 hours. The reaction mixture was adjusted to pH=1 with 10% hydrochloric acid, and was washed with ethyl acetate, and the resulting precipitate was collected by filtration. The precipitate was washed with 10% hydrochloric acid and water to give 4-cyano-N-acetyl-D-phenylalanine (32.00 g).

mp: 173°–175° C.

[α]$_D$ (C=1, MeOH)=−12.9°

IR (Nujol): 2210, 1715, 1600, 1520 cm$^{-1}$

NMR (DMSO-d$_6$, δ): 1.78 (3H, s), 2.92 (1H, dd, J=13.8 Hz, J=9.8 Hz), 3.15 (1H, dd, J=13.8 Hz, J=4.9 Hz), 4.48 (1H, m), 7.44 (2H, d, J=8.2 Hz), 7.76 (2H, d, J=8.2 Hz), 8.25 (1H, d, J=8.2 Hz)

The acidic aqueous layer was adjusted to pH=7.5 with 4N sodium hydroxide aqueous solution, and triethylamine (32.2 ml) and di-t-butyldicarbonate (83.59 g) was added, and stirred at room temperature for 5 days. The reaction mixture was adjusted to pH=0.6 with 10% hydrochloric acid and extracted with ethyl acetate. The separated organic layer was washed with water and brine, and dried over magnesium sulfate. After evaporation in vacuo, the resulting precipitate was washed with n-hexane, to give 4-cyano-N-t-butoxycarbonyl-L-phenylalanine (43.50 g).

mp: 149°–150° C.

[α]$_D$ (C=1, MeOH)=+6.1°

IR (Nujol): 3350, 3180, 2240, 1730, 1680, 1600, 1505 cm$^{-1}$

NMR (DMSO-d$_6$, δ): 1.31 (9H, s), 2.91 (1H, dd, J=13.7 Hz, J=10.9 Hz), 3.14 (1H, dd, J=13.7 Hz, J=10.9 Hz), 4.18 (1H, m ), 7.20 (1H, d, J=8.6 Hz), 7.46 (2H, d, J=8.1 Hz), 7.7 6 (2H, d, J=8.1 Hz)

Analysis Found: C 62.38, H 6.32, N 9.55 Calcd.: C 62.05, H 6.24, N 9.24

Preparation 17

Through a solution of 4-cyano-N-t-butoxycarbonyl-L-phenylalanine (31.50 g) in pyridine (400 ml) and triethylamine (190 ml), hydrogen sulfide was bubbled at room temperature for 2 hours, and was allowed to stand at room temperature overnight. The reaction mixture was diluted with water and ethyl acetate, and was adjusted to pH=4.5 with conc. hydrochloric acid, and extracted with ethyl acetate. The separated organic layer was washed with dil. hydrochloric acid and water, and dried over magnesium sulfate. After evaporation in vacuo, the resulting precipitate was collected by filtration, and washed with n-hexane to give 4-thiocarbamoyl-N-t-butoxycarbonyl-L-phenylalanine (30.31 g).

mp: 254°–256° C. (decomp.)

$[\alpha]_D$ (MeOH, C=1)=+29.40°

IR (Nujol): 3280, 3110, 1670, 1605, 1510 cm$^{-1}$

NMR (DMSO-d$_6$, δ): 1.32 (9H, s), 2.87 (1H, dd, J=13.7 Hz, J=10.3 Hz), 3.05 (1H, dd, J=13.7 Hz, J=4.5 Hz), 4.12 (1H, m), 7.15 (1H, d, J=8.4 Hz), 7.28 (2H, d, J=8.2 Hz), 7.83 (2H, d, J=8.2 Hz), 9.43 (1H, br s), 9.80 (1H, br s)

Analysis Found: C 55.19, H 6.32, N 8.38, S 9.99 Calcd.: C 55.53, H 6.21, N 8.63, S 9.88

Preparation 18

A solution of 4-thiocarbamoyl-N-t-butoxycarbonyl-L-phenylalanine (30.06 g) and methyl iodide (63.5 ml) in acetone (300 ml) was stirred and refluxed for 40 minutes, and the solvent was removed in vacuo. The resulting matter was dissolved in methanol (300 ml), and ammonium acetate (10.71 g) was added, and then the mixture was refluxed with stirring for 4 hours and 30 minutes. The reaction mixture was cooled and the resulting precipitate was filtered off. The filtrate was evaporated in vacuo and the resulting matter was triturated with ethanol and diethyl ether and washed with diethyl ether, to give 4-amidino-N-t-butoxycarbonyl-L-phenylalanine hydroiodide (13.83 g).

mp: 184°–188° C. (decomp.)

IR (Nujol): 1670, 1600, 1560 cm$^{-1}$

NMR (DMSO-d$_6$, δ): 1.33 (9H, s), 2.7–3.2 (2H, m), 3.97 (1H, m), 7.23 (2H, d, J=8.0 Hz), 7.4–8.0 (6H, m)

Mass (m/z): 308 (M$^+$+1)

Preparation 19

To a mixture of 4-amidino-N-t-butoxycarbonyl-L-phenylalanine hydroiodide (1.00 g), 4N sodium hydroxide aqueous solution (1.15 ml), tetrahydrofuran (2 ml), and water (10 ml), a solution of benzyloxycarbonyl chloride in tetrahydrofuran (2 ml) was added, being adjusted to pH=12~12.5 with 4N sodium hydroxide aqueous solution. The reaction mixture was diluted with water and diethyl ether, and the separated aqueous layer was neutralized with 10% hydrochloric acid and extracted with ethyl acetate, and washed with water and brine, and dried over magnesium sulfate. After evaporation in vacuo, the resulting precipitate was collected by filtration and washed with diethyl ether to give 4-(N-benzyloxycarbonylamidino)-N-t-butoxycarbonyl-L-phenylalanine (0.53 g).

mp: 112°–115° C.

IR (Nujol): 3300, 1680, 1620, 1560, 1500 cm$^{-1}$

NMR (DMSO-d$_6$, δ): 1.31 (9H, s), 2.8–3.2 (2H, m), 4.12 (1H, m), 5.11 (1H, s), 7.12 (1H, d, J=8.3 Hz), 7.3–7.5 (7H, m), 7.91 (2H, d, J=8.0 Hz), 9.14 (2H, br s)

Preparation 20

4-(N-Benzyloxycarbonylamidino)-N-acetyl-D-phenylalanine was obtained from 4-cyano-N-acetyl-D-phenylalanine according to the similar manners to those of Preparations 17, 18 and 19.

mp: 140°–145° C. (decomp.)

IR (Nujol): 3250 (br s), 1740, 1605 cm$^{-1}$

NMR (DMSO-d$_6$, δ): 1.77 (3H, s), 2.90 (1H, dd, J=13.8 Hz, J=10.0 Hz), 3.16 (1H, dd, J=13.8 Hz, J=4.5 Hz), 4.46 (1H, m), 5.27 (1H, s), 7.2–7.5 (7H, m), 7.80 (2H, d, J=8.2 Hz), 8.32 (1H, d, J=8.2 Hz)

Preparation 21

A mixture of ethyl 5-(4-amidinophenyl)-2,4-pentadienoate hydrochloride (20.00 g) and 10% Pd-C (5.00 g) in ethanol (500 ml) was stirred under H$_2$ gas at room temperature for 3 hours. After filtration, the filtrate was evaporated in vacuo. The resulting precipitate was washed with diethyl ether to give ethyl 5-(4-amidinophenyl)pentanoate hydrochloride (19.42 g).

IR (Nujol): 3400, 3100, 1730, 1660 cm$^{-1}$

NMR (DMSO-d$_6$, δ): 1.16 (3H, t, J=7.1 Hz), 1.52–1.61 (4H, m), 2.32 (2H, t, J=6.9 Hz), 2.66 (2H, t, J=7.0 Hz), 4.04 (2H, q, J=7.1 Hz), 7.45 (2H, d, J=8.3 Hz), 7.78 (2H, d, J=8.3 Hz), 9.21 (2H, s), 9.26 (2H, s)

MASS (m/z): 248 (M$^+$)

Preparation 22

Ethyl 3-(4-amidinophenyl)propionate hydrochloride was obtained according to a similar manner to that of preparation 21.

IR (Nujol): 3350, 3150, 1720, 1670, 1210 cm$^{-1}$

NMR (DMSO-d$_6$, δ): 1.16 (3H, t, J=7.1 Hz), 2.69 (2H, t, J=7.4 Hz), 2.95 (2H, t, J=7.4 Hz), 4.09 (2H, q, J=7.1 Hz), 7.48 (2H, d, J=8.3 Hz), 7.82 (2H, d, J=8.3 Hz), 8.94 (4H, br s)

MASS (m/z): 220 (M$^+$)

The following compounds (preparations 23 to 25) were obtained according to a similar manner to that of Preparation 10.

Preparation 23

Ethyl 3-[4-(N-benzyloxycarbonylamidino)phenyl]-propionate

NMR (DMSO-d$_6$, δ): 1.15 (3H, t, J=7.1 Hz), 2.65 (2H, t, J=7.4 Hz), 2.91 (2H, t, J=7.4 Hz), 4.03 (2H, q, J=7.1 Hz), 5.10 (2H, s), 7.31–7.41 (7H, m), 7.90 (2H, d, J=8.3 Hz), 9.13 (2H, br s)

MASS (m/z): 354 (M$^+$)

Preparation 24

Ethyl 5-[4-(N-benzyloxycarbonylamidino)phenyl]-pentanoate

IR (Nujol): 3450, 3300, 1730, 1600, 1250 cm$^{-1}$

NMR (DMSO-d$_6$, δ): 1.16 (3H, t, J=7.1 Hz), 1.56–1.58 (4H, m), 2.31 (2H, t, J=6.9 Hz), 2.64 (2H, t, J=7.0 Hz), 4.03 (2H, q, J=7.1 Hz), 5.11 (2H, s), 7.23–7.40 (7H, m), 7.90 (2H, d, J=8.3 Hz), 9.23 (2H, br s)

Preparation 25

Ethyl 8-[4-(N-benzyloxycarbonylamidino)phenoxy]-octanoate mp: 93°–95° C.

IR (Nujol): 3420, 3290, 1720, 1650, 1590, 1560, 1480 cm$^{-1}$

NMR (DMSO-d$_{6, δ}$): 1.17 (3H, t, J=7.1 Hz), 1.15–1.83 (10H, m), 2.27 (2H, t, J=7.2 Hz), 4.01 (2H, t like), 4.04 (2H, q, J=7.1 Hz), 5.10 (2H, s), 7.0 (2H, d, J=8.9 Hz), 7.36 (5H, m), 7.98 (2H, d, J=8.9 Hz), 9.09 (2H, br s)

Preparation 26

Ethyl 5-[4-(N-benzyloxycarbonylamidinophenyl)]pentanoate (22.00 g) in conc. hydrochloric acid (220 ml) was stirred at room temperature for 3 hours. The reaction mixture was filtrated and the filtrated precipitate was solved with the mixture of water and ethyl acetate, and adjusted to pH=10.50 with aqueous solution of sodium hydroxide, and separated aqueous layer was adjusted to pH=4.50 with 10% hydrochloric acid, and extracted with ethyl acetate, and separated organic layer was washed with brine and dried over magnesium sulfate. After filtration, the filtrate was evaporated in vacuo, and the resulting precipitate was triturated with diisopropyl ether to give 5-[4-(N-benzyloxycarbonylamidinophenyl)]pentanoic acid (12.00 g).

IR (Nujol): 3350, 3200, 1700, 1660, 1620, 1250 cm$^{-1}$

NMR (DMSO-d$_6$, δ): 1.50–1.60 (4H, m), 2.23 (2H, t, J=6.9 Hz), 2.64 (2H, t, J=7.0 Hz), 5.10 (2H, s), 7.27–7.42

(7H, m), 7.90 (2H, d, J=8.3 Hz), 9.11 (2H, br s), 12.01 (1H, br s)

MASS (m/z): 355 (M$^+$+1)

Preparation 27

3-[4-(N-Benzyloxycarbonylamidino)phenyl]propionic acid was obtained according to a similar manner to that of Preparation 26.

NMR (DMSO-d$_6$, δ): 2.56 (2H, t, J=7.4 Hz), 2.88 (2H, t, J=7.4 Hz), 5.10 (2H, s), 7.32–7.38 (8H, m), 7.90 (2H, d, J=8.3 Hz), 9.08 (1H, br s)

Preparation 28

8-[4-(N-Benzyloxycarbonylamidino)phenoxy]octanoic acid was obtained according to a similar manner to that of Preparation 93.

mp: 130° C. (dec.)

IR (Nujol): 1760, 1700, 1600 cm$^{-1}$

NMR (DMSO-d$_6$, δ): 1.15–1.8 (10H, m), 2.20 (2H, t, J=7.2 Hz), 4.07 (2H, t, J=6.4 Hz), 5.27 (2H, s), 7.09 (2H, d, J=8.9 Hz), 7.4 (5H, m), 7.88 (2H, d, J=8.9 Hz), 10.0 (1H, br), 12.0 (1H, br)

Preparation 29

A mixture of ethyl 4-(4-cyanophenoxy)butyrate (4.7 g) in tetrahydrofuran (23.5 ml) and 1N sodium hydroxide solution (40.2 ml) was refluxed for 2 hours under stirring. The reaction mixture was adjusted to pH≈2.0 with 10% hydrochloric acid, and the resulting precipitate was collected by filtration to give 4-(4-cyanophenoxy)butyric acid (4.06 g).

mp: 210° C.

IR (Nujol): 3175, 2220, 1730, 1600, 1510 cm$^{-1}$

NMR (DMSO-d$_6$, δ): 1.96 (2H, m), 2.39 (2H, m), 4.08 (2H, m), 7.08 (2H, d, J=8.9 Hz), 7.76 (2H, d, J=8.9 Hz), 12.18 (1H, s)

Preparation 30

5-(4-Cyanophenoxy)pentanoic acid was obtained according to a similar manner to that of Preparation 29.

mp: 160° C.

IR (Nujol): 3200, 2225, 1720, 1600, 1560, 1505 cm$^{-1}$

NMR (DMSO-d$_6$, δ): 1.5–1.85 (4H, m), 2.29 (2H, t like), 4.05 (2H, m), 7.09 (2H, d, J=6.9 Hz), 7.76 (2H, d, J=6.9 Hz)

Preparation 31

A mixture of 4-(4-cyanophenoxy)butyric acid (1 g), triethylamine (0.75 ml) and diphenylphosphoryl azide (1.16 ml) in tetrahydrofuran (10 ml) was refluxed for 6 hours under stirring. To the resultant mixture was added the starting compound (P-31) (2.4 g) at room temperature and the mixture was stirred at the same condition for 15 hours. The reaction mixture was poured into a mixture of ethyl acetate (30 ml) and water (100 ml) and adjusted to pH≈10 with 4N-sodium hydroxide solution. The separated organic layer was washed with diluted hydrochloric acid, saturated sodium bicarbonate aqueous solution, water, and brine, and dried over magnesium sulfate, and evaporated in vacuo to give the object compound (P-31) (1.7 g).

mp: 106°–109° C.

IR (Nujol): 3360, 3300, 3270, 2225, 1725, 1630, 1600 cm$^{-1}$

NMR (DMSO-d$_6$, δ): 0.82 (6H, d, J=5.6 Hz), 1.83 (2H, t, J=6.3 Hz), 2.05 (1H, m), 2.4–2.8 (2H, m), 3.15 (2H, m), 4.05 (2H, t, J=6.2 Hz), 4.23 (1H, m), 4.61 (1H, m), 5.05 (2H, s), 5.10 (2H, s), 6.22–6.4(2H, m), 7.08 (2H, d, J=8.9 Hz), 7.35 (10H, m), 7.75 (2H, d, J=8.9 Hz), 8.15 (1H, d, J=8.3 Hz)

FAB-MASS: 615 (M$^+$+1)

Preparation 32

The object compound (P-32) was obtained according to a similar manner to that of preparation 31.

mp: 115°–122° C.

IR (Nujol): 3300, 2220, 1730, 1625, 1600, 1540 cm$^{-1}$

NMR (DMSO-d$_6$, δ): 0.83 (6H, d, J=6.7 Hz), 1.52 (2H, m), 1.69 (2H, m), 2.06 (1H, m), 2.5–2.8 (2H, m), 3.05 (2H, m), 4.05 (2H, t, J=6.2 Hz), 4.23 (1H, m), 4.63 (1H, m), 5.06 (2H, s), 5.11 (2H, s), 6.2–6.4 (2H, m), 7.08 (2H, d, J=8.9 Hz), 7.35 (10H, m), 7.74 (2H, d, J=8.9 Hz), 8.16 (1H, d, J=8.3 Hz)

The following compounds (Preparations 33 and 34) were obtained according to a similar manner to that of Preparation 17.

Preparation 33

The object compound (P-33)

mp: 139° C.

IR (Nujol): 3430, 3320, 3200, 1730, 1715, 1630, 1540 cm$^{-1}$

NMR (DMSO-d$_6$, δ): 0.83 (6H, d, J=6.5 Hz), 1.83 (2H, t like), 2.05 (1H, m), 2.4–2.8 (2H, m), 3.15 (2H, m), 4.03 (2H, t like), 4.23 (1H, m), 4.62 (1H, m), 5.06 (2H, s), 5.11 (2H, s), 6.2–6.42 (2H, m), 6.93 (2H, d, J=8.8 Hz), 7.34 (10H, m), 7.95 (2H, d, J=8.8 Hz), 8.15 (1H, d, J=8.2 Hz), 9.32 (1H, s), 9.64 (1H, s)

Preparation 34

The object compound (P-34)

mp: ~130° C.

IR (Nujol):

NMR (DMSO-d$_6$, δ): 0.83 (6H, d, J=5.8 Hz), 1.52 (2H, m), 1.69 (2H, m ), 2.06 (1H, m), 2.4–2.8 (2H, m), 3.05 (2H, m), 4.01 (2H, t, J=6.0 Hz), 4.23 (1H, m), 4.62 (1H, m ), 5.06 (2H, s), 5.11 (2H, s), 6.2–6.4 (2H, m), 6.93 (2H, d, J=8.9 Hz), 7.35 (10H, m), 7.95 (2H, d, J=8.9 Hz), 8.15 (1H, d, J=8.3 Hz), 9.32 (1H, s), 9.64 (1H, s)

In the aforesaid Preparations 31 to 34, the formulae of the starting compound and the object compounds are shown in the following.

| Compound | Formula |
| --- | --- |
| starting compound (P-31) | HCl.H—Asp(OBzl)—Val—OBzl |
| object compound (P-31) | NC—⟨C$_6$H$_4$⟩—O(CH$_2$)$_3$NHCO—Asp(OBzl)—Val—OBzl |
| object compound (P-32) | NC—⟨C$_6$H$_4$⟩—O(CH$_2$)$_4$NHCO—Asp(OBzl)—Val—OBzl |

| Compound | Formula |
|---|---|
| object compound (P-33) | H₂N—C(=S)—C₆H₄—O(CH₂)₃NHCO—Asp(OBzl)—Val—OBzl |
| object compound (P-34) | H₂N—C(=S)—C₆H₄—O(CH₂)₄NHCO—Asp(OBzl)—Val—OBzl |

(In the above-mentioned formulae, Asp, Val and Bzl are each as explained before.)

Preparation 35

The mixture of 60% sodium hydride (7.92 g) in tetrahydrofuran (100 ml) was stirred at −10° C. under nitrogen gas. To reaction mixture was poured ethyl 5-diethoxyphosphoryl-3-pentenoate (49.61 g) and stirred for 1 hour at −10° C. To reaction mixture was poured p-cyanobenzaldehyde (20.00 g) in tetrahydrofuran (50 ml) and stirred for 3 hours at 0° C. The reaction mixture was poured into a mixture of brine and ethyl acetate. The separated organic layer was dried over magnesium sulfate and treated with activated charcoal. After filtration, the filtrate was evaporated in vacuo. The residue was subjected to column chromatography on silica gel and eluted with ethyl acetate/n-hexane=1:4. The fractions containing the object compound were combined and evaporated in vacuo, and give ethyl 5-(4-cyanophenyl)-2,4-pentadienoate (10.04 g).

IR (Nujol): 2250, 1720, 1630, 1250 cm$^{-1}$

NMR (DMSO-d$_6$, δ): 1.24 (3H, t, J=7.1 Hz), 4.16 (2H, q, J=7.1 Hz), 6.18 (1H, d, J=12.5 Hz), 7.13–7.49 (3H, m), 7.74 (2H, d, J=8.5 Hz), 7.85 (2H, d, J=8.5 Hz)

Mass (m/z): 22 (M$^+$)

The following compounds (preparations 36 and 37) were obtained according to a similar manner to that of Preparation 4.

Preparation 36

Ethyl 3-[4-{1-(ethoxy)iminomethyl}phenyl]acrylate hydrochloride

IR (Nujol): 1720, 1640, 1320, 1180 cm$^{-1}$

NMR (DMSO-d$_6$, δ): 1.28 (3H, t, J=7.1 Hz), 1.49 (3H, t, J=7.0 Hz), 4.21 (2H, q, J=7.1 Hz), 4.66 (2H, q, J=7.0 Hz), 6.86 (1H, d, J=16.0 Hz), 7.59 (1H, d, J=16.0 Hz), 7.79 (2H, d, J=8.7 Hz), 8.18 (2H, d, J=8.7 Hz)

Mass (m/z): 247 (M$^+$)

Preparation 37

Ethyl 5-[4-{1-(ethoxy)iminomethyl}phenyl]-2,4-pentadienoate hydrochloride

IR (Nujol): 3400, 1720, 1620, 1250 cm$^{-1}$

NMR (DMSO-d$_6$, δ): 1.25 (3H, t, J=7.1 Hz), 1.49 (3H, t, J=7.0 Hz), 4.16 (2H, q, J=7.1 Hz), 4.63 (2H, q, J=7.0 Hz), 6.20 (1H, d, J=14.2 Hz), 7.17–7.46 (3H, m), 7.84 (2H, d, J=8.5 Hz), 8.15 (2H, d, J=8.5 Hz)

Mass (m/z): 273 (M$^+$)

Preparation 38

To a mixture of ethyl 5-[4-{(1-ethoxy)iminomethyl}phenyl]-2,4-pentadienoate hydrochloride (22.00 g) in ethanol (220 ml) was poured 9N-ethanol solution of ammonia (19.7 ml) and refluxed for 15 hours. After cooled to room temperature, the reaction mixture was evaporated in vacuo, and the resulting precipitate was washed with diisopropyl ether to give ethyl 5-(4-amidinophenyl)-2,4-pentadienoate hydrochloride (20.15 g).

IR (Nujol): 3400, 1720, 1630, 1250 cm$^{-1}$

NMR (DMSO-d$_6$, δ): 1.25 (3H, t, J=7.1 Hz), 4.17 (2H, q, J=7.1 Hz), 6.18 (1H, d, J=14.4 Hz), 7.15–7.51 (3H, m), 7.78 (2H, d, J=8.5 Hz), 7.89 (2H, d, J=8.5 Hz), 9.30 (2H, s), 9.48 (2H, s)

Mass (m/z): 244 (M$^+$)

Preparation 39

Ethyl 3-(4-amidinophenyl)acrylate hydrochloride was obtained according to a similar manner to that of Preparation 7.

IR (Nujol): 3400, 1720, 1320, 1200 cm$^{-1}$

NMR (DMSO-d$_6$, δ): 1.28 (3H, t, J=7.1 Hz), 4.22 (2H, q, J=7.1 Hz), 6.86 (1H, d, J=16.1 Hz), 7.73 (1H, d, J=16.1 Hz), 7.91 (2H, d, J=8.5 Hz), 7.98 (2H, d, J=8.5 Hz), 8.76 (4H, br s)

Mass (m/z): 218 (M$^+$)

Preparation 40

3-[4-(N-Benzyloxycarbonylamidino)phenyl]propionic acid was obtained according to a similar manner to that of Preparation 26.

NMR (DMSO-d$_6$, δ): 2.56 (2H, t, J=7.4 Hz), 2.88 (2H, t, J=7.4 Hz), 5.10 (2H, s), 7.32–7.38 (8H, m), 7.90 (2H, d, J=8.3 Hz), 9.08 (1H, br s)

The formulae of the starting compounds and the object compounds in the following Examples are shown as follows.

| Compound | Formula |
|---|---|
| object compound (14) | Am(Z)—⟨C6H4⟩—(CH2)4CO—Asp(OBzl)—Val—OBzl |
| object compound (15) | Am(Z)—⟨C6H4⟩—O(CH2)4CO—Asp(OBzl)—Tyr—OMe |
| object compound (16) | Am(Z)—⟨C6H4⟩—O(CH2)4CO—Asp(OBzl)—Tyr(Me)—OMe |
| object compound (17) | Am(Z)—⟨C6H4⟩—O(CH2)4CO—Asp(OBzl)—Tyr(Me)—OBzl |
| object compound (18) | Am(Z)—⟨C6H4⟩—O(CH2)4CO—Asp(OBzl)—Ser(Bzl)—OBzl |
| object compound (19) | Am(Z)—⟨C6H4⟩—OCH2CO—Sar—Asp(OBzl)—Tyr(Me)—OMe |
| object compound (20) | Am(Z)—⟨C6H4⟩—OCH2CO—Sar—Asp(OBzl)—Tyr(Me)—OBzl |
| object compound (21-A) (SEQ ID NO: 1) | BocNH—CH(—CH2—⟨C6H4⟩—Am(Z))—CO—Sar—Asp(OBzl)—Val—OBzl |
| object compound (21-B) (SEQ ID NO: 1) | H2N—CH(—CH2—⟨C6H4⟩—Am(Z))—CO—Sar—Asp(OBzl)—Val—OBzl · HCl |
| starting compound (22) | HCl·H—Asp(OBzl)—Tyr(Bzl)—OBzl |
| object compound (22) | Am(Z)—⟨C6H4⟩—O(CH2)3CO—Asp(OBzl)—Tyr(Bzl)—OBzl |
| object compound (23) | Am(Z)—⟨C6H4⟩—O(CH2)3CO—Asp(OBzl)—Tyr(Me)—OBzl |
| object compound (24) | Am(Z)—⟨C6H4⟩—(CH2)4CO—Asp(OBzl)—Tyr(Me)—OBzl |
| object compound (25) | Am(Z)—⟨C6H4⟩—O(CH2)5CO—Asp(OBzl)—Tyr(Me)—OBzl |

-continued

| Compound | Formula |
|---|---|
| object compound (26) | Am(Z)—⟨C₆H₄⟩—(CH₂)₄CO—Asp(OBzl)—Leu—OBzl |
| object compound (27) | Am(Z)—⟨C₆H₄⟩—O(CH₂)₃CO—Asp(OBzl)—Gly—OBzl |
| object compound (28) | Am(Z)—⟨C₆H₄⟩—O(CH₂)₃CO—Asp(OBzl)—Ala—OBzl |
| object compound (29) | Am(Z)—⟨C₆H₄⟩—O(CH₂)₃CO—Asp(OBzl)—Phe—OBzl |
| object compound (30) | Am(Z)—⟨C₆H₄⟩—O(CH₂)₃CO—Asp(OBzl)—NH—CH(CH₂Ph)—CH₂—COOEt |
| object compound (31) | Am(Z)—⟨C₆H₄⟩—(CH₂)₄CO—Asp(OBzl)—NH—CH(CH₂-C₆H₁₁)—COOBzl |
| object compound (32) | Am(Z)—⟨C₆H₄⟩—O(CH₂)₃CO—Asp(OBzl)—NH—CH(Et)—COOBzl |
| object compound (33) | Am(Z)—⟨C₆H₄⟩—O(CH₂)₃CO—Asp(OBzl)—NH—CH(Pr)—COOBzl |
| object compound (34) | Am(Z)—⟨C₆H₄⟩—O(CH₂)₃CO—Asp(OBzl)—NH—CH(CH₂-C₆H₁₁)—COOBzl |
| object compound (35) | Am(Z)—⟨C₆H₄⟩—(CH₂)CO—Sar—Asp(OBzl)—Thr(Me)—OBzl |

-continued

| Compound | Formula |
|---|---|
| object compound (36) | Am(Z)—⬡—OCH₂CO—Sar—Asp(OBzl)—NH—CH(CH₂-cyclohexyl)—COOBzl |
| object compound (37) | the same as object compound (22) |
| object compound (37) | HCl.Am—⬡—O(CH₂)₃CO—Asp—Tyr—OH |
| object compound (38) | HCl.Am—⬡—O(CH₂)₃CO—Asp—Tyr(Me)—OH |
| object compound (39) | HCl.Am—⬡—O(CH₂)₅CO—Asp—Val—OH |
| object compound (40) | HCl.Am—⬡—(CH₂)₄CO—Asp—Val—OH |
| object compound (41) | HCl.Am—⬡—OCH₂CO—Sar—Asp—Tyr(Me)—OH |
| object compound (42) | Am—⬡—O(CH₂)₅CO—Asp—Tyr(Me)—OH .CF₃COOH |
| object compound (43) | Am—⬡—(CH₂)₄CO—Asp—Tyr(Me)—OH .CF₃COOH |
| object compound (44) | Am—⬡—O(CH₂)₄CO—Asp—Tyr—OMe .CF₃COOH |
| object compound (45) | Am—⬡—OCH₂)₄CO—Asp—Tyr(Me)—OMe .CF₃COOH |
| object compound (46) | Am—⬡—O(CH₂)₄CO—Asp—Tyr(Me)—OH |
| object compound (47) | Am—⬡—O(CH₂)₃CO—Asp—Gly—OH .CF₃COOH |
| object compound (48) | Am—⬡—O(CH₂)₃CO—Asp—Ala—OH .CF₃COOH |

-continued

| Compound | Formula |
|---|---|
| object compound (49) | Am—⟨C6H4⟩—O(CH2)4CO—Asp—Ser—OH · CF3COOH |
| object compound (50) | Am—⟨C6H4⟩—O(CH2)3CO—Asp—Phe—OH · CF3COOH |
| object compound (51) | Am—⟨C6H4⟩—(CH2)4CO—Asp—Leu—OH · CF3COOH |
| object compound (52) | Am—⟨C6H4⟩—O(CH2)3CO—Asp—NH—CH(CH2CH2CH3)—COOH · CF3COOH |
| object compound (53) | Am—⟨C6H4⟩—O(CH2)3CO—Asp—NH—CH(CH2-cyclohexyl)—COOH · CF3COOH |
| object compound (54) | Am—⟨C6H4⟩—O(CH2)3CO—Asp—NH—CH(CH2Ph)—CH2COOH · CF3COOH |
| object compound (55) | Am—⟨C6H4⟩—(CH2)4CO—Asp—NH—CH(CH2-cyclohexyl)—COOH · CF3COOH |
| object compound (56) | Am—⟨C6H4⟩—OCH2CO—Sar—Asp—Tyr(Me)—OMe · CF3COOH |
| object compound (57) | Am—⟨C6H4⟩—(CH2)2CO—Sar—Asp—Tyr(Me)—OH · CF3COOH |

-continued

| Compound | Formula |
|---|---|
| object compound (58) | Am—⌬—OCH$_2$CO—Sar—Asp—NH—CH(CH$_2$-C$_6$H$_{11}$)—COOH · CF$_3$COOH |
| object compound (59-A) | Am—⌬—O(CH$_2$)$_3$CO—Asp—Val—OH · CF$_3$COOH |
| object compound (59-B) | Am—⌬—O(CH$_2$)$_3$CO—Asp—Val—OH · HCl |
| starting compound (60) | the same as object compound (44) |
| object compound (60) | Am—⌬—(CH$_2$)$_4$CO—Asp—Tyr—OH |
| starting compound (61) | the same as object compound (21-B)(SEQ ID NO: 1) |
| object compound (61-A) (SEQ ID NO: 1) | AcNH—CH(CH$_2$-C$_6$H$_4$-Am(Z))—CO—Sar—Asp(OBzl)—Val—OBzl |
| object compound (61-B) (SEQ ID NO: 1) | AcNH—CH(CH$_2$-C$_6$H$_4$-Am)—CO—Sar—Asp—Val—OH · CF$_3$COOH |
| starting compound (62) | the same as object compound (32) |
| object compound (62) | Am—⌬—O(CH$_2$)$_3$CO—Asp—NH—CH(C$_2$H$_5$)—COOH |
| starting compound (63-A) | Am(Z)—⌬—O(CH$_2$)$_3$COOH |
| starting compound (63-B) | HCl·H—Asp(OBzl)—NH—CH(CH$_2$-2-pyridyl)—COOMe |

-continued

| Compound | Formula |
|---|---|
| object compound (63) | Am(Z)—⟨C6H4⟩—O(CH2)3CO—Asp(OBzl)—NH—CH(CH2-2-pyridyl)—COOMe · CF3COOH |
| object compound (64) | Am—⟨C6H4⟩—O(CH2)3CO—Asp—NH—CH(CH2-2-pyridyl)—COOMe · CF3COOH |
| starting compound (65-A) | Am(Z)—⟨C6H4⟩—OCH2CO—Sar—OH |
| starting compound (65-B) | HCl.H—Asp(OBzl)—D—Val—OBzl |
| object compound (65-A) | Am(Z)—⟨C6H4⟩—OCH2CO—Sar—Asp(OBzl)—D—Val—OBzl |
| object compound (65-B) | Am—⟨C6H4⟩—OCH2CO—Sar—Asp—D—Val—OH · CF3COOH |
| starting compound (66-A) | Am(Z)—⟨C6H4⟩—CH2COOH |
| starting compound (66-B) | HCl.H—Sar—Asp(OBzl)—Val—OBzl |
| object compound (66-A) | Am(Z)—⟨C6H4⟩—CH2CO—Sar—Asp(OBzl)—Val—OBzl |
| object compound (66-B) | Am—⟨C6H4⟩—CH2CO—Sar—Asp—Val—OH · CF3COOH |
| starting compound (67-A) | Am(Z)—⟨C6H4⟩—(CH2)2COOH |
| starting compound (67-B) | HCl.H—Sar—Asp(OBzl)—Val—OBzl |
| object compound (67-A) | Am(Z)—⟨C6H4⟩—(CH2)2CO—Sar—Asp(OBzl)—Val—OBzl |
| object compound (67-B) | Am—⟨C6H4⟩—(CH2)2CO—Sar—Asp—Val—OH · CF3COOH |

-continued

| Compound | Formula |
|---|---|
| starting compound (68-A) | AcNH—CH(CH₂-C₆H₄-Am(Z))—COOH (D) |
| starting compound (68-B) | HCl.H—Sar—Asp(OBzl)—Val—OBzl |
| object compound (68-A) | AcNH—CH(CH₂-C₆H₄-Am(Z))—CO—Sar—Asp(OBzl)—Val—OBzl |
| object compound (68-B) | AcNH—CH(CH₂-C₆H₄-Am)—CO—Sar—Asp—Val—OH .CF₃COOH |
| starting compound (69-A) | Am(Z)—C₆H₄—OCH₂CO—Sar—OH |
| starting compound (69-B) | HCl.H—Asp(OBzl)—Thr(Bzl)—OBzl |
| object compound (69-A) | Am(Z)—C₆H₄—OCH₂CO—Sar—Asp(OBzl)—Thr(Bzl)—OBzl |
| object compound (69-B) | Am—C₆H₄—OCH₂CO—Sar—Asp—Thr—OH .CF₃COOH |
| starting compound (70-A) | Am(Z)—C₆H₄—O(CH₂)₃COOH |
| starting compound (70-B) | HCl.H—Asp(OBzl)—Val—OMe |
| object compound (70-A) | Am(Z)—C₆H₄—O(CH₂)₃CO—Asp(OBzl)—Val—OMe |
| object compound (70-B) | Am—C₆H₄—O(CH₂)₃CO—Asp—Val—OMe .CF₃COOH |
| starting compound (71-A) | Am(Z)—C₆H₄—O(CH₂)₇COOH |
| starting compound (71-B) | HCl.H—Asp(OBzl)—Val—OBzl |
| object compound (71-A) | Am(Z)—C₆H₄—O(CH₂)₇CO—Asp(OBzl)—Val—OBzl |

| Compound | Formula |
|---|---|
| object compound (71-B) | Am—⟨C6H4⟩—O(CH2)7CO—Asp—Val—OH · CF3COOH |
| starting compound (72-A) | Am(Z)—⟨C6H4⟩—(CH2)4COOH |
| starting compound (72-B) | HCl·H—Asp(OBzl)—Tyr(Et)—OBzl |
| object compound (72-A) | Am—⟨C6H4⟩—(CH2)4CO—Asp(OBzl)—Tyr(Et)—OBzl |
| object compound (72-B) | Am—⟨C6H4⟩—(CH2)4CO—Asp—Tyr(Et)—OH · CF3COOH |
| starting compound (73-A) | Am(Z)—⟨C6H4⟩—O(CH2)3COOH |
| starting compound (73-B) | HCl·H—Asp(OBzl)—Thr(Bzl)—OBzl |
| object compound (73-A) | Am(Z)—⟨C6H4⟩—O(CH2)3CO—Asp(OBzl)—Thr(Bzl)—OBzl |
| object compound (73-B) | Am—⟨C6H4⟩—O(CH2)3CO—Asp—Thr—OH · CF3COOH |
| starting compound (74-A) | Am(Z)—⟨C6H4⟩—(CH2)4COOH |
| starting compound (74-B) | HCl·H—Asp(OBzl)—Thr(Bzl)—OBzl |
| object compound (74-A) | Am(Z)—⟨C6H4⟩—(CH2)4CO—Asp(OBzl)—Thr(Bzl)—OBzl |
| object compound (74-B) | Am—⟨C6H4⟩—(CH2)4CO—Asp—Thr—OH · CF3COOH |
| starting compound (75-A) | Am(Z)—⟨C6H4⟩—O(CH2)3COOH |
| object compound (75-A) | Am(Z)—⟨C6H4⟩—O(CH2)3CO—Asp(OBzl)—Leu—OBzl |
| object compound (75-B) | Am—⟨C6H4⟩—O(CH2)3CO—Asp—Leu—OH |

-continued

| Compound | Formula |
|---|---|
| starting compound (76-A) | Am(Z)—⟨C₆H₄⟩—O(CH₂)₃COOH |
| starting compound (76-B) | HCl.H—Asp(OBzl)—Ile—OBzl |
| object compound (76-A) | Am(Z)—⟨C₆H₄⟩—O(CH₂)₃CO—Asp(OBzl)—Ile—OBzl |
| object compound (76-B) | Am—⟨C₆H₄⟩—O(CH₂)₃CO—Asp—Ile—OH |
| starting compound (77-A) | Am(Z)—⟨C₆H₄⟩—O(CH₂)₄COOH |
| starting compound (77-B) | HCl.H—Asp(OBzl)—Ile—OBzl |
| object compound (77-A) | Am(Z)—⟨C₆H₄⟩—O(CH₂)₄CO—Asp(OBzl)—Ile—OBzl |
| object compound (77-B) | Am—⟨C₆H₄⟩—O(CH₂)₄CO—Asp—Ile—OH .CF₃COOH |
| starting compound (78-A) | PAm(Z)—⟨C₆H₄⟩—O(CH₂)₅COOH |
| starting compound (78-B) | HCl.H—Asp(OBzl)—Ile—OBzl |
| object compound (78-A) | Am(Z)—⟨C₆H₄⟩—O(CH₂)₅CO—Asp(OBzl)—Ile—OBzl |
| object compound (78-B) | Am—⟨C₆H₄⟩—O(CH₂)₅CO—Asp—Ile—OH .CF₃COOH |
| starting compound (79-A) | Am(Z)—⟨C₆H₄⟩—O(CH₂)₃COOH |
| starting compound (79-B) | HCl.H—Asp(OBzl)—Nle—OBzl |
| object compound (79-A) | Am(Z)—⟨C₆H₄⟩—O(CH₂)₃CO—Asp(OBzl)—Nle—OBzl |
| object compound (79-B) | Am—⟨C₆H₄⟩—O(CH₂)₃CO—Asp—Nle—OH .CF₃COOH |
| starting compound (80-A) | Am(Z)—⟨C₆H₄⟩—O(CH₂)₃COOH |

-continued

| Compound | Formula |
|---|---|
| starting compound (80-B) | HCl.H—Asp(OBzl)—Nle—OBzl) |
| object compound (80-A) | Am(Z)—⟨C6H4⟩—O(CH2)3CO—Asp(OBzl)—Nle—OBzl |
| object compound (80-B) | Am—⟨C6H4⟩—O(CH2)3CO—Asp—Nle—OH |
| starting compound (81-A) | Am(Z)—⟨C6H4⟩—O(CH2)3COOH |
| starting compound (81-B) | HCl.H—Asp(OBzl)—NHCHCOOBzl (L) [with neopentyl side chain] |
| object compound (81-A) | Am(Z)—⟨C6H4⟩—O(CH2)3CO—Asp(OBzl)—NHCHCOOH (L) [with neopentyl side chain] |
| object compound (81-B) | Am—⟨C6H4⟩—O(CH2)3CO—Asp—NHCHCOOH (L) [with neopentyl side chain] |
| starting compound (82-A) | Am(Z)—⟨C6H4⟩—O(CH2)4COOH |
| starting compound (82-B) | HCl.H—Asp(OBzl)—Phe—OBzl |
| object compound (82-A) | Am(Z)—⟨C6H4⟩—O(CH2)4CO—Asp(OBzl)—Phe—OBzl |
| object compound (82-B) | Am—⟨C6H4⟩—O(CH2)4CO—Asp—Phe—OH .CF3COOH |
| starting compound (83-A) | Am(Z)—⟨C6H4⟩—(CH2)4COOH |
| starting compound (83-B) | HCl.H—Asp(OBzl)—NH⟨*⟩COOBzl [with n-propyl side chain] |
| object compound (83-A) | Am(Z)—⟨C6H4⟩—(CH2)4CO—Asp(OBzl)—NH⟨*⟩COOBzl [with n-propyl side chain] |

-continued

| Compound | Formula |
|---|---|
| object compound (83-B) | Am—⟨C6H4⟩—(CH2)4CO—Asp—NH—*CH(COOH)(CH2CH2CH3)  .CF3COOH |
| starting compound (84-A) | Am(Z)—⟨C6H4⟩—O(CH2)3COOH |
| starting compound (84-B) | HCl.H—Glu(OBzl)—Val—OBzl |
| object compound (84-A) | Am(Z)—⟨C6H4⟩—O(CH2)3CO—Glu(OBzl)—Val—OBzl |
| object compound (84-B) | Am—⟨C6H4⟩—O(CH2)3CO—Glu—Val—OH  .CF3COOH |
| starting compound (85-A) | Am(Z)—⟨C6H4⟩—OCH2COOH |
| starting compound (85-B) | HCl.H—Asp(OBzl)—Val—OBzl |
| object compound (85-A) | Am(Z)—⟨C6H4⟩—OCH2CO—Asp(OBzl)—Val—OBzl |
| object compound (85-B) | Am—⟨C6H4⟩—OCH2CO—Asp—Val—OH  .CF3COOH |
| starting compound (86-A) | Am(Z)—⟨C6H4⟩—O(CH2)5COOH |
| starting compound (86-B) | HCl.H—Asp(OBzl)—Leu—OBzl |
| object compound (86-A) | Am(Z)—⟨C6H4⟩—O(CH2)5CO—Asp(OBzl)—Leu—OBzl |
| object compound (86-B) | Am—⟨C6H4⟩—O(CH2)5CO—Asp—Leu—OH |
| starting compound (87-A) | Am(Z)—⟨C6H4⟩—O(CH2)3COOH |
| starting compound (87-B) | HCL.H—Asp(OBzl)—NH—*C(C(CH3)3)(COOBzl) |

| Compound | Formula |
|---|---|
| object compound (87-A) | Am(Z)—⟨C6H4⟩—O(CH2)3CO—Asp(OBzl)—NH—C(CH3)3—COOBzl |
| object compound (87-B) | Am—⟨C6H4⟩—O(CH2)3CO—Asp—NH—C(CH3)3—COOH · CF3COOH |
| starting compound (88-A) | Am(Z)—⟨C6H4⟩—OCH2CO—Sar—OH |
| starting compound (88-B) | HCl.H—Asp(OBzl)—NH—C(CH3)3—COOBzl |
| object compound (88-A) | Am(Z)—⟨C6H4⟩—OCH2CO—Sar—Asp(OBzl)—NH—C(CH3)3—COOBzl |
| object compound (88-B) | Am—⟨C6H4⟩—OCH2CO—Sar—Asp—NH—C(CH3)3—COOH · CF3COOH |
| starting compound (89-A) | Am(Z)—⟨C6H4⟩—OCH2COOH |
| starting compound (89-B) | HCl.H-βAla—Asp(OBzl)—Val—OBzl |
| object compound (89-A) | Am(Z)—⟨C6H4⟩—OCH2CO-βAla—Asp(OBzl)—Val—OBzl |
| object compound (89-B) | Am—⟨C6H4⟩—OCH2CO-βAla—Asp—Val—OH |
| starting compound (90) | H2N—C(=S)—⟨C6H4⟩—O(CH2)3NHCO—Asp(OBzl)—Val—OBzl |
| object compound (90) | HI.Am—⟨C6H4⟩—O(CH2)3NHCO—Asp(OBzl)—Val—OBzl |
| starting compound (91) | H2N—C(=S)—⟨C6H4⟩—O(CH2)4NHCO—Asp(OBzl)—Val—OBzl |

| Compound | Formula |
|---|---|
| object compound (91) | Am—⟨C6H4⟩—O(CH2)4NHCO—Asp(OBzl)—Val—OBzl · CF3COOH |
| object compound (92) | Am—⟨C6H4⟩—O(CH2)3NHCO—Asp—Val—OH · CF3COOH |
| object compound (93) | Am—⟨C6H4⟩—O(CH2)4NHCO—Asp—Val—OH · CF3COOH |
| starting compound (94) | Am—⟨C6H4⟩—OCH2CO—Sar—Asp—Val—OH · CF3COOH |
| object compound (94) | Am—⟨C6H4⟩—OCH2CO—Sar—Asp—Val—OH · HCl |
| starting compound (95) | Am—⟨C6H4⟩—OCH2CO—Sar—Asp—Val—OH · CF3COOH |
| object compound (95) | Am—⟨C6H4⟩—OCH2CO—Sar—Asp—Val—OH |

In the above-mentioned formulae, Am(z), Am, Bzl, Asp, Val, Sar and Leu are each as explained before, Tyr means L-tyrosine, Ser means L-serine, Gly means glycine, Ala means L-alanine, βAla means β-alanine, Phe means L-phenylalanine, D-Val means D-valine, Thr means L-threonine, Ile means L-isoleucine, Nle means L-norleucine, Glu means L-glutamic acid, Me means methyl, Et means ethyl, Ac means acetyl and Boc means t-butoxycarbonyl.

The following compounds (Examples 14 to 20) were obtained according to a similar manner to that of Example 1.

EXAMPLE 14

The object compound (14)
mp: 95°–100° C.
IR (Nujol): 3300, 1730, 1710, 1650, 1625, 1530 cm$^{-1}$
NMR (DMSO-d$_6$, δ): 0.82 (6H, d, J=6.6 Hz), 1.34–1.68 (4H, m), 1.92–2.22 (3H, m), 2.4–2.85 (4H, m), 4.1–4.29 (1H, m), 4.65–4.84 (1H, m), 5.05 (2H, s), 5.1 (4H, s), 7.1–7.52 (17H, m), 7.9 (2H, d, J=8.1 Hz), 8.11 (1H, d, J=8.2 Hz), 8.22 (1H, d, J=7.9 Hz), 9.12 (2H, br s)

EXAMPLE 15

The object compound (15) mp: ~125° C. (dec.)
IR (Nujol): 3300, 1725, 1650, 1605, 1490 cm$^{-1}$
NMR (DMSO-d$_6$, δ): 1.5–1.85 (4H, m), 2.14 (2H, t like), 2.5–3.01 (4H, m), 3.56 (3H, s), 4.01 (2H, m), 4.36 (1H, m), 4.73 (1H, m), 5.07 (2H, s), 5.1 (2H, s), 6.65 (2H, d, J=8.4 Hz), 6.9–7.1 (4H, m), 7.24–7.5 (12H, m), 7.98 (2H, d, J=8.9 Hz), 8.17 (2H, d, J=6.7 Hz), 8.95–9.37 (2H, br)

EXAMPLE 16

The object compound (16)
mp : ~128° C. (dec.)
IR (Nujol): 3300, 1730, 1640, 1600, 1530 cm$^{-1}$
NMR (DMSO -d$_6$, δ): 1.5–1.83 (4H, m), 2.14 (2H, t like), 2.5–3.05 (4H, m), 3.58 (3H, s), 3.69 (3H, s), 4.01 (2H, t like), 4.40 (1H, m), 4.72 (1H, m), 5.07 (2H, s), 5.10 (2H, s), 6.82 (2H, d, J=8.6 Hz), 6.99 (2H, d, J=8.9 Hz), 7.10 (2H, d, J=8.6 Hz), 7.22–7.50 (12H, m), 7.99 (2H, d, J=8.8 Hz), 8.1–8.29 (2H, m), 9.14 (1H, br s)

EXAMPLE 17

The object compound (17)
mp: 120° C. (dec.)
IR (Nujol): 3300, 1730, 1640, 1605, 1500 cm$^{-1}$
NMR (DMSO-d$_6$, δ): 1.48–1.8 (4H, m), 2.13 (2H, t like), 2.4–3.06 (4H, m), 3.69 (3H, s), 4.00 (2H, t like), 4.46 (1H, m), 4.73 (1H, m), 5.05 (4H, s), 5.10 (2H, s), 6.79 (2H, d, J=8.6 Hz), 6.98 (2H, d, J=8.9 Hz), 7.08 (2H, d, J=8.6 Hz), 7.17–7.5 (15H, m), 7.98 (2H, d, J=8.9 Hz), 8.16 (1H, d, J=8.1 Hz), 8.29 (1H, d, J=7.4 Hz), 9.16 (1H, br s)

EXAMPLE 18

The object compound (18)

mp : 86°–90° C.

IR (Nujol): 3300, 1720, 1610, 1595 cm$^{-1}$

NMR (DMSO-d$_6$, δ): 1.71 (4H, br s), 2.22 (2H, br s), 2.67 (1H, dd, J=17.4 Hz, J=5.9 Hz), 3.05 (1H, dd, J=17.7 Hz, J=9.2 Hz), 3.7–4.2 (4H, m), 4.52 (4H, br s), 5.0 –5.2 (6H, m), 7.00 (2H, d, J=8.3 Hz), 7.2–7.6 (2 1H), 7.99 (2H, d, J=8.4 Hz), 8.69 (1H, d, J=7.4 Hz)

EXAMPLE 19

The object compound (19)

mp: 55°–60° C.

IR (Nujol): 3260, 1725, 1645, 1600 cm$^{-1}$

NMR (DMSO-d$_6$, δ): 2.6–3.1 (4H, m), 2.77 and 2.96 (3H, each s), 3.56 (3H, s), 3.69 (3H, s), 3.97 and 4.01 (2H, each s), 4.4 (1H, m), 4.7–5.3 (7H, m), 6.80 (2H, m), 6.95–7.2 (4H, m), 7.35 (10H, m), 7.97 (2H, d, J=7.9 Hz), 8.2–8.3 (1H, m), 8.4–8.6 (1H, m)

EXAMPLE 20

The object compound (20)

mp: 50°–55° C.

IR (Nujol): 3250 (br), 1720, 1640, 1600 cm$^{-1}$

NMR (DMSO-d$_6$, δ): 2.4–3.1 (4H, m), 2.76 and 2.95 (3H, each s), 3.68 and 3.69 (3H, each s), 3.95 and 3.99 (2H, each s), 4.43 (1H, m), 4.6–5.3 (9H, m), 6.79 (2H, m), 6.99 (2H, d, J=8.9 Hz), 7.08 (2H, d, J=8.9 Hz), 7.1–7.5 (15H, m), 7.95 (2H, d, J=7.9 Hz), 8.32 (1H, m), 8.53 (1H, m)

EXAMPLE 21

The object compound (21-A) was obtained according to a similar manner to that of Example 1.

To a mixture of crude object compound (21-A) (0.787 mmol) and anisole (1 ml), trifluoroacetic acid (4 ml) was added at room temperature, and was stirred at room temperature for 1 hour. After evaporation, 4N hydrochloric acid/dioxane (5 ml) was added to the resulting matter, and then was evaporated in vacuo, and the resulting matter was triturated with diethyl ether and washed with diethyl ether, to give the object compound (21-B) (0.58 g).

mp: 105°–110° C.

IR (Nujol): 1730, 1650 cm$^{-1}$

NMR (DMSO-d$_6$, δ): 0.80 (6H, m), 2.05 (1H, m), 2.65 and 2.75 (3H, each s), 2.6–2.9 (2H, m), 3.19 (2H, m), 3.6–4.4 (3H, m), 4.5–4.8 (2H, m), 5.09 (4H, s), 5.33 (2H, s), 7.2–7.6 (17H, m), 7.80 (2H, d, J=8.0 Hz), 8.17 and 8.36 (1H, each d, J=8.1 Hz), 8.2–8.8 (4H, m)

EXAMPLE 22

To a mixture of 4-[4-(N-benzyloxycarbonylamidino)phenoxy]butyric acid (1.18 g), the starting compound (22) (2.00 g) and 1-hydroxy-1H-benzothiazole (0.51 g) in N,N-dimethylformamide (30 ml) at −20° C. was added 1-(3-dimethylaminopropyl)-3-ethylcarbodiimide (0.61 ml) and stirred at room temperature for 6 hours. The reaction mixture was poured into a mixture of water (300 ml), and ethyl acetate (200 ml), and was adjusted to pH≈10.50 with sodium hydroxide solution. The separated organic layer was washed with 0.5N hydrochloric acid, saturated sodium hydrogen carbonate, water and brine, and dried over magnesium sulfate. After filtration, the filtrate was evaporated in vacuo, and the resulting precipitate was washed with diisopropyl ether to give the object compound (22) (2.04 g).

IR (Nujol): 3300, 1730, 1650, 1600 cm$^{-1}$

NMR (DMSO-d$_6$, δ): 1.92 (2H, m), 2.25 (2H, t, J=6.4 Hz), 2.54–2.78 (2H, m), 2.85–2.93 (2H, m), 4.01 (2H, t, J=6.8 Hz), 4.42 (1H, m), 4.70 (1H, m), 4.99 (2H, s), 5.03 (2H, s), 5.05 (2H, s), 5.10 (2H, s), 6.87 (2H, d, J=8.9 Hz), 6.98 (2H, d, J=8.6 Hz), 7.08 (2H, d, J=8.6 Hz), 7.24–7.39 (20H, m), 7.98 (2H, d, J=8.9 Hz), 8.22 (1H, d, J=8.1 Hz), 8.31 (1H, d, J=7.4 Hz), 9.11 (2H, br s)

MASS (m/z): 905 (M$^+$)

The following compounds (Examples 23 to 36) were obtained according to a similar manner to that of Example 22.

EXAMPLE 23

The object compound (23)

IR (Nujol): 3400, 1740, 1620, 1250 cm$^{-1}$

NMR (DMSO-d$_6$, δ): 1.92 (2H, m), 2.25 (2H, t, J=6.4 Hz), 2.54–2.78 (2H, m), 2.88–2.95 (2H, m), 3.60 (3H, s), 4.01 (2H, t, J=6.8 Hz), 4.45 (1H, m), 4.73 (1H, m), 4.79 (2H, s), 4.94 (2H, s), 5.10 (2H, s), 6.79 (2H, d, J=8.9 Hz), 7.04 (2H, d, J=8.6 Hz), 7.08 (2H, d, J=8.6 Hz), 7.23–7.42 (15H, m), 7.99 (2H, d, J=8.9 Hz), 8.22 (1H, d, J=8.1 Hz), 8.31 (1H, d, J=7.4 Hz), 9.10 (2H, br s)

MASS (m/z): 829 (M$^+$+1)

EXAMPLE 24

The object compound (24)

IR (Nujol): 3400, 3300, 1730, 1700, 1650, 1250 cm$^{-1}$

NMR (DMSO-d$_6$, δ): 1.40–1.50 (4H, m), 2.08 (2H, t like), 2.57 (2H, t like), 2.66–2.76 (2H, m), 2.89–2.93 (2H, m), 3.69 (3H, s), 4.45 (1H, m), 4.41 (1H, m), 5.04 (2H, s), 5.10 (2H, s), 5.20 (2H, s), 6.78 (2H, d, J=8.9 Hz), 7.07 (2H, d, J=8.6 Hz), 7.23–7.40 (17H, m), 7.91 (2H, d, J=8.9 Hz), 8.13 (1H, d, J=8.1 Hz), 8.26 (1H, d, J=7.4 Hz), 9.12 (2H, br s)

EXAMPLE 25

The object compound (25)

IR (Nujol): 3300, 1740, 1700, 1650, 1600, 1250 cm$^{-1}$

NMR (DMSO-d$_6$, δ): 1.06–1.35 (4H, m), 1.39–1.51 (2H, m), 2.06 (2H, t, J=6.9 Hz), 2.49–2.77 (2H, m), 2.85–2.93 (2H, m), 3.70 (3H, s), 3.99 (2H, t, J=6.4 Hz), 4.44 (1H, m), 4.71 (1H, m), 4.99 (2H, s), 5.01 (2H, s), 5.09 (2H, s), 6.78 (2H, d, J=8.9 Hz), 6.98 (2H, d, J=8.6 Hz), 7.07 (2H, d, J=8.6 Hz), 7.24–7.39 (15H, m), 7.97 (2H, d, J=8.9 Hz), 8.12 (1H, d, J=8.1 Hz), 8.25 (1H, d, J=7.4 Hz), 9.10 (2H, br s)

MASS (m/z): 857 (M$^+$+1)

EXAMPLE 26

The object compound (26)

NMR (DMSO-d$_6$, δ): 0.80 (3H, d, J=6.0 Hz), 0.85 (3H, d, J=6.0 Hz), 1.40–1.71 (7H, m), 1.99 (2H, t like), 2.56–2.78 (4H, m), 4.30 (1H, m), 4.71 (1H, m), 5.04 (2H, s), 5.09 (2H, s), 5.10 (2H, s), 7.26–7.49 (17H, m), 7.91 (2H, d, J=8.9 Hz), 8.15 (1H, d, J=8.1 Hz), 8.30 (1H, d, J=7.6 Hz), 9.12 (2H, br s)

MASS (m/z): 763 (M$^+$+1)

EXAMPLE 27

The object compound (27)

IR (Nujol): 3380, 3300, 1740, 1630, 1250 cm$^{-1}$

NMR (DMSO-$d_6$, δ): 1.87–2.02 (2H, m), 2.28 (2H, t, J=7.0 Hz), 2.64–2.83 (2H, m), 3.87 (2H, d, J=6.5 Hz), 4.02 (2H, t, J=6.4 Hz), 4.73 (1H, m), 5.06 (2H, s), 5.10 (2H, s), 5.11 (2H, s), 6.99 (2H, d, J=8.9 Hz), 7.31–7.37 (15H, m), 7.98 (2H, d, J=8.9 Hz), 8.27–8.34 (2H, m), 9.07 (2H, br s)

MASS (m/z): 709 (M$^+$+1)

EXAMPLE 28

The object compound (28)

NMR (DMSO-$d_6$, δ): 1.29 (3H, d, J=7.3 Hz), 1.92 (2H, m), 2.27 (2H, t, J=7.3 Hz), 2.55–2.78 (2H, m), 4.02 (2H, t, J=6.3 Hz), 4.31 (1H, m), 4.72 (1H, m), 5.05 (2H, s), 5.06 (2H, s), 5.10 (2H, s), 6.99 (2H, d, J=8.9 Hz), 7.34–7.40 (15H, m), 7.98 (2H, d, J=8.9 Hz), 8.24 (1H, d, J=8.2 Hz), 8.43 (1H, d, J=7.2 Hz), 9.10 (2H, br s)

EXAMPLE 29

The object compound (29)

IR (Nujol): 3300, 1740, 1650, 1600, 1250 cm$^{-1}$

NMR (DMSO-$d_6$, δ): 1.88–1.99 (2H, m), 2.25 (2H, t, J=7.1 Hz), 2.52–2.60 (2H, m), 2.97–3.07 (2H, m), 4.03 (2H, t, J=6.4 Hz), 4.52 (1H, m), 4.73 (1H, m), 4.97 (2H, s), 4.99 (2H, s), 5.11 (2H, s), 6.99 (2H, d, J=8.9 Hz), 7.18–7.40 (20H, m), 8.00 (2H, d, J=8.9 Hz), 8.22 (1H, d, J=8.1 Hz), 8.36 (1H, d, J=7.4 Hz), 9.16 (2H, br s)

MASS (m/z): 799 (M$^+$+1)

EXAMPLE 30

The object compound (30)

IR (Nujol): 3300, 1740, 1650, 1600, 1250 cm$^{-1}$

NMR (DMSO-$d_6$, δ): 1.12 (3H, t, J=7.1 Hz), 1.56–1.64 (2H, m), 1.90–1.97 (2H, m), 2.18–2.30 (4H, m), 2.57–2.79 (4H, m), 3.90–4.06 (5H, m), 4.64 (1H, m), 5.06 (2H, s), 5.11 (2H, s), 7.00 (2H, d, J=8.9 Hz), 7.14–7.40 (15H, m), 7.68 (1H, d, J=7.9 Hz), 8.00 (2H, d, J=8.9 Hz), 8.16 (1H, d, J=8.1 Hz), 9.12 (2H, br s)

MASS (m/z): 765 (M$^+$+1)

EXAMPLE 31

The object compound (31)

NMR (DMSO-$d_6$, δ): 0.68–0.95 (2H, m), 1.01–1.35 (5H, m), 1.39–1.61 (10H, m), 2.11 (2H, t like), 2.60–2.75 (4H, m), 4.31 (1H, m), 4.71 (1H, m), 5.04 (2H, s), 5.07 (2H, s), 5.09 (2H, s), 7.26–7.37 (15H, m), 7.90 (2H, d, J=8.9 Hz), 8.15 (1H, d, J=8.1 Hz), 8.27 (1H, d, J=7.4 Hz), 9.11 (2H, br s)

MASS (m/z): 803 (M$^+$)

EXAMPLE 32

The object compound (32)

NMR (DMSO-$d_6$, δ): 0.84 (3H, t, J=7.4 Hz), 1.60–1.67 (2H, m), 1.95 (2H, m), 2.27 (2H, t, J=6.4 Hz), 2.57–2.80 (2H, m), 4.02 (2H, t, J=6.8 Hz), 4.20 (1H, m), 4.76 (1H, m), 5.00 (2H, s), 5.06 (2H, s), 5.07 (2H, s), 6.99 (2H, d, J=8.9 Hz), 7.24–7.44 (15H, m), 7.99 (2H, d, J=8.9 Hz), 8.25–8.29 (2H, m), 9.12 (2H, br s)

MASS (m/z): 737 (M$^+$+1)

EXAMPLE 33

The object compound (33)

NMR (DMSO-$d_6$, δ): 0.82 (3H, t, J=7.3 Hz), 1.23–1.34 (2H, m), 1.64 (2H, m), 1.92–2.10 (2H, m), 2.24 (2H, t, J=6.4 Hz), 2.56–2.78 (2H, m), 4.05 (2H, t, J=6.8 Hz), 4.25 (1H, m), 4.72 (1H, m), 5.05 (2H, s), 5.06 (2H, s), 5.09 (2H, s), 6.99 (2H, d, J=8.9 Hz), 7.31–7.40 (15H, m), 7.98 (2H, d, J=8.9 Hz), 8.25 (1H, d, J=8.0 Hz), 8.32 (1H, d, J=7.4 Hz), 9.10 (2H, br s)

EXAMPLE 34

The object compound (34)

NMR (DMSO-$d_6$, δ): 0.62–0.97 (2H, m), 1.01–1.18 (5H, m), 1.42–1.69 (6H, m), 1.94 (2H, m), 2.24 (2H, t, J=6.4 Hz), 2.56–2.76 (2H, m), 4.02 (2H, t, J=6.8 Hz), 4.32 (1H, m), 4.72 (1H, m), 5.05 (2H, s), 5.06 (2H, s), 5.08 (2H, s), 6.98 (2H, d, J=8.9 Hz), 7.23–7.39 (15H, m), 7.98 (2H, d, J=8.9 Hz), 8.23–8.38 (2H, m), 9.13 (2H, br s)

MASS (m/z): 805 (M$^+$+1)

EXAMPLE 35

The object compound (35)

NMR (DMSO-$d_6$, δ): 2.52–2.98 (8H, m), 2.90 (3H, s), 3.70 (3H, s), 3.92 (2H, m), 4.43 (1H, m), 4.72 (1H, m), 5.04 (2H, s), 5.07 (2H, s), 5.10 (2H, s), 6.77 (2H, m), 7.09 (2H, m), 7.26–7.37 (19H, m), 7.82–7.95 (1H, m), 8.22–8.58 (1H, m), 9.18 (2H, br s)

EXAMPLE 36

The object compound (36)

NMR (DMSO-$d_6$, δ): 0.72–0.98 (2H, m), 1.01–1.38 (5H, m), 1.41–1.68 (6H, m), 2.60–2.88 (2H, m), 2.77 (3H, s), 3.98 (2H, m), 4.29 (1H, m), 4.80 (1H, m), 5.05 (2H, s), 5.06 (2H, s), 5.06 (2H, s), 5.09 (2H, s), 6.99 (2H, d, J=8.9 Hz), 7.33–7.37 (15H, m), 7.95 (2H, d, J=8.9 Hz), 8.28–8.33 (1H, m), 8.46–8.60 (1H, m), 9.12 (2H, broad s)

MASS (m/z): 848 (M$^+$+1)

EXAMPLE 37

A mixture of the starting compound (37) (1.70 g) and 10% Pd-C (0.80 g) in a mixture of 1N hydrochloric acid (2.25 ml) and tetrahydrofuran (20 ml) was stirred under $H_2$ gas at room temperature for 6 hours. After filtration, the filtrate was evaporated in vacuo. The resulting matter was washed with isotonic sodium chloride solution to give the object compound (37) (0.60 g).

mp: 180°–183° C.

IR (Nujol): 3250, 1670, 1640, 1600, 1260 cm$^{-1}$

NMR (DMSO-$d_6$, δ): 1.94 (2H, m), 2.27 (2H, t like), 2.63–2.72 (2H, m), 2.80–2.87 (2H, m), 4.08 (2H, t like), 4.30 (1H, m), 4.62 (1H, m), 6.66 (2H, d, J=8.9 Hz), 6.97 (2H, d, J=8.6 Hz), 7.14 (2H, d, J=8.6 Hz), 7.85 (3H, m), 8.25 (1H, d, J=7.4 Hz), 9.05 (2H, s), 9.25 (3H, m), 12.51 (2H, br s)

MASS (m/z): 501 (M$^+$)

The following compounds (Examples 38 to 41) were obtained according to a similar manner to that of Example 37.

EXAMPLE 38

The object compound (38)

mp: 204°–206° C.

IR (Nujol): 3350, 3300, 1670, 1640, 1540, 1260 cm$^{-1}$

NMR (DMSO-$d_6$, δ): 1.94 (2H, m), 2.31 (2H, t, J=6.4 Hz), 2.45–2.62 (2H, m), 2.79–2.96 (2H, m), 3.70 (3H, s), 4.08 (2H, t, J=6.8 Hz), 4.35 (1H, m), 4.61 (1H, m), 6.81 (2H, d, J=8.9 Hz), 7.10–7.16 (4H, m), 7.84–7.93 (3H, m), 8.26 (1H, d, J=7.8 Hz), 9.09 (2H, s), 9.27 (2H, s), 12.00 (2H, br s)

MASS (m/z): 515 (M$^+$)

EXAMPLE 39

The object compound (39)

mp: 163° C. (dec.)

IR (Nujol): 3270, 1700, 1665, 1630, 1605, 1535, 1480 cm$^{-1}$

NMR (DMSO-$d_6$, δ): 0.84 (6H, d, J=6.1 Hz), 1.29–1.85 (6H, m), 1.91–2.23 (3H, m), 2.35–2.78 (2H, m), 3.98–4.2 (3H, m), 4.55–4.73 (1H, m), 7.14 (2H, d, J=8.9 Hz), 7.72 (1H, d, J=8.7 Hz), 7.83 (2H, d, J=8.9 Hz), 8.25 (1H, d, J=7.7 Hz), 8.94 (2H, s), 9.20 (2H, s)

Elemental Analysis $C_{22}H_{32}N_4O_7 \cdot HCl \cdot 1H_2O$

Calcd.: C 50.91, H 6.79, N 10.79, Cl 6.83 Found: C 51.14, H 6.81, N 10.74, Cl 16.37

EXAMPLE 40

The object compound (40)

IR (Nujol): 3300 (br), 1720, 1650 cm$^{-1}$

NMR (DMSO-$d_6$, δ): 0.83 (6H, d, J=6.7 Hz), 1.35–1.7 (4H, m), 1.9–2.25 (3H, m), 2.33–2.8 (4H, m), 4.03–4.2 (1H, m), 4.5–4.7 (1H, m), 7.44 (2H, d, J=8.2 Hz), 7.75 (1H, d, J=8.3 Hz), 7.77 (2H, d, J=8.2 Hz), 8.28 (1H, d, J=7.7 Hz), 9.16 (2H, s), 9.34 (2H, s)

EXAMPLE 41

The object compound (41)

mp: 87°–90° C.

IR (Nujol): 3200 (br), 1640, 1595, 1530 cm$^{-1}$

NMR (DMSO-$d_6$, δ): 2.4–3.1 (4H, m), 2.77 and 2.97 (3H, each s), 3.69 and 3.70 (3H, each s), 3.96 and 4.02 (2H, each s), 4.33 (1H, m), 4.65 (1H, m), 4.93 and 5.06 (2H, each s), 6.82 (2H, m), 7.12 (4H, d, J=8.8 Hz), 7.80 (2H, d, J=8.8 Hz), 7.95 and 8.17 (1H, each d, each J=7.7 Hz), 8.28 and 8.59 (1H, each d, each J=8.2 Hz), 9.02 and 9.22 (4H, each s)

MASS (m/z): 558 (M$^+$+1)

The following compounds (.Examples 42 to 58) were obtained according to a similar manner to that of Example 5.

EXAMPLE 42

The object compound (42)

mp: 200°–202° C.

IR (Nujol): 3300, 1640, 1270 cm$^{-1}$

NMR (DMSO-$d_6$, δ): 1.06–1.35 (4H, m), 1.39–1.51 (2H, m), 2.06 (2H, t, J=6.9 Hz), 2.49–2.77 (2H, m), 2.84–2.94 (2H, m), 3.70 (3H, s), 4.04 (2H, t, J=6.4 Hz), 4.38 (1H, m), 4.62 (1H, m), 6.80 (2H, d, J=8.9 Hz), 7.05–7.20 (4H, m), 7.76 (2H, m), 8.15 (1H, d, J=7.4 Hz), 8.91–9.08 (1H, br s), 9.10–9.21 (2H, br s)

MASS (m/z): 543 (M$^+$+1)

EXAMPLE 43

The object compound (43)

mp: 205–207° C.

IR (Nujol): 3280, 1640, 1550, 1210 cm$^{-1}$

NMR (DMSO-$d_6$, δ): 1.39–1.62 (4H, m), 2.10 (2H, t, J=6.5 Hz), 2.40–2.62 (2H, m), 2.64 (2H, t like), 2.77–2.97 (2H, m), 3.71 (3H, s), 4.33 (1H, m), 4.58 (1H, m), 6.80 (2H, d, J=8.9 Hz), 7.10 (2H, d, J=8.6 Hz), 7.43 (2H, d, J=8.6 Hz), 7.73 (2H, d, J=8.9 Hz), 7.83 (1H, d, J=7.7 Hz), 8.10 (1H, d, J=8.0 Hz), 9.18 (2H, s), 9.23 (2H, s), 12.54 (2H, br s)

MASS (m/z): 513 (M$^+$+1)

EXAMPLE 44

The object compound (44)

mp: ~150° (dec.)

IR (Nujol): 3300, 3100, 1720, 1670, 1610, 1540 cm$^{-1}$

NMR (DMSO-$d_6$, δ): 1.51–1.84 (4H, m), 2.16 (2H, t like), 2.31–3.0 (4H, m), 3.58 (3H, s), 4.08 (2H, t like), 4.35 (1H, m), 4.61 (1H, m), 6.66 (2H, d, J=8.4 Hz), 6.97 (2H, d, J=8.4 Hz), 7.15 (2H, d, J=8.9 Hz), 7.82 (2H, d, J=8.8 Hz), 8.06 (1H, d, J=7.4 Hz), 8.13 (1H, d, J=7.9 Hz), 9.08 (2H, s), 9.14 (2H, s)

MASS (m/z): 529 (M$^+$+1)

EXAMPLE 45

The object compound mp: 208° C. (dec.)

IR (Nujol): 3280, 3090, 1730, 1705, 1660, 1640, 1605, 1540 cm$^{-1}$

NMR (DMSO-$d_6$, δ): 1.51–1.86 (4H, m), 2.15 (2H, t like), 2.32–3.0 (4H, m), 3.58 (3H, s), 3.70 (3H, s), 4.07 (2H, t like), 4.38 (1H, m), 4.60 (1H, m), 6.82 (2H, d, J=8.6 Hz), 7.10 (2H, d, J=8.6 Hz), 7.15 (2H, d, J=8.9 Hz), 7.81 (2H, d, J=8.9 Hz), 8.11 (2H, m), 9.04 (2H, s), 9.14 (2H, s)

MASS (m/z): 543 (M$^+$+1)

EXAMPLE 46

The object compound mp: 173° C. (dec.)

IR (Nujol): 3275, 1680, 1620, 1600, 1540 cm$^{-1}$

NMR (DMSO-$d_6$+TFA, δ): 1.5–1.8 (4H, m), 2.14 (2H, t like), 2.25–3.10 (4H, m), 3.69 (3H, s), 4.05 (2H, t like), 4.32 (1H, m), 4.59 (1H, m), 6.80 (2H, d, J=8.6 Hz), 7.09 (2H, d, J=8.6 Hz), 7.13 (2H, d, J=8.9 Hz), 7.79 (2H, d, J=8.9 Hz), 7.85 (1H, d, J=7.7 Hz), 8.11 (1H, d, J=7.9 Hz), 8.90 (2H, s), 9.11 (2H, s)

MASS (m/z): 529 (M$^+$+1)

EXAMPLE 47

The object compound (47)

mp: 162°–164° C.

IR (Nujol): 3300, 3100, 1660, 1270, 1200 cm$^{-1}$

NMR (DMSO-$d_6$, δ): 1.93–2.00 (2H, m), 2.31 (2H, t, J=7.1 Hz), 2.64–2.75 (2H, m), 3.73 (2H, d, J=5.7 Hz), 4.10 (2H, t, J=6.5 Hz), 4.64 (1H, m), 7.15 (2H, d, J=8.9 Hz), 7.81 (2H, d, J=8.9 Hz), 8.10 (1H, t, J=5.7 Hz), 8.23 (1H, d, J=8.1 Hz), 9.01 (2H, s), 9.14 (2H, s)

MASS (m/z): 395 (M$^+$+1)

EXAMPLE 48

The object compound (48)
mp: 160°–162° C.
IR (Nujol): 3300, 1670, 1600, 1270, 1200 cm$^{-1}$
NMR (DMSO-d$_6$, δ): 1.25 (3H, d, J=7.3 Hz), 1.95 (2H, m), 2.29 (2H, t, J=7.1 Hz), 2.42–2.72 (2H, m), 4.09 (2H, t, J=6.4 Hz), 4.14 (1H, m), 4.62 (1H, m), 7.15 (2H, d, J=8.9 Hz), 7.81 (2H, d, J=8.9 Hz), 8.12 (1H, d, J=7.3 Hz), 8.19 (1H, d, J=7.9 Hz), 8.99 (2H, s), 9.14 (2H, s)
MASS (m/z): 409 (M$^+$30 1)

EXAMPLE 49

The object compound (49)
mp: 118°–120° C.
IR (Nujol): 3280, 1650, 1600, 1540 cm$^{-1}$
NMR (DMSO-d$_6$, δ): 1.70 (4H, br s), 2.19 (2H, m), 2.2–2.6 (1H, m), 2.70 (1H, dd, J=16.6 Hz, J=5.0 Hz), 3.67 (2H, m), 4.08 (2H, br s), 4.22 (1H, m), 4.65 (1H, m), 7.15 (2H, d, J=8.9 Hz), 7.7–7.9 (3H, m), 8.19 (1H, d, J=7.8 Hz), 9.00 and 9.14 (4H, each s)
MASS (m/z): 439 (M$^+$+1)

EXAMPLE 50

The object compound (50)
mp: 207°–209° C.
IR (Nujol): 3300, 1720, 1640, 1270, 1200 cm$^{-1}$
NMR (DMSO-d$_6$, δ): 1.83–2.02 (2H, m), 2.25 (2H, t, J=7.0 Hz), 2.34–2.68 (2H, m), 2.92–3.02 (2H, m), 4.07 (2H, t, J=6.3 Hz), 4.38 (1H, m), 4.62 (1H, m), 7.12–7.26 (7H, m), 7.80 (2H, d, J=8.9 Hz), 7.94 (1H, d, J=7.6 Hz), 8.17 (1H, d, J=7.9 Hz), 8.90 (2H, s), 9.12 (2H, s), 12.55 (2H, br s)
MASS (m/z): 485 (M$^+$+1)

EXAMPLE 51

The object compound (51)
mp: 172°–175° C.
IR (Nujol): 3300, 3100, 1660, 1550, 1200 cm$^{-1}$
NMR (DMSO-d$_6$, δ): 0.80(3H, d, J=6.2 Hz), 0.85 (3H, d, J=6.2 Hz), 1.41–1.65 (7H, m), 2.13 (2H, t, J=6.4 Hz), 2.40–2.71 (4H, m), 4.16 (1H, m), 4.58 (1H,m), 7.44 (2H, d, J=8.9 Hz), 7.74 (2H, d, J=8.9 Hz), 7.97 (1H, d, J=8.0 Hz), 8.11 (1H, d, J=7.9 Hz), 9.13 (2H, s), 9.23 (2H, s)
MASS (m/z): 449 (M$^+$+1)

EXAMPLE 52

The object compound (52)
mp: 177°–180° C.
NMR (Nujol): 0.84 (3H, t, J=7.4 Hz), 1.26–1.34 (2H, m), 1.57–1.65 (2H, m), 1.90–2.10 (2H, m), 2.27 (2H, t, J=6.5 Hz), 2.51–2.70 (2H, m), 4.06–4.16 (3H, m), 4.63 (1H, m), 7.14 (2H, d, J=8.9 Hz), 7.80 (2H, d, J=8.9 Hz), 7.99 (1H, d, J=7.8 Hz), 8.20 (1H, d, J=7.9 Hz), 8.87 (2H, s),9.13 (2H, s), 12.4 (2H, br s)
MASS (m/z): 437 (M$^+$+1)

EXAMPLE 53

The object compound (53)
mp: 217°–219° C.
NMR (DMSO-d$_6$, δ): 0.71–0.98 (2H, m), 1.01–1.39 (5H, m), 1.47–1.71 (6H, m), 1.97 (2H, m), 2.25 (2H, t, J=6.4 Hz), 2.62–2.70 (2H, m), 4.09 (2H, t, J=6.8 Hz), 4.21 (1H, m), 4.62 (1H, m), 7.14 (2H, d, J=8.9 Hz), 7.80 (2H, d, J=8.9 Hz), 7.99 (1H, d, J=7.9 Hz), 8.20 (1H, d, J=7.9 Hz), 8.95 (2H, s), 9.13 (2H, s), 12.43 (2H, br s)
MASS (m/z): 491 (M$^+$+1)

EXAMPLE 54

The object compound (54)
mp: 220°–221° C. (decomp.)
IR (Nujol): 3300, 1670, 1650, 1250 cm$^{-1}$
NMR (DMSO-d$_6$, δ): 1.45–1.79 (2H, m), 1.92–2.02 (2H, m), 2.10–2.29 (4H, m), 2.37–2.68 (4H, m), 3.88 (1H, m), 4.09(2H, t, J=6.4 Hz), 4.52 (1H, m), 7.12–7.24 (7H, m), 7.71 (1H, d, J=8.5 Hz), 7.81 (2H, d, J=8.9 Hz), 8.09 (1H, d, J=7.9 Hz), 8.99 (2H, s) , 9.13 (2H, s), 12.13 (2H, br s)
MASS (m/z): 513 (M$^+$+1)

EXAMPLE 55

The object compound (55)
mp: 186°–188° C.
IR (Nujol): 3300, 1670, 1210 cm$^{-1}$
NMR (DMSO-d$_6$, δ): 0.72–0.98 (2H, m), 1.05–1.18 (5H, m), 1.39–1.71 (10H, m), 2.13 (2H, t like), 2.61–2.71 (4H, m), 4.19 (1H, m), 4.59 (1H, m), 7.44 (2H, d, J=8.9 Hz), 7.73 (2H, d, J=8.9 Hz), 7.95 (1H, d, J=7.9 Hz), 8.11 (1H, d, J=7.9 Hz), 9.07 (2H, s), 9.23 (2H, s), 12.43 (2H, br s)
MASS (m/z): 489 (M$^+$+1)

EXAMPLE 56

The object compound (56)
mp: 65°–73° C.
IR (Nujol): 3270 (br), 1650, 1610, 1510 cm$^{-1}$
NMR (DMSO-d$_6$, δ): 2.3–3.1 (4H, m), 2.78 and 2.98 (3H, each s), 3.56 (3H, s), 3.70 (3H, s), 3.96 and 4.02 (2H, each s), 4.37 (1H, m), 4.65 (1H, m), 4.93 and 5.05 (2H, each s), 6.82 (2H, m), 7.12 (4H, m), 7.77 (2H, d, J=8.3 Hz), 8.14 and 8.23 (1H, each d, J=7.3 Hz (at 8.14), J=8.0 Hz (at 8.23)), 8.37 and 8.53 (1H, each d, J=7.6 Hz (at 8.37), J=8.0 Hz (at 8.53)), 9.00 and 9.13 (4H, each s)

EXAMPLE 57

The object compound (57)
mp: 90°–92° C. (dec.)
IR (Nujol): 1650, 1300, 1250 cm$^{-1}$
NMR (DMSO-d$_6$, δ): 2.58–2.98 (8H, m), 2.75 (3H, s), 3.71 (3H, s), 3.94 (2H, m), 4.32 (1H, m), 4.62 (1H, m), 6.81 (2H, m), 7.12 (2H, m), 7.47 (2H, m), 7.71 (2H, m), 7.90–8.18 (1H, m), 8.07–8.32 (1H, m), 9.04 (2H, s), 9.22 (2H, s)
MASS (m/z): 556 (M$^+$+1)

EXAMPLE 58

The object compound (58)
mp: 95°–98° C.
IR (Nujol): 3300, 1650, 1250 cm$^{-1}$
NMR (DMSO-d$_6$, δ): 0.73–1.00 (2H, m), 1.01–1.39 (5H, m), 1.42–1.69 (6H, m), 2.63–3.02 (2H, m), 2.79 (3H, s), 4.00 (1H, s), 4.04 (1H, s), 4.22 (1H, m), 4.65 (1H, m), 4.94 (1H, s), 5.04 (1H, s), 7.13 (2H, d, J=8.9 Hz), 7.77 (2H, d, J=8.9 Hz), 8.00–8.18 (1H, m), 8.19–8.56 (1H, m), 8.86 (2H, s), 9.12 (2H, s)
MASS (m/z): 534 (M$^+$+1)

EXAMPLE 59

The object compound (59-A) was obtained according to a similar manner to that of Example 5.

A mixture of this object compound (59-A) and 1N-hydrochloric acid (200 ml) was lyopHlized. The resulting powder was dried to give the object compound (59-B) (5.33 g).

mp: 198° C. (dec.)

IR (Nujol): 3270, 1690, 1635, 1600, 1540 cm$^{-1}$

NMR (DMSO-d$_6$, δ): 0.84 (6H, d, J=6.4 Hz), 1.8–2.05 (3H, m), 2.3 (2H, t, J=7 Hz), 2.3–2.8 (2H, m), 3.97–4.22 (3H, m), 4.65 (1H, m), 7.14 (2H, d, J=8.9 Hz), 7.8 (1H, d, J=8.5 Hz), 7.85 (2H, d, J=8.9 Hz), 8.35 (1H, d, J=7.7 Hz), 9.04 (2H, s), 9.24 (2H, s), 12.51 (1H, br s)

Elemental Analysis $C_{20}H_{28}N_4O_7 \cdot HCl \cdot 1H_2O$

Calcd.: C 48.93, H 6.36, N 11.41, Cl 17.22 Found : C 48.77, H 6.52, N 11.22, Cl 6.98

EXAMPLE 60

A mixture of the starting compound (60) (0.7 g) in tetrahydrofuran (3.5 ml) and 1N sodium hydroxide aqueous solution (3.49 ml) was stirred at room temperature for 2 hours. The reaction mixture was adjusted to pH≈5.0 with hydrochloric acid, and the resulting precipitate was collected by filtration to give the object compound (60) (0.5 g).

mp: ~220° C. (dec.)

IR (Nujol): 3280, 1650, 1605, 1550, 1490 cm$^{-1}$

NMR (DMSO-d$_6$+TFA, δ): 1.5–1.85 (4H, m), 2.19 (2H, t like), 2.3–3.0 (4H, m), 4.08 (2H, t like), 4.31 (1H, m), 4.61 (1H, m), 6.65 (2H, d, J=8.4 Hz), 6.97 (2H, d, J=8.4 Hz), 7.15 (2H, d, J=8.9 Hz), 7.81 (2H, d, J=8.8 Hz), 7.83 (1H, d, J=7.8 Hz), 8.15 (1H, d, J=8 Hz), 8.98 (2H, s), 9.13 (2H, s)

MASS (m/z): 515 (M$^+$+1)

Elemental Analysis $C_{25}H_{30}N_4O_8 \cdot 2H_2O$

Calcd.: C 54.53, H 6.22, N 10.17 Found: C 54.32, H 6.04, N 10.08

EXAMPLE 61

To a solution of the starting compound (61) (0.53 g) and triethylamine (0.20 ml) in methylene chloride (5 ml), acetic anhydride (0.066 ml) was added with ice-cooling, and was stirred at room temperature for 4 hours. The reaction mixture was diluted with water and extracted with ethyl acetate, the separated organic layer was washed with diluted hydrochloric acid, saturated sodium bicarbonate aqueous solution, water, and brine, and dried over magnesium sulfate, and evaporated in vacuo to give the object compound (61-A) (crude) (this compound was not isolated).

And the following object compound (61-B) was obtained from said compound (61-A) according to a similar manner to that of Example 5.

mp: 86°–94° C.

IR (Nujol): 1640 (br s), 1530 cm$^{-1}$

NMR (DMSO-d$_6$, δ): 0.86 (6H, m), 1.71 and 1.76 (3H, each s), 2.04 (1H, m), 2.80 and 3.03 (3H, each s), 2.4–3.2 (4H, m), 3.8–5.1 (5H, m), 7.49 (2H, m), 7.72 (2H, m), 7.6–8.6 (3H, m), 9.15 and 9.26 (4H, each s)

MASS (m/z): 535 (M$^+$+1)

HPLC condition column: YMC-PACK R-ODS-15 S-15 120A ODS 50φ× 250 elution: CH$_3$CN: 0.1% trifluoroacetic acid (15:85)

flow: 118 (ml/min)

retention time: 7.6 (min)

EXAMPLE 62

The object compound (62) was obtained from the starting compound (62) according to the similar manners to those of Examples 37 and 13.

mp: 175°–177° C. (dec.)

IR (Nujol): 3300, 1640, 1600, 1260 cm$^{-1}$

NMR (DMSO-d$_6$, δ): 0.75 (3H, t, J=7.2 Hz), 1.60–1.72 (2H, m), 1.94 (2H, m), 2.31 (2H, t like), 2.60–2.68 (2H, m), 3.90 (1H, m), 4.07 (2H, t like), 4.56 (1H, m), 7.09 (2H, d, J=8.9 Hz), 7.56 (1H, d, J=6.6 Hz), 7.72 (2H, d, J=8.9 Hz), 8.38 (1H, d, J=7.6 Hz), 8.75 (2H, br s), 11.18 (2H, br s)

MASS (m/z): 423 (M$^+$+1)

EXAMPLE 63

The object compound (63) was obtained from the starting compounds (63-A) and (63-B) according to a similar manner to that of Example 22.

IR (Nujol): 3300, 1720, 1640, 1250 cm$^{-1}$

NMR (DMSO-d$_6$, δ): 1.91 (2H, m), 2.24 (2H, t, J=7.1 Hz), 2.73–2.96 (2H, m), 3.11–3.15 (2H, m), 3.57 (3H, s), 3.98–4.04 (3H, m), 4.65–4.72 (1H, m), 5.06 (2H, s), 5.11 (2H, s), 6.99 (2H, d, J=8.9 Hz), 7.18–7.26 (2H, m), 7.34–7.40 (10H, m), 7.64–7.72 (1H, m), 7.99 (2H, d, J=8.9 Hz), 8.24 (1H, d, J=8.1 Hz), 8.37 (1H, d, J=7.6 Hz), 8.46 (1H, d, J=4.0 Hz), 9.15 (2H, br s)

MASS (m/z): 724 (M$^+$+1)

EXAMPLE 64

The object compound (64) was obtained according to a similar manner to that of Example 5.

mp: 120°–125° C.

IR (Nujol): 3300, 1740, 1660, 1200 cm$^{-1}$

NMR (DMSO-d$_6$, δ): 1.91 (2H, m), 2.28 (2H, t, J=7.2 Hz), 2.53–2.67 (2H, m), 3.20–3.33 (2H, m), 3.60 (3H, s), 4.07 (2H, t, J=6.4 Hz), 4.55 (1H, m), 4.72 (1H, m), 7.14 (2H, d, J=8.9 Hz), 7.55 (2H, d, J=7.8 Hz), 7.82 (2H, d, J=8.9 Hz), 8.02 (1H, m), 8.19 (1H, d, J=7.8 Hz), 8.40 (1H, d, J=7.8 Hz), 8.63 (1H, d, J=4.9 Hz), 9.13 (2H, s), 9.16 (2H, s)

MASS (m/z): 500 (M$^+$+1)

EXAMPLE 65

The object compound (65-A) was obtained from the starting compound (65-A) and the starting compound (65-B) according to a similar manner to that of Example 1.

The object compound (65-B) was obtained from the object compound (65-A) thus obtained according to a similar manner to that of Example 5.

mp: 50°–54° C. (decomp.)

IR (Nujol): 1640 (br), 1520 cm$^{-1}$

NMR (DMSO-d$_6$, δ): 0.84 (6H, m), 2.07 (1H, m), 2.4–2.8 (2H, m), 2.79 and 3.00 (3H, each s), 3.8–4.2 (3H, m), 4.7 (1H, m), 4.94 and 5.06 (2H, each s), 7.13 (2H, d, J=7.4 Hz), 7.78 (2H, d, J=7.4 Hz), 7.87 and 8.05 (1H, each d, each J=8.8 Hz), 8.27 and 8.57 (1H, each d, each J=8.0 Hz), 9.00 and 9.13 (4H, each s)

EXAMPLE 66

The object compound (66-A) was obtained from the starting compound (66-A) and the starting compound (66-B) according to a similar manner to that of Example 1.

The object compound (66-B) was obtained from the object compound (66-A) thus obtained according to a similar manner to that of Example 5.

mp: 67°–72° C.

IR (Nujol): 1640 (br), 1530 (br) cm$^{-1}$

NMR (DMSO-d$_6$, δ): 0.86 (6H, m), 2.05 (1H, m), 2.3–2.8 (2H, m), 2.82 and 3.03 (3H, each s), 3.74 and 3.89 (2H, each s), 3.8–4.2 (3H, m), 4.68 (1H, m), 7.4 (2H, m), 7.7 (2H, m), 7.8 and 7.97 (1H, m and d (J=8.5 Hz)), 8.3 and 8.52 (1H, each d, J=7.9 Hz), 9.24 and 9.28 (4H, each s)

MASS (m/z): 464 (M$^+$+1)

EXAMPLE 67

The object compound (67-A) was obtained from the starting compound (67-A) and the starting compound (67-B) according to a similar manner to that of Example 1.

The object compound (67-B) was obtained from the object compound (67-A) thus obtained according to a similar manner to that of Example 5.

mp: 52°–56° C.

IR (Nujol): 1660 (br), 1540 cm$^{-1}$

NMR (DMSO-d$_6$, δ): 0.85 (6H, m), 2.05 (1H, m), 2.4–3.0 (6H, m), 2.78 and 2.96 (3H, each s), 3.9–4.2 (3H, m), 4.66 (1H, m), 7.48 (2H, m), 7.71 (2H, m), 7.7 and 7.92 (1H, m and d (J=8.5 Hz)), 8.28 and 8.46 (1H, each d, J=7.9 Hz), 9.15 and 9.24 (4H, each s)

MASS (m/z): 478 (M$^+$+1)

EXAMPLE 68

The object compound (68-A) was obtained from the starting compound (68-A) and the starting compound (68-B) according to a similar manner to that of Example 1.

The object compound (68-B) was obtained from the object compound (68-A) thus obtained according to a similar manner to that of Example 5.

mp: 88°–94° C.

IR (Nujol): 1610 (br s), 1510 cm$^{-1}$

NMR (DMSO-d$_6$, δ): 0.85 (6H, m), 1.71 and 1.76 (3H, each s), 2.08 (1H, m), 2.80 and 3.03 (3H, each s), 2.4–3.2 (4H, m), 3.8–5.1 (5H, m), 7.49 (2H, m), 7.72 (2H, m), 7.6–8.6 (3H, m), 9.18 and 9.26 (4H, each s)

MASS (m/z): 535 (M$^+$+1)

EXAMPLE 69

The object compound (69-A) was obtained from the starting compound (69-A) and the starting compound (69-B) according to a similar manner to that of Example 1.

The object compound (69-B) was obtained from the object compound (69-A) thus obtained according to a similar manner to that of Example 5.

mp: 84°–91° C.

IR (Nujol): 1650 (br), 1610, 1490 cm$^{-1}$

NMR (DMSO-d$_6$, δ): 1.05 (3H, d, J=6.1 Hz), 2.4–2.8 (3H, m), 2.80 and 3.01 (3H, each s), 3.9–4.2 (3H, m), 4.7 (1H, m), 4.95 and 5.06 (2H, each s), 7.13 (2H, d, J=8.9 Hz), 7.58 and 7.74 (1H, d (J=8.5 Hz) and m), 7.78 (2H, d, J=8.9 Hz), 8.38 and 8.70 (1H, each d, J=8.1 Hz), 9.0–9.3 (4H, m)

MASS (m/z): 482 (M$^+$+1)

EXAMPLE 70

The object compound (70-A) was obtained from the starting compound (70-A) and the starting compound (70-B) according to a similar manner to that of Example 1.

The object compound (70-B) was obtained from the object compound (70-A) thus obtained according to a similar manner to that of Example 5.

mp: ~178° C. (dec.)

IR (Nujol): 3300, 3100, 1725, 1660, 1640, 1610, 1540, 1490 cm$^{-1}$

NMR (DMSO-d$_6$, δ): 0.85 (6H, d, J=6.7 Hz), 1.8–2.1 (3H, m), 2.29 (2H, t like), 2.3–2.76 (2H, m), 3.63 (3H, s), 4.0–4.2 (3H, m), 4.65 (1H, m), 7.14 (2H, d, J=8.8 Hz), 7.81 (2H, d, J=8.8 Hz), 8.03 (1H, d, J=8.2 Hz), 8.27 (1H, d, J=7.7 Hz), 9.04 (2H, s), 9.14 (2H, s)

FAB-MASS: 451 (M$^+$+1)

EXAMPLE 71

The object compound (71-A) was obtained from the starting compound (71-A) and the starting compound (71-B) according to a similar manner to that of Example 1.

The object compound (71-B) was obtained from the object compound (71-A) thus obtained according to a similar manner to that of Example 5.

mp: ~169° C. (dec.)

IR (Nujol): 3280, 3100, 1710, 1660, 1600, 1540, 1490 cm$^{-1}$

NMR (DMSO-d$_6$, δ): 0.84 (6H, d, J=6.8 Hz), 1.16–1.8 (10H, m), 1.94–2.2 (3H, m), 2.33–2.8 (2H, m), 3.9–4.25 (3H, m), 4.65 (1H, m), 7.15 (2H, d, J=8.9 Hz), 7.70 (1H, d, J=8.7 Hz), 7.81 (2H, d, J=8.9 Hz), 8.21 (1H, d, J=7.8 Hz), 8.97 (2H, s), 9.13 (2H, s)

EXAMPLE 12

The object compound (72-A) was obtained from the starting compound (72-A) and the starting compound (72-B) according to a similar manner to that of Example 1.

The object compound (72-B) was obtained from the object compound (72-A) thus obtained according to a similar manner to that of Example 5.

mp: ~210° C. (dec.)

IR (Nujol): 3300, 3080, 1660, 1630, 1540, 1510 cm$^{-1}$

NMR (DMSO-d$_6$, δ): 1.3 (3H, t, J=6.9 Hz), 1.51 (4H, m), 2.1 (2H, t like), 2.3–3.1 (6H, m), 3.97 (2H, q, J=6.9 Hz), 4.34 (1H, m), 4.59 (1H, m), 6.79 (2H, d, J=8.6 Hz), 7.08 (2H, d, J=8.6 Hz), 7.43 (2H, d, J=8.3 Hz), 7.74 (2H, d, J=8.3 Hz), 7.83 (1H, d, J=7.7 Hz), 8.11 (1H, d, J=7.9 Hz), 9.24 (4H, s)

EXAMPLE 73

The object compound (73-A) was obtained from the starting compound (73-A) and the starting compound (73-B) according to a similar manner to that of Example 1.

The object compound (73-B) was obtained from the object compound (73-A) thus obtained according to a similar manner to that of Example 5.

mp: 145° C. (dec.)

IR (Nujol): 3320, 3100, 1660, 1610, 1530, 1490 cm$^{-1}$

NMR (DMSO-d$_6$, δ): 1.02 (3H, d, J=6.3 Hz), 1.97 (2H, m), 2.31 (2H, t like), 2.35–2.8 (2H, m), 3.95–4.25 (4H, m), 4.68 (1H, m), 7.15 (2H, d, J=8.9 Hz), 7.55 (1H, d, J=8.6 Hz), 7.81 (2H, d, J=8.9 Hz), 8.34 (1H, d, J=7.9 Hz), 8.98 (2H, s), 9.13 (2H, s)

EXAMPLE 74

The object compound (74-A) was obtained from the starting compound (74-A) and the starting compound (74-B) according to a similar manner to that of Example 1.

The object compound (74-B) was obtained from the object compound (74-A) thus obtained according to a similar manner to that of Example. 5.

mp: 136° C. (dec.)

IR (Nujol): 3300, 3100, 1720, 1670, 1540, 1490 cm$^{-1}$

NMR (DMSO-d$_6$, δ): 1.02 (3H, d, J=6.3 Hz), 1.53 (4H, m), 2.15 (2H, t like), 2.35–2.9 (4H, m), 4.0–4.2 (2H, m), 4.65 (1H, m), 7.45 (2H, d, J=8.3 Hz), 7.51 (1H, d, J=8.6 Hz), 7.74 (2H, d, J=8.3 Hz), 8.24 (1H, d, J=7.9 Hz), 9.15 (2H, s), 9.23 (2H, s)

EXAMPLE 75

The object compound (75-A) was obtained from the starting compound (75-A) and the starting compound (75-B) according to a similar manner to that of Example 1.

The object compound (75-B) was obtained from the object compound (75-A) thus obtained according to a similar manner to that of Example 5.

mp: 198° C. (dec.)

IR (Nujol): 3280, 1630, 1600, 1540, 1480 cm$^{-1}$

NMR (DMSO-d$_6$, δ): 0.84 (6H, m), 1.34–1.72 (3H, m), 1.97 (2H, m), 2.15–2.8 (4H, m), 3.9–4.27 (3H, m), 4.57 (1H, m), 7.11 (2H, d, J=8.8 z), 7.68 (1H, d, J=7.8 Hz), 7.75 (2H, d, J=8.7 Hz), 8.29 (1H, d, J=7.8 Hz), 8.82 (1.5H, s), 10.9 (1.5H, s)

EXAMPLE 76

The object compound (76-A) was obtained from the starting compound (76-A) and the starting compound (76-B) according to a similar manner to that of Example 1.

The object compound (76-B) was obtained from the object compound (76-A) thus obtained according to a similar manner to that of Example 5.

mp: 204° C. (dec.)

IR (Nujol): 3275, 1625, 1535, 1490 cm$^{-1}$

NMR (DMSO-d$_6$, δ): 0.7–1.0 (6H, m), 1.0–1.57 (2H, m), 1.74 (1H, m), 1.98 (2H, m), 2.34 (2H, t like), 2.3–2.8 (2H, m), 3.97 (1H, m), 4.09 (2H, t like), 4.56 (1H, m), 7.10 (2H, d, J=8.8 Hz), 7.48 (2H, d, J=7.8 Hz), 7.73 (2H, d, J=8.6 Hz), 8.39 (1H, d, J=7.6 Hz), 8.73 (1.5H, s), 11.29 (1.5H, s)

EXAMPLE 77

The object compound (77-A) was obtained from the starting compound (77-A) and the starting compound (77-B) according to a similar manner to that of Example 1.

The object compound (77-B) was obtained from the object compound (77-A) thus obtained according to a similar manner to that of Example 5.

IR (Nujol): 3275, 3080, 1700, 1630, 1600, 1540, 1480 cm$^{-1}$

NMR (DMSO-d$_6$, δ): 0.7–1.0 (6H, m), 1.0–1.51 (2H, m), 1.7 (5H, m), 2.19 (2H, t like), 2.25–2.79 (2H, m), 3.97–4.25 (3H, m), 4.63 (1H, m), 7.14 (2H, d, J=8.9 Hz), 7.76 (1H, d, J=9.5 Hz), 7.80 (2H, d, J=8.9 Hz), 8.24 (1H, d, J=7.7 Hz), 9.02 (2H, s), 9.13 (2H, s), 12.52 (1.5H, s)

EXAMPLE 78

The object compound (78-A) was obtained from the starting compound (78-A) and the starting compound (78-B) according to a similar manner to that of Example 1.

The object compound (78-B) was obtained from the object compound (78-A) thus obtained according to a similar manner to that of Example 5.

mp: ~188° C. (dec.)

IR (Nujol): 3300, 3080, 1655, 1600, 1530, 1480 cm$^{-1}$

NMR (DMSO-d$_6$, δ): 0.7–0.92 (6H, m), 1.0–1.8 (9H, m), 2.14 (2H, t like), 2.35–2.77 (2H, m), 3.94–4.27 (3H, m), 4.63 (1H, m), 7.14 (2H, d, J=8.9 Hz), 7.73 (1H, d, J=8.5 Hz), 7.80 (2H, d, J=8.9 Hz), 8.12 (1H, d, J=7.7 Hz), 8.83 (2H, s), 9.13 (2H, s)

EXAMPLE 79

The object compound (79-A) was obtained from the starting compound (79-A) and the starting compound (79-B) according to a similar manner to that of Example 1.

The object compound (79-B) was obtained from the object compound (79-A) thus obtained according to a similar manner to that of Example 5.

mp: 196°–200° C.

IR (Nujol): 3300, 1710, 1640, 1615, 1540, 1490 cm$^{-1}$

NMR (DMSO-d$_6$, δ): 0.83 (3H, br s), 1.22 (4H, m), 1.62 (2H, m), 1.96 (2H, m), 2.29 (2H, m), 2.2–2.8 (2H, m), 4.09 (3H, m), 4.62 (1H, m), 7.13 (2H, d, J=8.5 Hz), 7.81 (2H, d, J=8.5 Hz), 7.80 (1H, m), 8.24 (1H, m), 9.10 and 9.40 (4H, each s)

EXAMPLE 80

The object compound (80-A) was obtained from the starting compound (80-A) and the starting compound (80-B) according to a similar manner to that of Example 1.

The object compound (80-B) was obtained from the object compound (80-A) thus obtained according to a similar manner to that of Example 5.

mp: 216° C. (dec.)

IR (Nujol): 3275, 1680, 1630, 1600, 1540, 1480 cm$^{-1}$

NMR (DMSO-d$_6$, δ): 0.81 (3H, t like), 1.19 (4H, m), 1.4–1.8 (2H, m), 1.85–2.1 (2H, m), 2.2–2.9 (4H, m), 3.93 (1H, m), 4.08 (2H, m), 4.56 (1H, m), 7.09 (2H, d, J=8.9 Hz), 7.57 (1H, d, J=6.9 Hz), 7.72 (2H, d, J=8.8 Hz), 8.37 (1H, d, J=7.9 Hz), 8.75 (2H, s), 11.19 (2H, s)

EXAMPLE 81

The object compound (81-A) was obtained from the starting compound (81-A) and the starting compound (81-B) according to a similar manner to that of Example 1.

The object compound (81-B) was obtained from the object compound (81-A) thus obtained according to a similar manner to that of Example 5.

mp: ~175° C. (dec.)

IR (Nujol): 3300, 3100, 1660, 1600, 1530, 1480 cm$^{-1}$

NMR (DMSO-d$_6$, δ): 0.87 (9H, s), 1.45–1.71 (2H, m), 1.94 (2H, m), 2.27 (2H, t like), 2.3–2.8 (2H, m), 4.09 (2H, t like), 4.21 (1H, m), 4.59 (1H, m), 7.14 (2H, d, J=8.9 Hz), 7.82 (2H, d, J=8.9 Hz), 8.02 (1H, d, J=8.2 Hz), 8.16 (1H, d, J=8.0 Hz), 9.06 (2H, s), 9.14 (2H, s)

EXAMPLE 82

The object compound (82-A) was obtained from the starting compound (82-A) and the starting compound (82-B) according to a similar manner to that of Example 1.

The object compound (82-B) was obtained from the object compound (82-A) thus obtained according to a similar manner to that of Example 5.

mp: ~202° C. (dec.)

IR (Nujol): 3270, 3075, 1690, 1640, 1600, 1530, 1490 cm$^{-1}$

NMR (DMSO-d$_6$, δ): 1.68 (4H, m), 2.15 (2H, t like), 2.3–2.75 (2H, m), 2.78–3.15 (2H, m), 4.07 (2H, t like), 4.39 (1H, m), 4.6 (1H, m), 7.05–7.37 (7H, m), 7.81 (2H, d, J=8.9 Hz), 7.92 (1H, d, J=7.7 Hz), 8.13 (1H, d, J=8 Hz), 9.1 (2H, s), 9.14 (2H, s), 12.58 (1H, s)

FAB-MASS: 499 (M$^+$+1)

EXAMPLE 83

The object compound (83-A) was obtained from the starting compound (83-A) and the starting compound (83-B) according to a similar manner to that of Example 1.

The object compound (83-B) was obtained from the object compound (83-A) thus obtained according to a similar manner to that of Example 5.

mp: 168°–170° C. (dec.)

IR (Nujol): 3300, 1670, 1200 cm$^{-1}$

NMR (DMSO-d$_6$, δ): 0.83 (3H, t, J=7.4 Hz), 1.21–1.38 (2H, m), 1.40–1.68 (4H, m), 2.12 (2H, t like), 2.63–2.71 (6H, m), 4 15 (1H, m), 4.61 (1H, m), 7.44 (2H, d, J=8.9 Hz), 7.73 (2H, d, J=8.9 Hz), 7.92 (1H, d, J=7.9 Hz), 8.11 (1H, d, J=7.8 Hz), 9.01 (2H, s), 9.22 (2H, s), 12.41 (2H, br s)

MASS (m/z): 435 (M$^+$+1)

EXAMPLE 84

The object compound (84-A) was obtained from the starting compound (84-A) and the starting compound (84-B) according to a similar manner to that of Example 1.

The object compound (84-B) was obtained from the object compound (84-A) thus obtained according to a similar manner to that of Example 5.

IR (Nujol): 3280, 3100, 1650, 1605, 1530, 1490 cm$^{-1}$

NMR (DMSO-d$_6$, δ): 0.88 (6H, d, J=6.8 Hz), 1.6–2.44 (9H, m), 3.9–4.2 (3H, m), 4.38 (1H, m), 7.14 (2H, d, J=8.9 Hz), 7.81 (2H, d, J=8.9 Hz), 7.95 (1H, d, J=8.3 Hz), 8.08 (1H, d, J=8 Hz), 9.05 (2H, s), 9.14 (2H, s)

EXAMPLE 85

The object compound (85-A) was obtained from the starting compound (85-A) and the starting compound (85-B) according to a similar manner to that of Example 1.

The object compound (85-B) was obtained from the object compound (85-A) thus obtained according to a similar manner to that of Example 5.

mp: ~199° C. (dec.)

IR (Nujol): 3320, 3100, 1700, 1660, 1610, 1530, 1490 cm$^{-1}$

NMR (DMSO-d$_6$, δ): 0.85 (6H, d, J=6.6 Hz), 2.05 (1H, m), 2.5–2.8 (2H, m), 4.12 (1H, m), 4.68 (2H, s), 4.74 (1H, m), 7.15 (2H, d, J=8.9 Hz), 7.81 (2H, d, J=8.9 Hz), 7.96 (1H, d, J=9.5 Hz), 8.48 (1H, d, J=8 Hz), 9.04 (2H, s), 9.16 (2H, s), 12.54 (1H, s)

EXAMPLE 86

The object compound (86-A) was obtained from the starting compound (86-A) and the starting compound (86-B) according to a similar manner to that of Example 1.

The object compound (86-B) was obtained from the object compound (86-A) thus obtained according to a similar manner to that of Example 5.

mp: ~150° C. (dec.)

IR (Nujol): 3300, 3100, 1660, 1610, 1540, 1490 cm$^{-1}$

NMR (DMSO-d$_6$, δ): 0.82 (3H, d, J=6.2 Hz), 0.87 (3H, d, J=6.2 Hz), 1.25–1.85 (9H, m), 2.13 (2H, t like), 2.3–2.75 (2H, m), 4.07 (2H, t like), 4.19 (1H, m), 4.61 (1H, m), 7.14 (2H, d, J=8.9 Hz), 7.81 (2H, d, J=8.9 Hz), 7.95 (1H, d, J=8.0 Hz), 8.11 (1H, d, J=8.0 Hz), 8.96 (2H, s), 9.13 (2H, s)

EXAMPLE 87

The object compound (87-A) was obtained from the starting compound (87-A) and the starting compound (87-B) according to a similar manner to that of Example 1.

The object compound (87-B) was obtained from the object compound (87-A) thus obtained according to a similar manner to that of Example 5.

mp: 189°–191° C.

IR (Nujol): 1665, 1615, 1525, 1495 cm$^{-1}$

NMR (DMSO-d$_6$, δ): 0.91 (9H, s), 1.97 (2H, m), 2.2–2.6 (3H, m), 2.70 (1H, dd, J=16.7 Hz, J=5.9 Hz), 4.0–4.2 (3H, m), 4.66 (1H, m), 7.14 (2H, d, J=8.9 Hz), 7.66 (1H, d, J=9.2 Hz), 7.83 (2H, d, J=8.9 Hz), 8.40 (1H, d, J=7.6 Hz), 9.16 and 9.21 (4H, each s)

MASS (m/z): 451.2 (M$^+$+1)

EXAMPLE 88

The object compound (88-A) was obtained from the starting compound (88-A) and the starting compound (88-B) according to a similar manner to that of Example 1.

The object compound (88-B) was obtained from the object compound (88-A) thus obtained according to a similar manner to that of Example 5.

mp: 76°–82° C.

IR (Nujol): 1640, 1520 cm$^{-1}$

NMR (DMSO-d$_6$, δ): 0.92 and 0.93 (9H, each s), 2.3–2.8 (2H, m), 2.80 and 3.00 (3H, each s), 3.8–4.2 (3H, m), 4.73 (1H, m), 4.94 and 5.06 (2H, each s), 7.13 (2H, d, J=8.9 Hz), 7.78 (2H, d, J=8.9 Hz), 7.6–8.0 (1H, m), 8.37 and 8.65 (1H, each d, J=7.8 Hz and 7.7 Hz), 9.08 and 9.14 (4H, each s)

MASS (m/z): 494 (M$^+$+1)

EXAMPLE 89

The object compound (89-A) was obtained from the starting compound (89-A) and the starting compound (89-B) according to a similar manner to that of Example 1.

The object compound (89-B) was obtained from the object compound (89-A) thus obtained according to a similar manner to that of Example 5.

mp: ~170° C. (dec.)

IR (Nujol): 3320, 1700, 1660, 1610, 1540, 1480 cm$^{-1}$

NMR (DMSO-d$_6$, δ): 0.87 (6H, d, J=6.7 Hz), 2.05 (1H, m), 2.34 (2H, t like), 2.35–2.8 (2H, m), 3.34 (2H, m), 4.12 (1H, m), 4.61 (2H, s), 4.64 (1H, m), 7.15 (2H, d, J=8.9 Hz), 7.81 (2H, d, J=8.9 Hz), 7.82 (1H, d, J=8.5 Hz), 8.2 (1H, t like), 8.32 (1H, d, J=7.7 Hz), 9.03 (2H, s), 9.16 (2H, s)

EXAMPLE 90

The object compound (90) was obtained from the starting compound (90) according to a similar manner to that of Preparation 18.

mp: ~210° C. (dec.)

IR (Nujol): 3300, 1730, 1650, 1600, 1550 cm$^{-1}$

NMR (DMSO-d$_6$, δ): 0.83 (6H, d, J=6.4 Hz), 1.82 (2H, t like), 2.05 (1H, m), 2.4–2.8 (2H, m), 3.14 (2H, m), 4.05 (2H, t like), 4.23 (1H, m), 4.6 (1H, m), 5.06 (2H, s), 5.10 (2H, s), 6.25–6.4 (2H, m), 7.13 (2H, d, J=8.9 Hz), 7.34 (10H, m), 7.79 (2H, d, J=8.9 Hz), 8.16 (1H, d, J=8.3 Hz)

FAB-MASS: 632 (M+1)

EXAMPLE 91

The object compound (91) was obtained from the starting compound (91) according to a similar manner to that of Preparation 18.

mp: 190° C. (dec.)

IR (Nujol): 3300, 3100, 1725, 1670, 1630, 1610, 1550, 1490 cm$^{-1}$

NMR (DMSO-d$_6$, δ): 0.83 (6H, d, J=5.7 Hz), 1.53 (2H, m), 1.71 (2H, m), 2.06 (1H, m), 2.4–2.8 (2H, m), 3.06 (2H, m), 4.07 (2H, t, J=6.1 Hz), 4.22 (1H, m), 4.62 (1H, m), 5.06 (2H, s), 5.11 (2H, s), 6.2–6.4 (2H, m), 7.14 (2H, d, J=8.9 Hz), 7.35 (10H, m), 7.81 (2H, d, J=8.9 Hz), 8.16 (1H, d, J=8.3 Hz), 9.03 (2H, s), 9.14 (2H, s)

The following compounds (Examples 92 and 93) were obtained according to a similar manner to that of Example 5.

EXAMPLE 92

The object compound (92)

mp: ~188° C. (dec.)

IR (Nujol): 3300, 1710, 1650, 1600, 1550 cm$^{-1}$

NMR (DMSO-d$_6$, δ): 0.84 (6H, d, J=5.4 Hz), 1.85 (2H, t, J=6.4 Hz), 1.9–2.28 (1H, m), 2.35–2.72 (2H, m), 3.17 (2H, m), 4.05 (1H, m), 4.10 (2H, t like), 4.49 (1H, m), 6.42 (2H, m), 7.15 (2H, d, J=8.8 Hz), 7.75 (1H, d, J=8.8 Hz), 7.84 (2H, d, J=8.8 Hz), 9.0 (2H, s), 9.23 (2H, s)

MASS: 452 (M+1)

EXAMPLE 93

The object compound (93)

mp: ~183° C. (dec.)

IR (Nujol): 3310, 1700, 1650, 1635, 1600, 1560, 1540, 1480 cm$^{-1}$

NMR (DMSO-d$_6$, δ): 0.84 (6H, d, J=5.7 Hz), 1.4–1.8 (4H, m), 2.04 (1H, m), 2.3–2.5 (2H, m), 3.07 (2H, m), 4.0–4.2 (3H, m), 4.48 (1H m), 6.2–6.45 (2H, m), 7.14 (2H, d, J=8.8 Hz), 7.73 (1H, d, J=8.9 Hz), 7.81 (2H, d, J=8.8 Hz), 9.02 (2H, s), 9.14 (2H, s), 12.51 (1H, br s)

Example 94

The starting compound (94) (6.89 g) was dissolved in 1N hydrochloric acid (116 ml) and the resultant solution was lyopHlized. The resultant powder was dried to give the object compound (94) (4.34 g).

mp: 133°–140° C.

IR (Nujol): 1620–1660 (br), 1530 cm$^{-1}$

NMR (DMSO-d$_6$, δ): 0.86 (6H, d, J=6.8 Hz), 2.04 (1H, m), 2.2–2.8 (2H, m), 2.80 and 3.0 (3H, each s), 3.8–4.2 (3H, m), 4.6 (1H, m), 5.06 and 5.41 (2H, each s), 7.13 (2H, d, J=8.8 Hz), 8.00 (2H, d, J=8.8 Hz), 7.80–8.20 (1H, m), 8.27 and 8.68 (1H, each d, J=7.8 Hz), 9.05 and 9.25 (4H, each s)

MASS (m/z): 480 (M$^+$+1)

EXAMPLE 95

A mixture of the starting compound (95) (19.61 g) and water (50 ml) was adjusted to pH=6.05 with aqueous ammonia, and the mixture was lyopHlized. The resultant powder was dried to give the object compound (95) (19.17 g).

mp: 167°–170° C.

IR (Nujol): 3260, 1640 (br), 1540, 1485 cm$^{-1}$

NMR (DMSO-d$_6$, δ): 0.80 (6H, d, J=4.9 Hz), 2.03 (1H, m), 2.2–2.8 (2H, m), 2.80 and 3.03 (3H, each s), 3.8–4.7 (4H, m), 4.94 and 5.04 (2H, each s), 7.10 (2H, d, J=8.2 Hz), 7.59 (1H, m), 7.73 (2H, m), 8.45 and 8.72 (1H, m)

MASS (m/z): 480 (M$^+$+1)

---

What we claim is:

1. A peptide compound of the formula

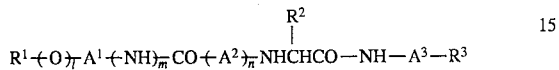

wherein

R¹ is phenyl substituted by one or more members selected from the group consisting of amidino and amidino substituted by a member selected from the group consisting of ar(C1–C6)alkyl; (C1–C6)alkanoyl; (mono, di, or tri)-halo(C1–C6)alkanoyl; (mono, di, or tri)-halo(C1–C6)alkoxycarbonyl; (C1–C6)alkoxycarbonyl; benzoyl; toluoyl; xyloyl; naphthoyl; ar(C1–C6)alkanoyl; aryloxycarbonyl; aryloxy(C1–C6) alkanoyl; arylglyoxyloyl; ar(C1–C6)alkoxycarbonyl which may be unsubstituted or substituted by nitro or (C1–C6)alkoxy; thienylacetyl; imidazolylacetyl; furylacetyl; tetrazolylacetyl; triazolylacetyl; thiadiazolylacetyl; thienylpropionyl; thiadiazolylpropionyl; (C1–C6)alkylsulfonyl; arylsulfonyl; and ar(C1–C6)alkylsulfonyl;

R² is carboxy(C1–C6)alkyl or esterified carboxy(C1–C6)alkyl,

R³ is carboxy or esterified carboxy,

A¹ is (C1–C12)alkylene which may be unsubstituted or substituted by amino or amino substituted by (C1–C6)alkanoyl;

A² is a group of the formula

wherein R⁴ is (C1–C6)alkyl,
or a group of the formula

A³ is (C1–C6)alkylene which may be unsubstituted or substituted by from 1 to 3 substituents selected from the group consisting of (C1–C6)alkyl; ar(C1–C6)alkyl which may be unsubstituted or substituted by from 1 to 3 substituent(s) selected from the group consisting of hydroxy, (C1–C6)alkoxy, ar(C1–C6)alkoxy, (C1–C6)alkanoyloxy, (mono, di, or tri)-halo(C1–C6)alkanoyloxy, (mono, di, or tri)-halo(C1–C6)alkoxycarbonyloxy, (C1–C6)alkoxycarbonyloxy, benzoyloxy, toluoyloxy, xyloyloxy, naphthoyloxy, ar(C1–C6)alkanoyloxy, aryloxycarbonyloxy, aryloxy(C1–C6)alkanoyloxy, arylglyoxyloyloxy, ar(C1–C6)alkoxycarbonyloxy which may be unsubstituted or substituted by nitro or (C1–C6)alkoxy, thienylacetyloxy, imidazolylacetyloxy, furylacetyloxy, tetrazolylacetyloxy, triazolylacetyloxy, thiadiazolylacetyloxy, thienylpropionyloxy, thiadiazolylpropionyloxy, (C1–C6)alkylsulfonyloxy, arylsulfonyloxy, and ar(C1–C6)alkylsulfonyloxy; hydroxy(C1–C6)alkyl; (C1–C6)alkoxy(C1–C6)alkyl; ar(C1–C6)alkoxy(C1–C6)alkyl; acyloxy(C1–C6)alkyl, wherein acyl is a member selected from the group consisting of (C1–C6)alkanoyl, (mono, di, or tri)-halo(C1–C6)alkanoyl, (mono, di, or tri)-halo(C1–C6)alkoxycarbonyl, (C1–C6)alkoxycarbonyl, benzoyl, toluoyl, xyloyl, naphthoyl, ar(C1–C6)alkanoyl, aryloxycarbonyl, aryloxy(C1–C6)alkanoyl, arylglyoxyloyl, ar(C1–C6)alkoxycarbonyl which may be unsubstituted or substituted by nitro or (C1–C6)alkoxy, thienylacetyl, imidazolylacetyl, furylacetyl, tetrazolylacetyl, triazolylacetyl, thiadiazolylacetyl, thienylpropionyl, thiadiazolylpropionyl, (C1–C6)alkylsulfonyl, arylsulfonyl, and ar(C1–C6)alkylsulfonyl; cyclo(C5–C6)alkyl-(C1–C6)alkyl; and heterocyclic(C1–C6)alkyl, wherein heterocyclic is a member selected from the group consisting of unsaturated 3 to 8-membered heteromonocyclic groups containing 1 to 4 nitrogen atoms, saturated 3 to 8-membered heteromonocyclic groups containing 1 to 4 nitrogen atoms, unsaturated condensed heterocyclic groups containing 1 to 5 nitrogen atoms, unsaturated 3 to 8-membered heteromonocyclic groups containing 1 to 2 oxygen atoms and 1 to 3 nitrogen atoms, saturated 3 to 8-membered heteromonocyclic groups containing 1 to 2 oxygen atoms and 1 to 3 nitrogen atoms, unsaturated condensed heterocyclic groups containing 1 to 2 oxygen atoms and 1 to 3 nitrogen atoms, unsaturated 3 to 8-membered heteromonocyclic groups containing 1 to 2 sulfur atoms and 1 to 3 nitrogen atoms, saturated 3 to 8-membered heteromonocyclic groups containing 1 to 2 sulfur atoms and 1 to 3 nitrogen atoms, unsaturated 3 to 8-membered heteromonocyclic groups containing a sulfur atom, unsaturated condensed heterocyclic groups containing 1 to 2 sulfur atoms and 1 to 3 nitrogen atoms, unsaturated 3 to 8-membered heteromonocyclic groups containing 1 to 2 oxygen atoms, saturated 3 to 8-membered heteromonocyclic groups containing 1 to 2 oxygen atoms, and unsaturated condensed heterocyclic groups containing 1 to 2 oxygen atoms;

l, m and n are each the same or different and are an integer of 0 or 1;

with the proviso that A² is not a group of the formula

when l is an integer of 0.

2. A compound of claim 1, wherein R¹ is phenyl substituted by 1 to 3 groups selected from the group consisting of amidino and amidino substituted by a member selected from the group consisting of ar(C1–C6)alkyl; (C1–C6)alkanoyl; (mono, di, or tri)-halo(C1–C6)alkanoyl; (mono, di, or tri)- halo(C1–C6)alkoxycarbonyl; (C1–C6)alkoxycarbonyl; benzoyl; toluoyl; xyloyl; naphthoyl; ar(C1–C6)alkanoyl; aryloxycarbonyl; aryloxy(C1–C6)alkanoyl; arylglyoxyloyl; ar(C1–C6)alkoxycarbonyl which may be unsubstituted or substituted by nitro or (C1–C6)alkoxy; thienylacetyl; imidazolylacetyl; furylacetyl; tetrazolylacetyl; triazolylacetyl; thiadiazolylacetyl; thienylpropionyl; thiadiazolylpropionyl; (C1–C6)alkylsulfonyl; arylsulfonyl; and ar(C1–C6)alkylsulfonyl;

$A^1$ is (C1–C12)alkylene, $A^3$ is (C1–C6)alkylene which may be substituted by (C1–C6)alkyl; phenyl(C1–C6)alkyl which may be unsubstituted or substituted by a substituent selected from the group consisting of hydroxy, (C1–C6)alkoxy, phenyl(C1–C6)alkoxy, and (C1–C6)alkanoyloxy; hydroxy(C1–C6)alkyl; cyclo(C5–C6)alkyl(C1–C6)alkyl; and pyridyl(C1–C6)alkyl;

l is an integer of 1, and m and n are each an integer of 0.

3. A compound of claim 2, wherein $R^1$ is phenyl substituted by amidino, $R^2$ is carboxy(C1–C6)alkyl, $R^3$ is carboxy or esterified carboxy, $A^1$ is (C1–C10)alkylene, and $A^3$ is (C1–C6)alkylene substituted by (C1–C6)alkyl.

4. A compound of claim 3, wherein $R^1$ is 4-amidinophenyl, $R^2$ is carboxymethyl, $R^3$ is carboxy, $A^1$ is trimethylene, and $A^3$ is methylene substituted by isopropyl.

5. A method for the prevention of diseases caused by thrombus formation; restenosis or reocclusion; thrombus formation in case of vascular surgery, valve replacement, extracorporeal circulation or transplantation; disseminated intravascular coagulation; thrombotic thrombocytopenic; essential thrombocytosis; inflammation; immune diseases; or metastasis; or for adjuvant therapy with thrombolytic drug or anticoagulant; which comprises administering an effective amount of a compound of claim 1 or a pharmaceutically acceptable salt thereof to a human being or an animal.

6. A method for the treatment of diseases caused by thrombus formation; restenosis or reocclusion; thrombus formation in case of vascular surgery, valve replacement, extracorporeal circulation or transplantation; disseminated intravascular coagulation; thrombotic thrombocytopenic; essential thrombocytosis; inflammation; immune diseases; or metastasis; or for adjuvant therapy with thrombolytic drug or anticoagulant; which comprises administering an effective amount of a compound of claim 1 or a pharmaceutically acceptable salt thereof to a human being or an animal.

7. A pharmaceutical composition which comprises, as an active ingredient, a compound of claim 1, or a pharmaceutically acceptable salt thereof, in admixture with a pharmaceutically acceptable carrier or excipient.

* * * * *